United States Patent [19]

Wexler et al.

[11] Patent Number: 4,563,211

[45] Date of Patent: Jan. 7, 1986

[54] HERBICIDAL SULFONAMIDES

[75] Inventors: Barry A. Wexler, Wilmington, Del.; William T. Zimmerman, Landenberg, Pa.

[73] Assignee: E. I. Du Pont De Nemours and Company, Wilmington, Del.

[21] Appl. No.: 590,882

[22] Filed: Mar. 19, 1984

[51] Int. Cl.$^4$ .................... C07D 239/47; A01N 47/36
[52] U.S. Cl. ............................................ 71/92; 71/90; 71/91; 71/93; 544/49; 544/211; 544/212; 544/320; 544/321; 544/331; 544/332

[58] Field of Search ............... 544/321, 320, 332, 331, 544/49; 71/92, 90, 91

[56] References Cited

FOREIGN PATENT DOCUMENTS 84020  7/1983  European Pat. Off. ............ 544/321

Primary Examiner—Robert Gerstl

[57] ABSTRACT

Certain sulfonylurea compounds such as 2-[[[4-methoxy-6-(methylselenylmethyl)pyrimidin-2-yl]aminocarbonyl]aminosulfonyl]benzoic acid, methyl ester and 2-[[[4-methoxy-6-(phenylthiomethyl)pyrimidin-2-yl]-aminocarbonyl]aminosulfonyl]benzoic acid, methyl ester provide herbicidal activity.

15 Claims, No Drawings

HERBICIDAL SULFONAMIDES

BACKGROUND OF THE INVENTION

The present invention relates to a class of sulfonylurea compounds, agriculturally suitable compositions containing them and their method-of-use as pre-emergent and/or post-emergent herbicides or plant growth regulants.

Sulfonylurea compounds exhibiting herbicidal activity are disclosed in U.S. Pat. Nos. 4,127,405 and 4,169,719. Herbicidal benzenesulfonylurea compounds containing an ortho-carboxy ester group are disclosed in U.S. Pat. No. 4,383,113.

European Application No. 84,224, published July 27, 1983 discloses herbicidal sulfonylureas such as

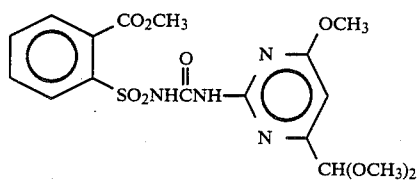

European Application No. 9419 published Apr. 2, 1980 discloses herbicidal sulfonylureas such as

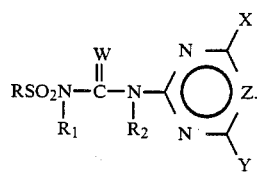

where

R is 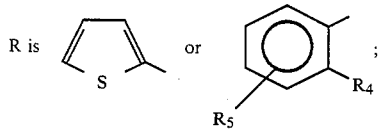

$R_4$ is Cl, Br, F, $NO_2$, $CH_3$, $OCH_3$, $CF_3$ or $S(O)_nR_3$;
X is $CH_3$ or $OCH_3$; and
Y is $CH_2F$, $CH_2Cl$, $CH_2Br$, $C_2$-$C_4$ alkenyl, etc.

SUMMARY OF THE INVENTION

This invention relates to novel compounds of Formula I, agriculturally suitable compositions containing them and their method-of-use as pre-emergent and/or post-emergent herbicides or plant growth regulants.

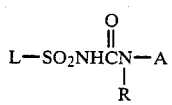

wherein
R is H or $CH_3$;

L is 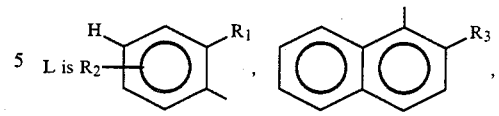

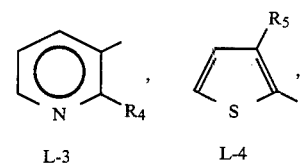

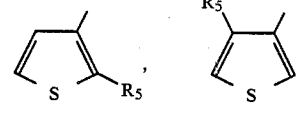

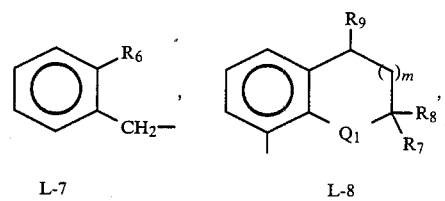

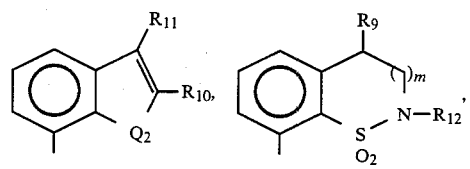

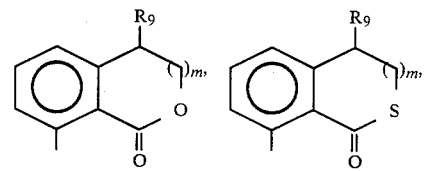

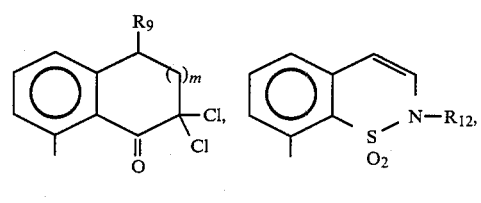

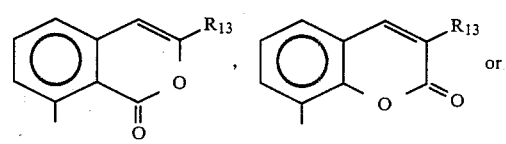

L-17

$R_1$ is $C_1$-$C_4$ alkyl, $C_1$-$C_4$ alkoxy, $OCH_2CH_2OCH_3$, F, Cl, Br, $NO_2$, $CF_3$, $CO_2R_{15}$, $SO_2NR_{16}R_{17}$, $SO_2N(OCH_3)CH_3$, $OSO_2R_{18}$, $S(O)_nR_{19}$, $WCF_3$, $WCHF_2$, $C_3$-$C_4$ alkenyloxy, $C_3$-$C_4$ alkynyloxy, $C_6H_5$, $C_1$-$C_2$ alkyl substituted with $OCH_3$ or $OCH_2CH_3$, $R_2$ is H, F, Cl, Br, $CF_3$, $CH_3$, $OCH_3$ or $SCH_3$;
$R_3$ is H, $CH_3$, $OCH_3$, F, Cl, Br, $SO_2N(CH_3)_2$, $OSO_2CH_3$ or $S(O)_nCH_3$;
$R_4$ is $CH_3$, $CH_2CH_3$, $OCH_3$, $OCH_2CH_3$, F, Cl, Br, $SO_2NR_{16}R_{17}$, $SO_2N(OCH_3)CH_3$ or $S(O)_nR_{19}$;
$R_5$ is $C_1$-$C_3$ alkyl, F, Cl, Br, $NO_2$, $CO_2R_{15}$, $SO_2NR_{16}R_{17}$, $SO_2N(OCH_3)CH_3$ or $S(O)_nR_{19}$;
$R_6$ is Cl, $NO_2$, $CO_2CH_3$, $CO_2CH_2CH_3$, $SO_2N(CH_3)_2$, $OSO_2CH_3$, $SO_2CH_3$, $SO_2CH_2CH_3$, $OCH_3$ or $OCH_2CH_3$;
$R_7$ is H, $CH_3$ or $CH_2CH_3$;
$R_8$ is H, $CH_3$ or $CH_2CH_3$;
$R_9$ is H or $CH_3$;
$R_{10}$ is H or $CH_3$;
$R_{11}$ is H or $CH_3$;
$R_{12}$ is $C_1$-$C_3$ alkyl;
$R_{13}$ is H or $C_1$-$C_3$ alkyl;
$R_{14}$ is H or $CH_3$;
$R_{15}$ is $C_1$-$C_4$ alkyl, $CH_2CH_2OCH_3$, $CH_2CH_2Cl$ or $CH_2CH=CH_2$;
$R_{16}$ is $C_1$-$C_2$ alkyl;
$R_{17}$ is $C_1$-$C_2$ alkyl;
$R_{18}$ is $C_1$-$C_3$ alkyl or $N(CH_3)_2$;
$R_{19}$ is $C_1$-$C_3$ alkyl or $CH_2CH=CH_2$;
m is 0 or 1;
n is 0 or 2;
$Q_1$ is O, S or $SO_2$;
$Q_2$ is O or S; and
W is O, S or $SO_2$;
A is X is $CH_3$, $OCH_3$, $OC_2H_5$, F, Cl, Br, $CF_3$ or $OCHF_2$;
T is H, $SeCH_3$, $SeC_6H_5$, $SCH_3$ or Y is $SeCH_3$, $SeC_6H_5$, $OSi(CH_3)_3$, $CH_2OH$ or $CH_2OSi(CH_3)_3$;
Z is CH or N;
$X_1$ is $CH_3$, $OCH_3$ or $OC_2H_5$;
E is F, Cl or Br;
G is $CH(OCH_3)_2$, $CH(OC_2H_5)_2$, or $C_6H_5$;
$R_{20}$ is H, $CH_3$, $CF_3$, $OCH_3$, F, Cl, Br or $NO_2$;
p is 0, 1 or 2; and
q is 0, 1 or 2;
provided that
(1) when X is F, Cl or Br, then Z is CH;
(2) when m is 1, then $R_9$ is H;
(3) the sum of p and q is less than or equal to 2;
(4) when A is A-2 and L is L-1, then $R_1$ is $C_2$-$C_4$ alkyl, $C_2$-$C_4$ alkoxy, $OCH_2CH_2OCH_3$, $CO_2R_{15}$, $SO_2NR_{16}R_{17}$, $SO_2N(OCH_3)CH_3$, $OSO_2R_{18}$, WCF$_3$, WCHF$_2$, C$_3$-C$_4$ alkenyloxy, C$_3$-C$_4$ alkynyloxy, C$_1$-C$_2$ alkyl substituted with OCH$_3$ or OCH$_2$CH$_3$, C$_6$H$_5$,

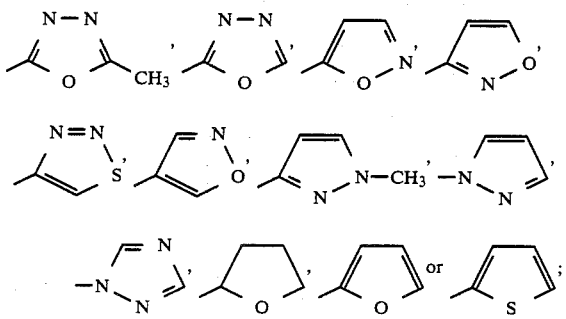

(5) when A is A-4, then L is L-1, L-2, L-3, L-4, L-5, L-6, L-7, L-8 or L-9;

(6) when A is A-4 and L is L-1, then R$_1$ is C$_1$-C$_4$ alkyl, C$_1$-C$_4$ alkoxy, F, Cl, Br, NO$_2$, CF$_3$, CO$_2$R$_{15}$, SO$_2$NR$_{16}$R$_{17}$, SO$_2$N(OCH$_3$)CH$_3$, OSO$_2$R$_{18}$, S(O)$_n$-C$_1$-C$_3$ alkyl, C$_1$-C$_2$ alkyl substituted with OCH$_3$ or OCH$_2$CH$_3$, C$_6$H$_5$,

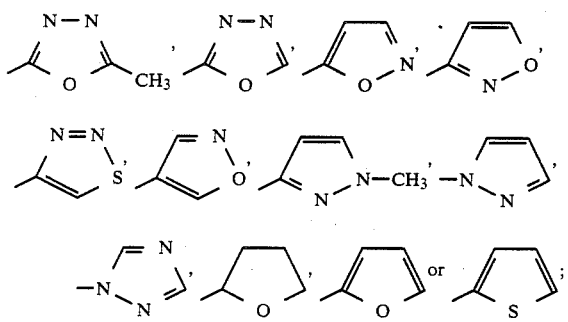

(7) when A is A-5 and L is L-1, then R$_1$ is C$_2$-C$_4$ alkyl, C$_2$-C$_4$ alkoxy, SO$_2$NR$_{16}$R$_{17}$, SO$_2$N(OCH$_3$)CH$_3$, C$_6$H$_5$,

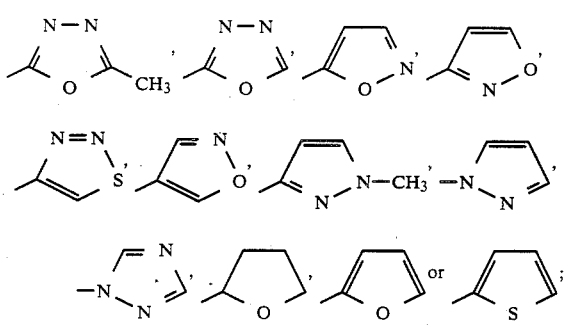

(8) when A is A-5, L is L-1 and R$_1$ is SO$_2$NR$_{16}$R$_{17}$ or SO$_2$N(OCH$_3$)CH$_3$, then E is F or Br;

(9) when A is A-5 and L is L-4, L-5 or L-6, then R$_5$ is C$_1$-C$_3$ alkyl, F, Cl, Br, NO$_2$, SO$_2$NR$_{16}$R$_{17}$, SO$_2$N(OCH$_3$)CH$_3$ or S(O)$_n$R$_{19}$;

(10) when A is A-5 and L is L-10, L-11, L-12, L-13, L-14, L-15, L-16 or L-17, then E is Cl or Br;

(11) when A is A-5, then L is other than L-8, L-11 or L-17; and

(12) R$_{13}$ and R$_{14}$ are not simultaneously H; and their agriculturally suitable salts.

Preferred for reasons of their higher herbicidal acivity, greater plant growth regulant activity and/or more favorable ease of synthesis are:

(1) Compounds of Formula I where R is H and A is A-1;

(2) Compounds of Preferred 1 where R$_2$ is H, R$_{20}$ is H, X is CH$_3$ or OCH$_3$, T is H, p is 0 and q is 0;

(3) Compounds of Preferred 2 where L is L-1, L-5, L-8, L-10, L-11, L-15 or L-17;

(4) Compounds of Preferred 3 where L is L-1 and R$_1$ is C$_1$-C$_2$ alkyl, C$_1$-C$_2$ alkoxy, Cl, NO$_2$, CO$_2$CH$_3$, CO$_2$C$_2$H$_5$, SO$_2$N(CH$_3$)$_2$, SO$_2$CH$_3$, OSO$_2$CH$_3$ or WCHF$_2$.

Specifically preferred for reasons of their highest herbicidal activity, greatest plant growth regulant activity and/or most favorable ease of synthesis are:

2-[[[4-methoxy-6-(phenoxymethyl)pyrimidin-2-yl]aminocarbonyl]aminosulfonyl]benzoic acid, methyl ester, m.p. 178°–180° C.;

2-[[[bis(4,6-trifluoromethyl]pyrimidin-2-yl]aminocarbonyl]aminosulfonyl]benzoic acid, methyl ester, m.p. 153°–161° C.;

2-[[[4-methoxy-6-(methylselenylmethyl)pyrimidin-2-yl]aminocarbonyl[aminosulfonyl]benzoic acid, methyl ester, m.p. 126°–130° C.; and 2-[[[4-methoxy-6-(phenylthiomethyl)pyrimidin-2-yl]aminocarbonyl]aminosulfonyl]benzoic acid, methyl ester, m.p. 149°–152° C.

DETAILED DESCRIPTION OF THE INVENTION

Synthesis

The compounds of Formula I can be prepared by reacting an appropriate sulfonyl isocyanate II with the appropriately substituted aminoheterocycle III, as shown in Equation 1. R, A and L are as previously defined.

Equation 1

III    II

The reaction is best performed in an inert solvent such as methylene chloride or toluene at 25° to 100° C., for 1 to 24 hours. Isolation of the product can be achieved by concentrating the solution and trituration with an appropriate solvent such as butyl chloride.

Alternatively, compounds of Formula I may be prepared by reacting the sulfonamides of Formula IV with the carbamates of Formula V (R′=CH$_3$) in the presence of an excess of trimethylaluminum, as shown in Equation 2, where L, R and A are as previously defined, provided R$_1$ is other than CO$_2$R$_{15}$.

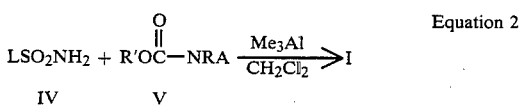

Equation 2

IV    V

The reactions are best performed in an inert solvent such as methylene chloride at the reflux point of the solution (40° C.) for 10 to 24 hours. Isolation of the product is best achieved by exposing the reaction mixture to acetic acid, separation of the layers and concentrating the organic layer to a solid.

Alternatively, compounds of Formula I can be prepared by exposing a phenyl carbamate V (R'=Ph) to the sulfonamide IV in an appropriate solvent such as dioxane at 25° to 100° C. in the presence of a strong base such as 1,8-diazabicyclo[5.4.0]undec-7-ene; acid workup affords the desired product. See EPO Publication No. 44,807 for details. The required carbamates can be prepared from the corresponding amines III and dimethyl or diphenyl carbonate or methyl or phenyl chloroformate and a base such as sodium hydride.

The sulfonyl isocyantes II used in the preparation of I are known in the art and can be prepared by known methods. For example, isocyanates can be prepared by exposing an appropriate benzene or heterocyclic sulfonamide to phosgene in the presence of an alkyl isocyanate and an amine catalyst such as 1,4-diazabicyclo[2.2.2]octane at the reflux point of the solvent. See H. Ulrich and A. A. Y. Sayigh, *Newer Methods of Preparative Organic Chemistry*, Vol. VI, p. 223–241, Academic Press, New York and London, W. Forest Ed.

The sulfonamides IV used in the preparation of I are also known in the art and can be prepared by known methods. For example, exposure of a sulfonyl chloride to ammonium hydroxide results in the formation of the corresponding sulfonamides, e.g., Crossley et al., *J. Am. Chem. Soc.*, 60, 2223 (1938). The appropriate sulfonyl chlorides are prepared by several methods. For example, treatment of a substituted aromatic or heterocyclic ring with chlorosulfonic acid in carbon tetrachloride results in the formaton of the sulfonyl chloride. See Clark et al., *Org. Synth. Coll.*, Vol. 1 2nd Ed. 1941, p. 85.

An alternative method of preparation of sulfonyl chlorides can be achieved from an appropriate amine. Diazotization of an amine with sodium nitrite in acid, followed by exposure of the resulting diazonium salt to sulfur dioxide in the presence of cuprous chloride results in the formation of a sulfonyl chloride. See H. L. Yale and F. Sowinski, *J. Org. Chem.*, 25, 1824, (1960).

The heterocyclic amines III where A is A-1 (T=H) or A-5 may be prepared via generation of the lithium anion of VI, followed by addition of the appropriate electrophile, as shown in Equation 3, where E, R, X, Y and Z are as previously defined. R" is H, CH$_3$, —C(CH$_3$)$_2$, —CO$_2$CH$_3$ or —CO$_2$Ph.

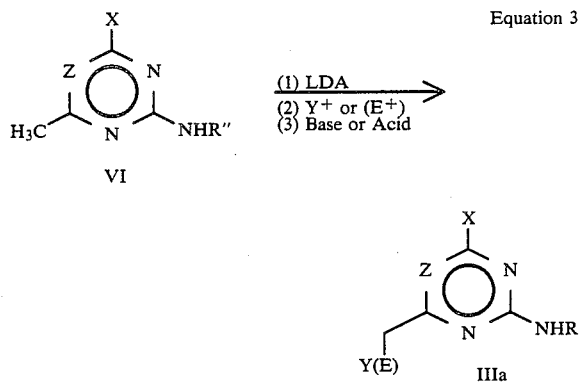

Equation 3

The reaction is generally carried out by adding the heterocycle (VI) to a solution of lithium diisopropylamide (LDA) in tetrahydrofuran at −78° C. followed by the addition of the electrophile (E+ or Y+, for example, N-bromosuccinimide or dimethyldiselenide). In the case where R"=CO$_2$CH$_3$ or CO$_2$Ph, removal of this group is accomplished by treatment with an aqueous base such as potassium hydroxide in methanol.

A second group, T, may be introduced in several ways. Treatment of the reaction mixture with an excess of LDA followed by sequential addition of electrophiles, Y+ and T+, affords the desired dialkylated compound (IIIb) as shown in Equation 4.

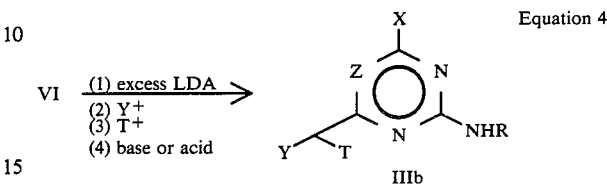

Equation 4

Alternatively, the product of addition of Y+ may be isolated and then retreated as described previously with LDA and T+ to afford the disubstituted compound (IIIb).

Compounds of Formulas IIIa or IIIb wherein Y is OSi(CH$_3$)$_3$ or CH$_2$OSi(CH$_3$)$_3$ can be prepared via silylation of the corresponding alcohols.

Reference to the following papers is suggested for further information regarding the preparation of lithiated heterocycles: T. Murray, J. Hay, D. Portlock, J. Wolfe, *J. Org. Chem.*, 39, 595 (1974), J. Stowell, *Carbanions in Organic Synthesis*, John Wiley and Sons, New York, Chichester, Brisbane, Toronto, Singapore, (1979).

The heterocyclic amines III where A is A-2 are prepared via the sequence described below in Equation 5. R, R" and X$_1$ are as defined previously. Oxidation of the thioether or selenide and thermal elimination of the resulting sulfoxide or selenoxide affords the target compound IIIc. For a review on thermal elimination of sulfoxides and selenoxides, see. D. J. Clive, *Tetrahedron*, 34, 1940 (1978), H. Reich, *Acc. Chem. Res.*, 12, 22 (1979), B. M. Trost. T. H. Saltzman, K. Hiroi, *J. Am. Chem. Soc.*, 98, 4887 (1976).

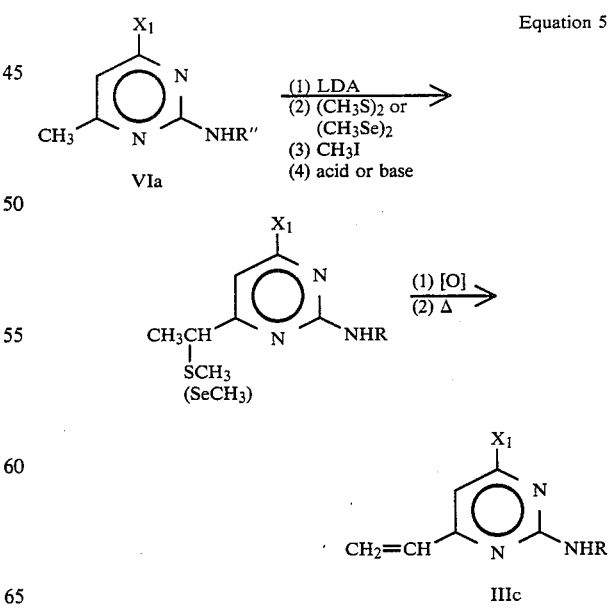

Equation 5

The prerequisite starting heterocycles VI and VIa used in the preparation of A-1, A-2 and A-5 are generally known in the art and are reviewed in *The Chemistry of Heterocyclic Compounds,* Interscience Publ., New York and London. See D. J. Brown, "The Pyrimidines", Vol. XVI and E. M. Smolin and L. Rapaport, "s-Triazines and Derivatives", Vol. XIII. For additional references, see F. C. Schaefer, U.S. Pat. No. 3,154,547 and K. R. Huffman and F. C. Schaefer; *J. Org. Chem.,* 28, 184 (1963).

The heterocyclic amines III where R is a methyl group may be prepared from the corresponding compounds where R is hydrogen by known methods. An example of this type of transformation is described in: *J. Chem. Soc. Perkin I,* 1569 (1981).

The heterocyclic amines III, where A is A-3 and A-4 are best prepared by the exposure of 1,1,1,5,5,5-hexafluoroacetylacetone to guanidine carbonate in an inert solvent such as DMSO as outlined in Equation 6.

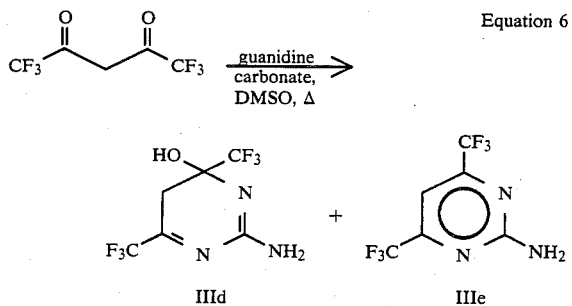

Equation 6

The reaction is best performed at 25° to 125° C. for 1 to 24 hours. The product is usually isolated by pouring the reaction mixture over ice and collecting the resulting solids.

Many of the heterocyclic amines of Formula III in which A is A-1, T is H, Y is as defined previously and q=0 may be prepared by methods known in the art or as described in European Patent Office Publication No. 84,224, published July 27, 1983. For example, when Y is a phenoxy substituent, the known acetoacetic ester VII (U.S. Pat. No. 3,775,467) can be condensed with guanidine carbonate in a suitable solvent such as ethanol preferably above ambient temperature to yield the pyrimidine intermediate VIII, as shown in Equation 7. This can be converted to the chloropyrimidine IX upon treatment with excess phosphorous oxychloride, preferably with heating above ambient temperature. Reaction of IX with an appropriate alkali metal alkoxide in alcohol solvent affords the corresponding alkoxy-substituted pyrimidine of Formula IIIf.

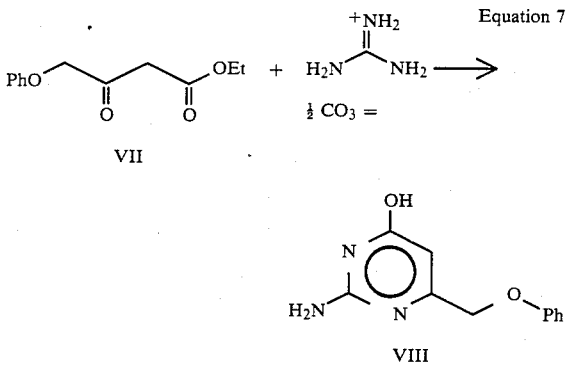

Equation 7

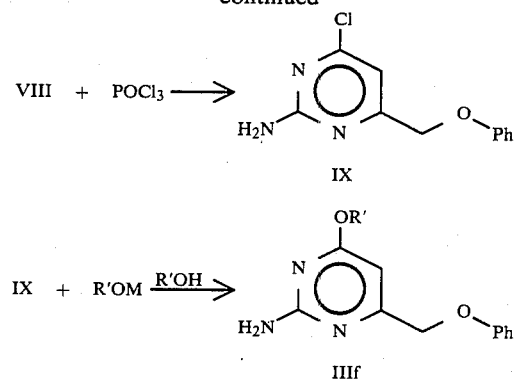

wherein
R' = CH$_3$ or C$_2$H$_5$; and
M = alkali metal.

The synthesis of heterocyclic amines of Formula III wherein A is A-6 can be accomplished as depicted in Equation 8. An alkali metal salt of the appropriate 4-hydroxypyrimidine or triazine X is prepared from X and a suitable base such as an alkali metal alkoxide, for example potassium t-butoxide, in a polar aprotic solvent such as dimethylformamide (DMF). This salt (XI) is then treated with the appropriate haloacetaldehyde acetal such as 2-bromomethyl-1,3-dioxolane and heated in the range of 50° to 150° C., preferably at 110° to 130° C., for 1 to 24 hours. The desired products are conveniently isolated by chromatography on silica gel to separate them from the unwanted N-alkylated isomers.

Equation 8

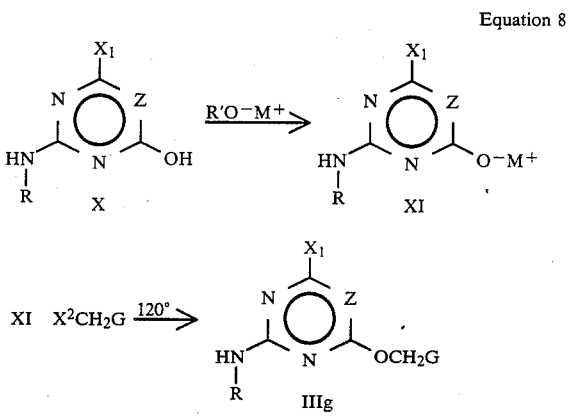

wherein
R, X$_1$, Z and G are as defined previously;
M is an alkali metal;
R' is lower alkyl; and
X$^2$ is halogen.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble.

Acid addition salts, useful in this invention, can be obtained by reacting a compound of Formula I with a suitable acid, e.g., p-toluenesulfonic acid, trichloroacetic acid or the like.

The following examples teach the synthesis of some of the compounds contained within this invention in greater detail.

EXAMPLE 1

Methyl(4-fluoromethyl-6-methoxypyrimidin-2-yl)carbamate

To a stirred solution of lithium diisopropylamide (8.3 mmol) in tetrahydrofuran at $-78°$ C. was added (4-methyl-6-methoxypyrimidin-2-yl)carbamic acid, methyl ester (4.16 mmol). The solution was stirred at $-78°$ C., then N-fluoro-N-2,2-dimethylpropyl-p-toluenesulfonamide (4.6 mmol) in THF was added dropwise. The solution was stirred an additional 1 hour then quenched with brine. A crystalline product was collected, 0.71 g, m.p. 98°–102° C. NMR (90 MHz, CDCl$_3$): δ 4.0 (s, 3H); 4.1 (s, 3H); 5.5 (d, 2H); 1.8 (s, 1H); 8.2 (s, 1H).

EXAMPLE 2

4-Methoxy-6-(phenoxymethyl)-2-pyrimidinamine

A mixture of 7.8 g (36 mmol) of ethyl 2-oxo-4-phenoxybutanoate and 3.4 g (38 mmol) guanidine carbonate was heated to reflux in 100 ml abs. ethanol for 48 hours. Filtration of the cooled suspension afforded 4.6 g of 2-amino-4-hydroxy-6-phenoxymethylpyrimidine in two crops, m.p. 253°–254° (dec). This intermediate (4.3 g, 20 mmol) was heated to reflux in 50 ml phosphorous oxychloride for 2 hours then evaporated. The residue was treated with ice-water and neutralized with 10% sodium hydroxide solution then extracted with chloroform. Evaporation of the extracts left a residue which was purified by dissolution in 15% ethyl acetate/methylene chloride and filtration through silica gel. The filtrate was concentrated and crystallized from ether/1-chlorobutane/hexanes to yield 0.65 g of 2-amino-4-chloro-6-phenoxymethylpyrimidine, m.p. 123°–124°. An additional 0.8 g was deposited from the original aqueous phase, m.p. 118°–121°, for a total of 1.4 g of product. A 1.0 g (4.2 mmol) portion of this material was reacted with 20 mmol sodium methoxide in 30 ml methanol at reflux for 2 hours, then concentrated in vacuo. The residue was triturated with water, collected, water rinsed and dried to 0.9 g of the title compound, m.p. 94°–96°. NMR (90 MHz, CDCl$_3$): δ 3.83 (s, 3H); 4.90 (s, 2H); 6.31 (s, 1H); 6.9–7.1 (m, 3H); 7.22–7.45 (m, 2H) ppm.

EXAMPLE 3

4-Ethylidene-6-methoxy-2-pyrimidinamine

To a stirring solution of 4-methoxy-6-[1-(phenylselenyl)ethyl]-2-pyrimidinamine (14.3 mmol) in 100 ml of CH$_2$Cl$_2$ cooled to $-78°$ C. was added in one portion m-chloroperbenzoic acid (14.3 mmol). The solution was warmed to room temperature, diluted with ether and filtered. A white crystalline solid (0.17 g), m.p. 119°–122° C. was isolated. NMR (200 MHz, CDCl$_3$) δ 3.87 (s, 3H); 5.9 (br s, 2H); 5.5 (d, d, 1H); 6.0 (s, 1H); 6.2–6.6 (m, 2H).

EXAMPLE 4

4-Methoxy-6-phenylselenylmethyl-2-pyrimidinamine

To a stirring solution of lithium diisopropylamide (203 mmol) in tetrahydrofuran, cooled to $-78°$ C. was added methyl(4-methyl-6-methoxypyrimidin-2-yl)carbamate (50.7 mmol). After stirring one hour at $-78°$ C. phenyl diselenide (50.7 mmol) was added, stirred an additional 30 minutes, followed by the addition of methyl iodide (50.7 mmol). The reaction mixture was warmed to $-30°$ C., quenched with brine, the organic phase separated, dried and concentrated. The resulting oil was filtered through a column of silica gel to give 13.3 g of an oil. The crude oil (12.2 g) was dissolved in 206 ml of methanol and 9.4 ml of water, potassium hydroxide (105 mmol) was added and the solution was refluxed for 3 hours. The reaction mixture was cooled to 0° C., neutralized to pH 7 with concentrated HCl and extracted with ethyl acetate. The crude product was flash chromatographed with ether/hexane (35:65) to yield 3 products. Product 1 (0.24 g), the title compound, was obtained as a solid with m.p. 115°–117° C., NMR (60 MHz, CDCl$_3$): δ 3.9 (s, 2H); 4.0 (s, 3H); 5.2 (br. s, 2H); 6.0 (s, 1H); 7.2–7.5 (m, 5H). Product 2 (1.3 g), 4-methoxy-6-[1-methyl-1-(phenylselenyl)ethyl]-2-pyrimidinamine, m.p. 104°–106° C., was the dimethylated product. NMR (200 MHz, CDCl$_3$): δ 1.7 (s, 6H); 3.9 (s, 3H); 5.2 (br. s, 2H); 6.8 (s, 1H); 7.3 (m, 5H). Product 3 (4.6 g) was the mono methylated aminopyrimidine of Formula III in which A is A-1 (X=OCH$_3$, Y=SePh, T=CH$_3$, Z=CH, R=H).

EXAMPLE 5

Methyl[4-methoxy-6-(phenylthiomethyl)pyrimidin-2-yl]carbamate

To a stirring solution of lithium diisopropylamide (126.9 mmol) in 400 ml of tetrahydrofuran at $-78°$ C. was added methyl(4-methyl-6-methoxypyrimidin-2-yl)carbamate (50.8 mmol). After stirring one hour at $-78°$ C., phenyl disulfide (127 mmol) was added. Work-up with brine afforded 30 g of a crude oil. Flash chromatography of the crude product with ether/hexane (50:50) gave two products. Product 1 (5.6 g) a clear oil, was the desired product (A-1, X=OCH$_3$, Y=H, Z=CH, T=SPh), NMR (60 MHz, CDCl$_3$): δ 3.9 (s, 3H); 4.0 (s, 3H); 4.2 (s, 2H); 6.5 (s, 1H); 7.3 (m, 5H); 8.2 (br. s, 1H). Product 2 (1.2 g) was the dithiolated carbamate of Formula V in which R' is CH$_3$, R is H, and A is A-1 (X=OCH$_3$, Y=SPh, Z=CH, T=SPh). NMR (60 MHz, CDCl$_3$): δ 3.7 (s, 3H); 3.9 (s, 3H); 5.4 (s, 1H); 6.4 (s, 1H); 7.0–7.5 (m, 10H); 8.4 (br. s, 1H).

EXAMPLE 6

4-Methoxy-6-(methylselenylmethyl)-2-pyrimidinamine

To a stirring solution of potassium hydroxide (15.6 mmol) in H$_2$O (77.5 mmol) and 50 ml of methanol was added methyl[4-methoxy-6-(methylselenylmethyl)-pyrimidin-2-yl]carbamate (5.2 mmol). The solution was heated to the reflux point for 3 hours, then cooled to 0° C. The solution was neutralized to pH7 with concentrated HCl and then the solvent was removed under reduced pressure. The resulting residue was washed with THF to afford 1.3 g, m.p. 88°–91° C.; NMR (200 MHz, CDCl$_3$): δ 2.01 (s, 3H); 3.48 (s, 2H); 3.85 (s, 3H); 5.1 (br. s, 2H); 5.99 (s, 1H).

EXAMPLE 7

4,6-Bis(trifluoromethyl)-2-pyrimidinamine

A mixture of guanidine carbonate (180 mmol) and 1,1,1,5,5,5-hexafluoro-2,4-pentanedione (120 mmol) was dissolved in 60 ml of DMSO and warmed to 110° C. for 2 to 3 hours. Flash chromatography of the crude reaction product with ether/hexane (50:50) afforded 13.8 g of the title compound as a white crystalline solid, m.p. 94.5°–96° C. NMR (60 MHz, CDCl$_3$): δ 6.5 (br. s, 2H); 7.2 (s, 1H). A second product isolated was the hydroxypyrimidine (A is A-3): m.p. 116°–118.5° C. NMR (90 MHz, CDCl$_3$): δ 7.1 (br. s, 3H); 7.3 (s, 1H).

EXAMPLE 8

Methyl 2-[[[(4-methoxy-6-(phenylselenylmethyl)pyrimidin-2-yl]aminocarbonyl]aminosulfonyl]benzoate To a stirring solution of 4-methoxy-6-(phenylselenylmethyl)-2-pyrimidinamine (0.67 mmol) in 25 ml of methylene chloride was added o-carbomethoxybenzenesulfonyl isocyanate (0.84 mmol). The solution was stirred for 16 hours at room temperature and concentrated. The resulting solid was washed with butyl chloride to afford 0.25 g of the desired product, m.p. 134°–139° C. NMR (200 MHz, CDCl$_3$): δ 3.90 (s, 3H); 3.95 (s, 3H); 4.1 (s, 2H); 6.1 (s, 1H); 7.3 (m, 3H); 1.5 (m, 3H); 7.7 (m, 3H); 8.3 (m, 1H); 12.8 (br. s, 1H).

EXAMPLE 9

Methyl 2-[[[4-(fluoromethyl)-6-methylpyrimidin-2-yl]aminocarbonyl]aminosulfonyl]benzoate To a stirring solution of 4-methyl-6-fluoromethyl-2-pyrimidinamine (1.4 mmol) in 25 ml of CH$_2$Cl$_2$ was added o-carbomethoxybenzenesulfonyl isocyanate (1.77 mmol). After stirring 16 hours the reaction was concentrated and the resulting solid washed with butyl chloride to afford 0.28 g of the desired product, m.p. 181°–186° C. NMR (90 MHz, CDCl$_3$): δ 2.5 (s, 3H); 4.0 (s, 3H); 5.2 (s, 1H); 5.7 (s, 1H); 7.0 (s, 1H); 7.6 (m, 3H); 8.2 (m, 1H); 10.3 (s, 1H); 12.8 (br. s, 1H).

EXAMPLE 10

Methyl 2-[[[bis(4,6-trifluoromethyl)pyrimidin-2-yl]aminocarbonyl]aminosulfonyl]benzoate To a stirring solution of 4,6-bis(trifluoromethyl)-2-pyrimidinamine (2.16 mmol) in 25 ml of methylene chloride was added o-carbomethoxybenzenesulfonyl isocyanate (2.38 mmol). After stirring 10 hours at room temperature the reaction was concentrated and the resulting solid was washed with butyl chloride to afford 0.36 g of the title compound, m.p. 153°–161° C. NMR (90 MHz, CDCl$_3$): δ 4.0 (s, 3H); 7.5–7.8 (m, 4H); 8.3–8.4 (m, 1H); 11.0–11.6 (br. s, 2H).

EXAMPLE 11

Methyl 2-[[[4-Methoxy-6-(phenoxymethyl)pyrimidin-2-yl]aminocarbonyl]aminosulfonyl]benzoate To a mixture of 0.23 g (1.0 mmol) of 4-methoxy-6-(phenoxymethyl)-2-pyrimidinamine in 15 ml dry acetonitrile was added 0.48 g (2.0 mmol) o-carbomethoxybenzenesulfonyl isocyanate and stirred at ambient temperature overnight. Ether was added to the suspension of white solids which were then collected by filtration to afford 0.37 g of the title compound, m.p. 178°–180°. NMR (90 MHz, CDCl$_3$+DMSO-d$_6$): δ 3.91 (s, 3H); 4.02 (s, 3H); 5.20 (s, 2H); 6.69 (s, 1H); 7.0–7.9 (m, 8H); 8.5 (m, 1H); 9.20 (s, NH); 12.9 (s, NH) ppm; IR (nujol) 1725, 1700 cm$^{-1}$.

EXAMPLE 12

4-(1,3-Dioxolan-2-ylmethoxy)-6-methoxy-2-pyrimidinamine

A solution of 8.5 g (0.060 mol) 2-amino-6-methyl-4-pyrimidinone in 45 mL anhydrous dimethylformamide (DMF) was treated with 6.7 g (0.060 mol) potassium t-butoxide then stirred for 10 minutes at ambient temperature. Subsequently, 7.6 mL (0.073 mol) of 2-bromomethyl-1,3-dioxolane was added and the mixture heated to 120° for 3 hours. The DMF was then evaporated under reduced pressure and the residue partitioned between water and ethyl acetate. The aqueous phase was extracted with two additional portions of ethyl acetate then the combined organic phase was washed with water, brine, then dried (MgSO$_4$) and evaporated to an oil. Chromatography on silica gel with 10% ethyl acetate/CH$_2$Cl$_2$ as the eluant afforded 2.3 g of the title compound as a viscous oil. NMR (CDCl$_3$): δ 3.9 (s, 3H), 4.0 (m, 4H), 4.3 (d, J=4 Hz, 2H), 5.15 (NH, br), 5.27 (t, J=4 Hz, 1H), 5.55 (s, 1H) ppm.

EXAMPLE 13

Methyl 2-[[[4-(1,3-Dioxolan-2-ylmethoxy)-6-methoxypyrimidin-2-yl]aminocarbonyl]aminosulfonyl]benzoate A solution of the aminopyrimidine of the preceding example (0.5 g, 2.2 mmol) was dissolved in 10 mL dry acetonitrile then treated with 0.6 g (2.4 mmol) of 2-carbomethoxybenzenesulfonyl isocyanate. The mixture was warmed briefly then stirred at ambient temperature for several hours and subsequently evaporated to dryness. Trituration of the residue with ether afforded 0.85 g of the title compound as colorless crystals, m.p. 102°–104° (dec.). NMR (200 MHz, CDCl$_3$): δ 3.90 (s, 3H), 4.05 (s, 3H), 3.95 (m, 4H), 4.39 (d, J=4 Hz, 2H), 5.26 (t, J=4 Hz, 1H), 5.85 (s, 1H), 7.2 (NH, br), 7.68 (m, 3H), 8.45 (m, 1H), 12.4 (NH, br) ppm; IR (nujol) 1715, 1730 cm$^{-1}$.

Using the procedures of Examples 1–13 the following compounds may be prepared.

TABLE 1a

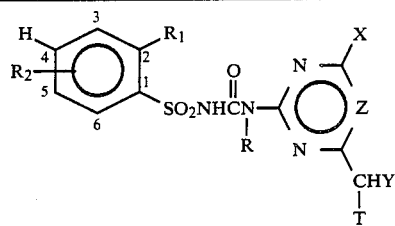

| $R_1$ | $R_2$ | R | X | T | Y | Z | m.p. (°C.) |
|---|---|---|---|---|---|---|---|
| H | H | H | $OCH_3$ | H | SPh | CH | |
| H | H | H | $OCH_3$ | H | SePh | CH | |
| $CO_2CH_3$ | H | H | $CH_3$ | H | $SeCH_3$ | CH | |
| $CO_2CH_3$ | H | H | $CH_3$ | H | SePh | CH | |
| $CO_2CH_3$ | H | H | $CH_3$ | H | SPh | CH | |
| $CO_2CH_3$ | H | H | $CH_3$ | H | SOPh | CH | |
| $CO_2CH_3$ | H | H | $CH_3$ | H | $SO_2Ph$ | CH | |
| $CO_2CH_3$ | H | H | $CH_3$ | H | OPh | CH | |
| $CO_2CH_3$ | H | H | $CH_3$ | $SeCH_3$ | $SeCH_3$ | CH | |
| $CO_2CH_3$ | H | H | $CH_3$ | $SeCH_3$ | SePh | CH | |
| $CO_2CH_3$ | H | H | $CH_3$ | $SeCH_3$ | SPh | CH | |
| $CO_2CH_3$ | H | H | $CH_3$ | $SeCH_3$ | SOPh | CH | |
| $CO_2CH_3$ | H | H | $CH_3$ | $SeCH_3$ | $SO_2Ph$ | CH | |
| $CO_2CH_3$ | H | H | $CH_3$ | SePh | $SeCH_3$ | CH | |
| $CO_2CH_3$ | H | H | $CH_3$ | SePh | SePh | CH | |
| $CO_2CH_3$ | H | H | $CH_3$ | SePh | Sph | CH | |
| $CO_2CH_3$ | H | H | $CH_3$ | SePh | SOPh | CH | |
| $CO_2CH_3$ | H | H | $CH_3$ | SePh | $SO_2Ph$ | CH | |
| $CO_2CH_3$ | H | H | $CH_3$ | $SCH_3$ | $SeCH_3$ | CH | |
| $CO_2CH_3$ | H | H | $CH_3$ | $SCH_3$ | SePh | CH | |
| $CO_2CH_3$ | H | H | $CH_3$ | $SCH_3$ | SPh | CH | |
| $CO_2CH_3$ | H | H | $CH_3$ | $SCH_3$ | SOPh | CH | |
| $CO_2CH_3$ | H | H | $CH_3$ | $SCH_3$ | $SO_2Ph$ | CH | |
| $CO_2CH_3$ | H | H | $CH_3$ | $SCH_3$ | OPh | CH | |
| $CO_2CH_3$ | H | H | $CH_3$ | H | S-(2-CH₃-C₆H₄) | CH | |
| $CO_2CH_3$ | H | H | $CH_3$ | H | S-(3-CF₃-C₆H₄) | CH | |
| $CO_2CH_3$ | H | H | $CH_3$ | H | S-(4-Cl-C₆H₄) | CH | |
| $CO_2CH_3$ | H | $CH_3$ | $CH_3$ | H | $SeCH_3$ | CH | |
| $CO_2CH_3$ | H | $CH_3$ | $CH_3$ | H | SePh | CH | |
| $CO_2CH_3$ | H | $CH_3$ | $CH_3$ | H | SPh | CH | |
| $CO_2CH_3$ | H | $CH_3$ | $CH_3$ | H | $SO_2Ph$ | CH | |
| $CO_2CH_3$ | H | $CH_3$ | $CH_3$ | $SeCH_3$ | $SeCH_3$ | CH | |
| $CO_2CH_3$ | H | $CH_3$ | $CH_3$ | SPh | SPh | CH | |
| $CO_2CH_3$ | H | $CH_3$ | $CH_3$ | H | OPh | CH | |
| $CO_2CH_3$ | 5-$OCH_3$ | H | $CH_3$ | H | $SeCH_3$ | CH | |
| $CO_2CH_3$ | 5-$OCH_3$ | H | $CH_3$ | H | SePh | CH | |
| $CO_2CH_3$ | 3-$OCH_3$ | H | $CH_3$ | H | SPh | CH | |
| $CO_2CH_3$ | 6-$OCH_3$ | H | $CH_3$ | H | SOPh | CH | |
| $CO_2CH_3$ | 6-$OCH_3$ | H | $CH_3$ | H | $SO_2Ph$ | CH | |
| $CO_2CH_3$ | 5-$OCH_3$ | H | $CH_3$ | H | OPh | CH | |
| $CO_2CH_3$ | 5-$OCH_3$ | H | $CH_3$ | $SeCH_3$ | $SeCH_3$ | CH | |
| $CO_2CH_3$ | 3-$OCH_3$ | H | $CH_3$ | $SeCH_3$ | SePh | CH | |
| $CO_2CH_3$ | 3-$OCH_3$ | H | $CH_3$ | $SeCH_3$ | SPh | CH | |
| $CO_2CH_3$ | 5-$OCH_3$ | H | $CH_3$ | $SeCH_3$ | $SO_2Ph$ | CH | |
| $CO_2CH_3$ | 3-$CF_3$ | H | $CH_3$ | H | $SeCH_3$ | CH | |
| $CO_2CH_3$ | 5-$CF_3$ | H | $CH_3$ | H | SePh | CH | |
| $CO_2CH_3$ | 6-$CF_3$ | H | $CH_3$ | H | SPh | CH | |
| $CO_2CH_3$ | 6-$CF_3$ | H | $CH_3$ | H | $SO_2Ph$ | CH | |
| $CO_2CH_3$ | 5-$CF_3$ | H | $CH_3$ | H | OPh | CH | |

TABLE 1a-continued

| R₁ | R₂ | R | X | T | Y | Z | m.p. (°C.) |
|---|---|---|---|---|---|---|---|
| CO₂CH₃ | 5-CF₃ | H | CH₃ | SPh | SPh | CH | |
| CO₂CH₃ | 3-Cl | H | CH₃ | H | SeCH₃ | CH | |
| CO₂CH₃ | 5-Cl | H | CH₃ | H | SePh | CH | |
| CO₂CH₃ | 6-Cl | H | CH₃ | H | SPh | CH | |
| CO₂CH₃ | 6-Cl | H | CH₃ | H | SO₂Ph | CH | |
| CO₂CH₃ | 5-Br | H | CH₃ | H | SeCH₃ | CH | |
| CO₂CH₃ | 5-Br | H | CH₃ | H | SePh | CH | |
| CO₂CH₃ | 6-Br | H | CH₃ | H | SPh | CH | |
| CO₂CH₃ | 3-F | H | CH₃ | H | SeCH₃ | CH | |
| CO₂CH₃ | 3-F | H | CH₃ | H | SePh | CH | |
| CO₂CH₃ | 3-F | H | CH₃ | H | SPh | CH | |
| CO₂CH₃ | 5-F | H | CH₃ | H | SOPh | CH | |
| CO₂CH₃ | 6-F | H | CH₃ | H | SO₂Ph | CH | |
| CO₂CH₃ | 6-F | H | CH₃ | SeCH₃ | SeCH₃ | CH | |
| CO₂CH₃ | 3-F | H | CH₃ | SePh | SePh | CH | |
| CO₂CH₃ | 5-F | H | CH₃ | SPh | SPh | CH | |
| CO₂CH₃ | 5-CH₃ | H | CH₃ | H | SeCH₃ | CH | |
| CO₂CH₃ | 6-CH₃ | H | CH₃ | H | SPh | CH | |
| CO₂CH₃ | H | H | OCH₃ | H | SeCH₃ | CH | 144–147 |
| CO₂CH₃ | H | H | OCH₃ | H | SePh | CH | 134–139 |
| CO₂CH₃ | H | H | OCH₃ | H | SPh | CH | 149–152 |
| CO₂CH₃ | H | H | OCH₃ | H | SOPh | CH | 176–178.5 |
| CO₂CH₃ | H | H | OCH₃ | H | SO₂Ph | CH | |
| CO₂CH₃ | H | H | OCH₃ | H | OPh | CH | 178–180 |
| CO₂CH₃ | H | H | OCH₃ | SeCH₃ | SeCH₃ | CH | |
| CO₂CH₃ | H | H | OCH₃ | SeCH₃ | SePh | CH | |
| CO₂CH₃ | H | H | OCH₃ | SeCH₃ | SPh | CH | |
| CO₂CH₃ | H | H | OCH₃ | SeCH₃ | SOPh | CH | |
| CO₂CH₃ | H | H | OCH₃ | SeCH₃ | SO₂Ph | CH | |
| CO₂CH₃ | H | H | OCH₃ | SePh | SeCH₃ | CH | |
| CO₂CH₃ | H | H | OCH₃ | SePh | SePh | CH | |
| CO₂CH₃ | H | H | OCH₃ | SPh | SPh | CH | 125–127 |
| CO₂CH₃ | H | H | OCH₃ | SePh | SOPh | CH | |
| CO₂CH₃ | H | H | OCH₃ | SePh | SO₂Ph | CH | |
| CO₂CH₃ | H | H | OCH₃ | SCH₃ | SeCH₃ | CH | |
| CO₂CH₃ | H | H | OCH₃ | SCH₃ | SePh | CH | |
| CO₂CH₃ | H | H | OCH₃ | SCH₃ | SPh | CH | |
| CO₂CH₃ | H | H | OCH₃ | SCH₃ | SOPh | CH | |
| CO₂CH₃ | H | H | OCH₃ | SCH₃ | SO₂Ph | CH | |
| CO₂CH₃ | H | H | OCH₃ | SCH₃ | OPh | CH | |
| CO₂CH₃ | H | H | OCH₃ | H | S-(2-CH₃-C₆H₄) | CH | |
| CO₂CH₃ | H | H | OCH₃ | H | S-(2-CF₃-C₆H₄) | CH | |
| CO₂CH₃ | H | H | OCH₃ | H | S-(2-Cl-C₆H₄) | CH | |
| CO₂CH₃ | H | CH₃ | OCH₃ | H | SeCH₃ | CH | |
| CO₂CH₃ | H | CH₃ | OCH₃ | H | SePh | CH | |
| CO₂CH₃ | H | CH₃ | OCH₃ | H | SPh | CH | |
| CO₂CH₃ | H | CH₃ | OCH₃ | H | SO₂Ph | CH | |
| CO₂CH₃ | H | CH₃ | OCH₃ | SeCH₃ | SeCH₃ | CH | |

TABLE 1a-continued

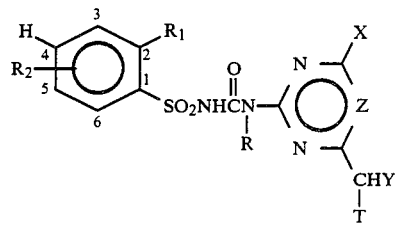

| R₁ | R₂ | R | X | T | Y | Z | m.p. (°C.) |
|---|---|---|---|---|---|---|---|
| $CO_2CH_3$ | H | $CH_3$ | $OCH_3$ | SPh | SPh | CH | |
| $CO_2CH_3$ | H | $CH_3$ | $OCH_3$ | H | OPh | CH | |
| $CO_2CH_3$ | 3-$OCH_3$ | H | $OCH_3$ | H | $SeCH_3$ | CH | |
| $CO_2CH_3$ | 3-$OCH_3$ | H | $OCH_3$ | H | SePh | CH | |
| $CO_2CH_3$ | 3-$OCH_3$ | H | $OCH_3$ | H | SPh | CH | |
| $CO_2CH_3$ | 5-$OCH_3$ | H | $OCH_3$ | H | SOPh | CH | |
| $CO_2CH_3$ | 5-$OCH_3$ | H | $OCH_3$ | H | $SO_2Ph$ | CH | |
| $CO_2CH_3$ | 5-$OCH_3$ | H | $OCH_3$ | H | OPh | CH | |
| $CO_2CH_3$ | 6-$OCH_3$ | H | $OCH_3$ | $SeCH_3$ | $SeCH_3$ | CH | |
| $CO_2CH_3$ | 6-$OCH_3$ | H | $OCH_3$ | $SeCH_3$ | SePh | CH | |
| $CO_2CH_3$ | 6-$OCH_3$ | H | $OCH_3$ | $SeCH_3$ | SPh | CH | |
| $CO_2CH_3$ | 6-$OCH_3$ | H | $OCH_3$ | $SeCH_3$ | $SO_2Ph$ | CH | |
| $CO_2CH_3$ | 3-$CF_3$ | H | $OCH_3$ | H | $SeCH_3$ | CH | |
| $CO_2CH_3$ | 3-$CF_3$ | H | $OCH_3$ | H | SePh | CH | |
| $CO_2CH_3$ | 5-$CF_3$ | H | $OCH_3$ | H | SPh | CH | |
| $CO_2CH_3$ | 5-$CF_3$ | H | $OCH_3$ | H | $SO_2Ph$ | CH | |
| $CO_2CH_3$ | 5-$CF_3$ | H | $OCH_3$ | H | OPh | CH | |
| $CO_2CH_3$ | 6-$CF_3$ | H | $OCH_3$ | SPh | SPh | CH | |
| $CO_2CH_3$ | 3-Cl | H | $OCH_3$ | H | $SeCH_3$ | CH | |
| $CO_2CH_3$ | 3-Cl | H | $OCH_3$ | H | SePh | CH | |
| $CO_2CH_3$ | 3-Cl | H | $OCH_3$ | H | SPh | CH | |
| $CO_2CH_3$ | 5-Cl | H | $OCH_3$ | H | $SO_2Ph$ | CH | |
| $CO_2CH_3$ | 5-Br | H | $OCH_3$ | H | $SeCH_3$ | CH | |
| $CO_2CH_3$ | 5-Br | H | $OCH_3$ | H | SePh | CH | |
| $CO_2CH_3$ | 5-Br | H | $OCH_3$ | H | SPh | CH | |
| $CO_2CH_3$ | 6-F | H | $OCH_3$ | H | $SeCH_3$ | CH | |
| $CO_2CH_3$ | 6-F | H | $OCH_3$ | H | SePh | CH | |
| $CO_2CH_3$ | 3-F | H | $OCH_3$ | H | SPh | CH | |
| $CO_2CH_3$ | 5-F | H | $OCH_3$ | H | SOPh | CH | |
| $CO_2CH_3$ | 6-F | H | $OCH_3$ | H | $SO_2Ph$ | CH | |
| $CO_2CH_3$ | 3-F | H | $OCH_3$ | $SeCH_3$ | $SeCH_3$ | CH | |
| $CO_2CH_3$ | 5-F | H | $OCH_3$ | SePh | SePh | CH | |
| $CO_2CH_3$ | 6-F | H | $OCH_3$ | SPh | SPh | CH | |
| $CO_2CH_3$ | 3-$CH_3$ | H | $OCH_3$ | H | $SeCH_3$ | CH | |
| $CO_2CH_3$ | 5-$CH_3$ | H | $OCH_3$ | H | SPh | CH | |
| $CO_2CH_3$ | H | H | $OCH_3$ | H | $SeCH_3$ | N | |
| $CO_2CH_3$ | H | H | $CH_3$ | H | SePh | N | |
| $CO_2CH_3$ | H | H | Cl | H | OPh | CH | 195–197 |
| $CO_2CH_3$ | H | H | $OCH_3$ | H | SPh | N | |
| $CO_2CH_3$ | H | H | $CH_3$ | H | SOPh | N | |
| $CO_2CH_3$ | H | H | $OCH_3$ | H | $SO_2Ph$ | N | |
| $CO_2CH_3$ | H | H | $CH_3$ | H | OPh | N | |
| $CO_2CH_3$ | H | H | $OCH_3$ | $SeCH_3$ | $SeCH_3$ | N | |
| $CO_2CH_3$ | H | H | $CH_3$ | $SeCH_3$ | SePh | N | |
| $CO_2CH_3$ | H | H | $OCH_3$ | $SeCH_3$ | SPh | N | |
| $CO_2CH_3$ | H | H | $OCH_3$ | $SeCH_3$ | SOPh | N | |
| $CO_2CH_3$ | H | H | $CH_3$ | $SeCH_3$ | $SO_2Ph$ | N | |
| $CO_2CH_3$ | H | H | $OCH_3$ | SePh | $SeCH_3$ | N | |
| $CO_2CH_3$ | H | H | $CH_3$ | SePh | SePh | N | |
| $CO_2CH_3$ | H | H | $OCH_3$ | SePh | SPh | N | |
| $CO_2CH_3$ | H | H | $OCH_3$ | SePh | SOPh | N | |
| $CO_2CH_3$ | H | H | $OCH_3$ | SePh | $SO_2Ph$ | N | |
| $CO_2CH_3$ | H | H | $OCH_3$ | $SCH_3$ | $SeCH_3$ | N | |
| $CO_2CH_3$ | H | H | $OCH_3$ | $SCH_3$ | SePh | N | |
| $CO_2CH_3$ | H | H | $OCH_3$ | $SCH_3$ | SPh | N | |
| $CO_2CH_3$ | H | H | $CH_3$ | $SCH_3$ | SOPh | N | |
| $CO_2CH_3$ | H | H | $CH_3$ | $SCH_3$ | $SO_2Ph$ | N | |
| $CO_2CH_3$ | H | H | $OCH_3$ | $SCH_3$ | OPh | N | |
| $CO_2CH_3$ | H | H | $OCH_3$ | H | 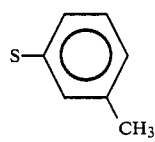 | N | |

TABLE 1a-continued

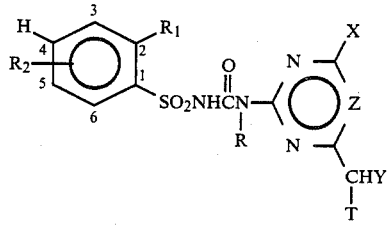

| R₁ | R₂ | R | X | T | Y | Z | m.p. (°C.) |
|---|---|---|---|---|---|---|---|
| CO₂CH₃ | H | H | OCH₃ | H | 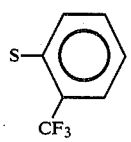 | N | |
| CO₂CH₃ | H | H | OCH₃ | H | 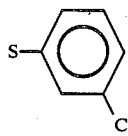 | N | |
| CO₂CH₃ | H | CH₃ | OCH₃ | H | SeCH₃ | N | |
| CO₂CH₃ | H | CH₃ | OCH₃ | H | SePh | N | |
| CO₂CH₃ | H | CH₃ | OCH₃ | H | SPh | N | |
| CO₂CH₃ | H | CH₃ | OCH₃ | H | SO₂Ph | N | |
| CO₂CH₃ | H | CH₃ | OCH₃ | SeCH₃ | SeCH₃ | N | |
| CO₂CH₃ | H | CH₃ | OCH₃ | SPh | SPh | N | |
| CO₂CH₃ | H | CH₃ | OCH₃ | H | OPh | N | |
| CO₂CH₃ | 3-OCH₃ | H | OCH₃ | H | SeCH₃ | N | |
| CO₂CH₃ | 3-OCH₃ | H | OCH₃ | H | SePh | N | |
| CO₂CH₃ | 3-OCH₃ | H | OCH₃ | H | SPh | N | |
| CO₂CH₃ | 5-OCH₃ | H | OCH₃ | H | SOPh | N | |
| CO₂CH₃ | 5-OCH₃ | H | OCH₃ | H | SO₂Ph | N | |
| CO₂CH₃ | 5-OCH₃ | H | OCH₃ | H | OPh | N | |
| CO₂CH₃ | 6-OCH₃ | H | OCH₃ | SeCH₃ | SeCH₃ | N | |
| CO₂CH₃ | 6-OCH₃ | H | OCH₃ | SeCH₃ | SePh | N | |
| CO₂CH₃ | 6-OCH₃ | H | OCH₃ | SeCH₃ | SPh | N | |
| CO₂CH₃ | 6-OCH₃ | H | OCH₃ | SeCH₃ | SO₂Ph | N | |
| CO₂CH₃ | 3-CF₃ | H | OCH₃ | H | SeCH₃ | N | |
| CO₂CH₃ | 3-CF₃ | H | OCH₃ | H | SePh | N | |
| CO₂CH₃ | 5-CF₃ | H | OCH₃ | H | SPh | N | |
| CO₂CH₃ | 5-CF₃ | H | OCH₃ | H | SO₂Ph | N | |
| CO₂CH₃ | 5-CF₃ | H | OCH₃ | H | OPh | N | |
| CO₂CH₃ | 6-CF₃ | H | OCH₃ | SPh | SPh | N | |
| CO₂CH₃ | 3-Cl | H | OCH₃ | H | SeCH₃ | N | |
| CO₂CH₃ | 3-Cl | H | CH₃ | H | SePh | N | |
| CO₂CH₃ | 3-Cl | H | OCH₃ | H | SPh | N | |
| CO₂CH₃ | 5-Cl | H | CH₃ | H | SO₂Ph | N | |
| CO₂CH₃ | 5-Br | H | OCH₃ | H | SeCH₃ | N | |
| CO₂CH₃ | 5-Br | H | CH₃ | H | SePh | N | |
| CO₂CH₃ | 5-Br | H | OCH₃ | H | SPh | N | |
| CO₂CH₃ | 6-F | H | CH₃ | H | SeCH₃ | N | |
| CO₂CH₃ | 6-F | H | OCH₃ | H | SePh | N | |
| CO₂CH₃ | 3-F | H | CH₃ | H | SPh | N | |
| CO₂CH₃ | 5-F | H | OCH₃ | H | SOPh | N | |
| CO₂CH₃ | 6-F | H | CH₃ | H | SO₂Ph | N | |
| CO₂CH₃ | 3-F | H | OCH₃ | SeCH₃ | SeCH₃ | N | |
| CO₂CH₃ | 5-F | H | CH₃ | SePh | SePh | N | |
| CO₂CH₃ | 6-F | H | OCH₃ | SPh | SPh | N | |
| CO₂CH₃ | 3-CH₃ | H | CH₃ | H | SeCH₃ | N | |
| CO₂CH₃ | 5-CH₃ | H | OCH₃ | H | SPh | N | |
| Cl | H | H | OCH₃ | H | SeCH₃ | CH | 134–140 |
| Cl | H | H | OCH₃ | H | SPh | CH | 184–186 |
| Cl | H | H | CH₃ | H | SePh | CH | |
| Cl | H | H | OCH₃ | H | SOPh | CH | 148–152 |
| Cl | H | H | CH₃ | SPh | SPh | CH | |
| Cl | H | H | OCH₂CH₃ | H | SPh | CH | |
| Cl | H | H | OCH₃ | SePh | SePh | CH | |
| Cl | H | H | Br | H | SePh | CH | |
| Cl | H | H | OCH₃ | H | OPh | CH | 196–198 |
| Cl | H | H | OCH₃ | SeCH₃ | SeCH₃ | CH | |
| Cl | H | H | OCH₃ | H | SPh | N | |
| Cl | H | H | OCF₂H | H | SPh | CH | |
| Cl | H | H | OCH₃ | SCH₃ | SeCH₃ | CH | |

TABLE 1a-continued

| R₁ | R₂ | R | X | T | Y | Z | m.p. (°C.) |
|---|---|---|---|---|---|---|---|
| Cl | H | H | OCH₃ | SPh | SPh | N | |
| Cl | H | H | CH₃ | SCH₃ | SeCH₃ | N | |
| Cl | H | H | F | H | SPh | CH | |
| Cl | H | H | OCH₃ | SPh | SPh | CH | 174–175.5 |
| Cl | H | H | CF₃ | H | SeCH₃ | CH | |
| Cl | H | H | CF₃ | H | SPh | CH | |
| Cl | H | H | OCH₃ | H | OPh | N | |
| Cl | H | H | OCH₂CH₃ | H | SeCH₃ | N | |
| Cl | H | H | OCH₂CH₃ | SeCH₃ | SeCH₃ | CH | |
| Cl | H | CH₃ | OCH₃ | H | SPh | CH | |
| Cl | 5-OCH₃ | H | OCH₃ | H | SPh | CH | |
| Cl | 5-CF₃ | H | OCH₃ | H | SPh | CH | |
| Cl | 3-F | H | OCH₃ | H | SePh | CH | |
| SO₂N(CH₃)₂ | H | H | OCH₃ | H | SeCH₃ | CH | |
| SO₂N(CH₃)₂ | H | H | OCH₃ | H | SPh | CH | 166–168 |
| SO₂N(CH₃)₂ | H | H | CH₃ | H | SePh | CH | |
| SO₂N(CH₃)₂ | H | H | OCH₃ | H | SO₂Ph | CH | |
| SO₂N(CH₃)₂ | H | H | CH₃ | SPh | SPh | CH | |
| SO₂N(CH₃)₂ | H | H | OCH₂CH₃ | H | SPh | CH | |
| SO₂N(CH₃)₂ | H | H | OCH₃ | SePh | SePh | CH | |
| SO₂N(CH₃)₂ | H | H | Br | H | SePh | CH | |
| SO₂N(CH₃)₂ | H | H | OCH₃ | H | OPh | CH | 222–224 |
| SO₂N(CH₃)₂ | H | H | OCH₃ | SeCH₃ | SeCH₃ | CH | |
| SO₂N(CH₃)₂ | H | H | OCH₃ | H | SPh | N | |
| SO₂N(CH₃)₂ | H | H | OCF₂H | H | SPh | CH | |
| SO₂N(CH₃)₂ | H | H | OCH₃ | SCH₃ | SeCH₃ | CH | |
| SO₂N(CH₃)₂ | H | H | OCH₃ | SPh | SPh | N | |
| SO₂N(CH₃)₂ | H | H | CH₃ | SCH₃ | SeCH₃ | N | |
| SO₂N(CH₃)₂ | H | H | F | H | SPh | CH | |
| SO₂N(CH₃)₂ | H | H | OCH₃ | SPh | SPh | CH | |
| SO₂N(CH₃)₂ | H | H | CF₃ | H | SeCH₃ | CH | |
| SO₂N(CH₃)₂ | H | H | CF₃ | H | SPh | CH | |
| SO₂N(CH₃)₂ | H | H | OCH₃ | H | OPh | N | |
| SO₂N(CH₃)₂ | H | H | OCH₂CH₃ | H | SeCH₃ | N | |
| SO₂N(CH₃)₂ | H | H | OCH₂CH₃ | SeCH₃ | SeCH₃ | CH | |
| SO₂N(CH₃)₂ | H | CH₃ | OCH₃ | H | SPh | CH | |
| SO₂N(CH₃)₂ | 5-OCH₃ | H | OCH₃ | H | SPh | CH | |
| SO₂N(CH₃)₂ | 5-CF₃ | H | OCH₃ | H | SPh | CH | |
| SO₂N(CH₃)₂ | 3-F | H | OCH₃ | H | SePh | CH | |
| NO₂ | H | H | OCH₃ | H | SeCH₃ | CH | |
| NO₂ | H | H | OCH₃ | H | SPh | CH | |
| NO₂ | H | H | CH₃ | H | SePh | CH | |
| NO₂ | H | H | OCH₃ | H | SO₂Ph | CH | |
| NO₂ | H | H | CH₃ | SPh | SPh | CH | |
| NO₂ | H | H | OCH₂CH₃ | H | SPh | CH | |
| NO₂ | H | H | OCH₃ | SePh | SePh | CH | |
| NO₂ | H | H | Br | H | SePh | CH | |
| NO₂ | H | H | OCH₃ | H | OPh | CH | |
| NO₂ | H | H | OCH₃ | SeCH₃ | SeCH₃ | CH | |
| NO₂ | H | H | OCH₃ | H | SPh | N | |
| NO₂ | H | H | OCF₂H | H | SPh | CH | |
| NO₂ | H | H | OCH₃ | SCH₃ | SeCH₃ | CH | |
| NO₂ | H | H | OCH₃ | SPh | SPh | N | |
| NO₂ | H | H | CH₃ | SCH₃ | SeCH₃ | N | |
| NO₂ | H | H | F | H | SPh | CH | |
| NO₂ | H | H | OCH₃ | SPh | SPh | CH | |
| NO₂ | H | H | CF₃ | H | SeCH₃ | CH | |
| NO₂ | H | H | CF₃ | H | SPh | CH | |
| NO₂ | H | H | OCH₃ | H | OPh | N | |
| NO₂ | H | H | OCH₂CH₃ | H | SeCH₃ | N | |
| NO₂ | H | H | OCH₂CH₃ | SeCH₃ | SeCH₃ | CH | |
| NO₂ | H | CH₃ | OCH₃ | H | SPh | CH | |
| NO₂ | 5-OCH₃ | H | OCH₃ | H | SPh | CH | |
| NO₂ | 5-CF₃ | H | OCH₃ | H | SPh | CH | |
| NO₂ | 3-F | H | OCH₃ | H | SePh | CH | |
| SO₂CH₃ | H | H | OCH₃ | H | SeCH₃ | CH | |
| SO₂CH₃ | H | H | OCH₃ | H | SPh | CH | |
| SO₂CH₃ | H | H | CH₃ | H | SePh | CH | |
| SO₂CH₃ | H | H | OCH₃ | H | SO₂Ph | CH | |

TABLE 1a-continued

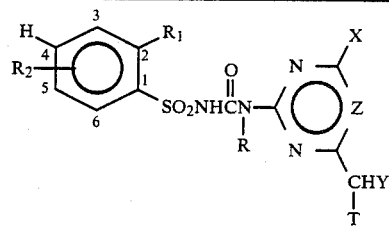

| R₁ | R₂ | R | X | T | Y | Z | m.p. (°C.) |
|---|---|---|---|---|---|---|---|
| SO₂CH₃ | H | H | CH₃ | SPh | SPh | CH | |
| SO₂CH₃ | H | H | OCH₂CH₃ | H | SPh | CH | |
| SO₂CH₃ | H | H | OCH₃ | SePh | SePh | CH | |
| SO₂CH₃ | H | H | Br | H | SePh | CH | |
| SO₂CH₃ | H | H | OCH₃ | H | OPh | CH | |
| SO₂CH₃ | H | H | OCH₃ | SeCH₃ | SeCH₃ | CH | |
| SO₂CH₃ | H | H | OCH₃ | H | SPh | N | |
| SO₂CH₃ | H | H | OCF₂H | H | SPh | CH | |
| SO₂CH₃ | H | H | OCH₃ | SCH₃ | SeCH₃ | CH | |
| SO₂CH₃ | H | H | OCH₃ | SPh | SPh | N | |
| SO₂CH₃ | H | H | CH₃ | SCH₃ | SeCH₃ | N | |
| SO₂CH₃ | H | H | F | H | SPh | CH | |
| SO₂CH₃ | H | H | OCH₃ | SPh | SPh | CH | |
| SO₂CH₃ | H | H | CF₃ | H | SeCH₃ | CH | |
| SO₂CH₃ | H | H | CF₃ | H | SPh | CH | |
| SO₂CH₃ | H | H | OCH₃ | H | OPh | N | |
| SO₂CH₃ | H | H | OCH₂CH₃ | H | SeCH₃ | N | |
| SO₂CH₃ | H | H | OCH₂CH₃ | SeCH₃ | SeCH₃ | CH | |
| SO₂CH₃ | H | CH₃ | OCH₃ | H | SPh | CH | |
| SO₂CH₃ | 5-OCH₃ | H | OCH₃ | H | SPh | CH | |
| SO₂CH₃ | 5-CF₃ | H | OCH₃ | H | SPh | CH | |
| SO₂CH₃ | 3-F | H | OCH₃ | H | SePh | CH | |
| CF₃ | H | H | OCH₃ | H | SeCH₃ | CH | |
| CF₃ | H | H | OCH₃ | H | SPh | CH | |
| CF₃ | H | H | CH₃ | H | SePh | CH | |
| CF₃ | H | H | OCH₃ | H | SO₂Ph | CH | |
| CF₃ | H | H | CH₃ | SPh | SPh | CH | |
| CF₃ | H | H | OCH₂CH₃ | H | SPh | CH | |
| CF₃ | H | H | OCH₃ | SePh | SePh | CH | |
| CF₃ | H | H | Br | H | SePh | CH | |
| CF₃ | H | H | OCH₃ | H | OPh | CH | |
| CF₃ | H | H | OCH₃ | SeCH₃ | SeCH₃ | CH | |
| CF₃ | H | H | OCH₃ | H | SPh | N | |
| CF₃ | H | H | OCF₂H | H | SPh | CH | |
| CF₃ | H | H | OCH₃ | SCH₃ | SeCH₃ | CH | |
| CF₃ | H | H | OCH₃ | SPh | SPh | N | |
| CF₃ | H | H | CH₃ | SCH₃ | SeCH₃ | N | |
| CF₃ | H | H | F | H | SPh | CH | |
| CF₃ | H | H | OCH₃ | SPh | SPh | CH | |
| CF₃ | H | H | CF₃ | H | SeCH₃ | CH | |
| CF₃ | H | H | CF₃ | H | SPh | CH | |
| CF₃ | H | H | OCH₃ | H | OPh | N | |
| CF₃ | H | H | OCH₂CH₃ | H | SeCH₃ | N | |
| CF₃ | H | H | OCH₂CH₃ | SeCH₃ | SeCH₃ | CH | |
| CF₃ | H | CH₃ | OCH₃ | H | SPh | CH | |
| CF₃ | 5-OCH₃ | H | OCH₃ | H | SPh | CH | |
| CF₃ | 3-CF₃ | H | OCH₃ | H | SPh | CH | |
| CF₃ | 6-F | H | OCH₃ | H | SePh | CH | |
| CH₃ | H | H | OCH₃ | H | SeCH₃ | CH | |
| CH₃ | H | H | OCH₃ | H | SPh | CH | |
| CH₃ | H | H | CH₃ | H | SePh | CH | |
| CH₃ | H | H | OCH₃ | H | SO₂Ph | CH | |
| CH₃ | H | H | CH₃ | SPh | SPh | CH | |
| CH₃ | H | H | OCH₂CH₃ | H | SPh | CH | |
| CH₃ | H | H | OCH₃ | SePh | SePh | CH | |
| CH₃ | H | H | Br | H | SePh | CH | |
| CH₃ | H | H | OCH₃ | H | OPh | CH | |
| CH₃ | H | H | OCH₃ | SeCH₃ | SeCH₃ | CH | |
| CH₃ | H | H | OCH₃ | H | SPh | N | |
| CH₃ | H | H | OCF₂H | H | SPh | CH | |
| CH₃ | H | H | OCH₃ | SCH₃ | SeCH₃ | CH | |
| CH₃ | H | H | OCH₃ | SPh | SPh | N | |
| CH₃ | H | H | CH₃ | SCH₃ | SeCH₃ | N | |
| CH₃ | H | H | F | H | SPh | CH | |
| CH₃ | H | H | OCH₃ | SPh | SPh | CH | |
| CH₃ | H | H | CF₃ | H | SeCH₃ | CH | |
| CH₃ | H | H | CF₃ | H | SPh | CH | |
| CH₃ | H | H | OCH₃ | H | OPh | N | |
| CH₃ | H | H | OCH₂CH₃ | H | SeCH₃ | N | |

TABLE 1a-continued

| R₁ | R₂ | R | X | T | Y | Z | m.p. (°C.) |
|---|---|---|---|---|---|---|---|
| CH₃ | H | H | OCH₂CH₃ | SeCH₃ | SeCH₃ | CH | |
| CH₃ | H | CH₃ | OCH₃ | H | SPh | CH | |
| CH₃ | 3-OCH₃ | H | OCH₃ | H | SPh | CH | |
| CH₃ | 5-CF₃ | H | OCH₃ | H | SPh | CH | |
| CH₃ | 6-F | H | OCH₃ | H | SePh | CH | |
| OCH₂C≡CH | H | H | OCH₃ | H | SeCH₃ | CH | |
| OCH₂C≡CH | H | H | OCH₃ | H | SPh | CH | |
| OCH₂C≡CH | H | H | CH₃ | H | SePh | CH | |
| OCH₂C≡CH | H | H | OCH₃ | H | SO₂Ph | CH | |
| OCH₂C≡CH | H | H | CH₃ | SPh | SPh | CH | |
| OCH₂C≡CH | H | H | OCH₂CH₃ | H | SPh | CH | |
| OCH₂C≡CH | H | H | OCH₃ | SePh | SePh | CH | |
| OCH₂C≡CH | H | H | Br | H | SePh | CH | |
| OCH₂C≡CH | H | H | OCH₃ | H | OPh | CH | |
| OCH₂C≡CH | H | H | OCH₃ | SeCH₃ | SeCH₃ | CH | |
| OCH₂C≡CH | H | H | OCH₃ | H | SPh | N | |
| OCH₂C≡CH | H | H | OCF₂H | H | SPh | CH | |
| OCH₂C≡CH | H | H | OCH₃ | SCH₃ | SeCH₃ | CH | |
| OCH₂C≡CH | H | H | OCH₃ | SPh | SPh | N | |
| OCH₂C≡CH | H | H | CH₃ | SCH₃ | SeCH₃ | N | |
| OCH₂C≡CH | H | H | F | H | SPh | CH | |
| OCH₂C≡CH | H | H | OCH₃ | SPh | SPh | CH | |
| OCH₂C≡CH | H | H | CF₃ | H | SeCH₃ | CH | |
| OCH₂C≡CH | H | H | CF₃ | H | SPh | CH | |
| OCH₂C≡CH | H | H | OCH₃ | H | OPh | N | |
| OCH₂C≡CH | H | H | OCH₂CH₃ | H | SeCH₃ | N | |
| OCH₂C≡CH | H | H | OCH₂CH₃ | SeCH₃ | SeCH₃ | CH | |
| OCH₂C≡CH | H | CH₃ | OCH₃ | H | SPh | CH | |
| OCH₂C≡CH | 3-OCH₃ | H | OCH₃ | H | SPh | CH | |
| OCH₂C≡CH | 5-CF₃ | H | OCH₃ | H | SPh | CH | |
| OCH₂C≡CH | 6-F | H | OCH₃ | H | SePh | CH | |
| OCH₂—CH=CH₂ | H | H | OCH₃ | H | SeCH₃ | CH | |
| OCH₂—CH=CH₂ | H | H | OCH₃ | H | SPh | CH | |
| OCH₂—CH=CH₂ | H | H | CH₃ | H | SePh | CH | |
| OCH₂—CH=CH₂ | H | H | OCH₃ | H | SO₂Ph | CH | |
| OCH₂—CH=CH₂ | H | H | CH₃ | SPh | SPh | CH | |
| OCH₂—CH=CH₂ | H | H | OCH₂CH₃ | H | SPh | CH | |
| OCH₂—CH=CH₂ | H | H | OCH₃ | SePh | SePh | CH | |
| OCH₂—CH=CH₂ | H | H | Br | H | SePh | CH | |
| OCH₂—CH=CH₂ | H | H | OCH₃ | H | OPh | CH | |
| OCH₂—CH=CH₂ | H | H | OCH₃ | SeCH₃ | SeCH₃ | CH | |
| OCH₂—CH=CH₂ | H | H | OCH₃ | H | SPh | N | |
| OCH₂—CH=CH₂ | H | H | OCF₂H | H | SPh | CH | |
| OCH₂—CH=CH₂ | H | H | OCH₃ | SCH₃ | SeCH₃ | CH | |
| OCH₂—CH=CH₂ | H | H | OCH₃ | SPh | SPh | N | |
| OCH₂—CH=CH₂ | H | H | CH₃ | SCH₃ | SeCH₃ | N | |
| OCH₂—CH=CH₂ | H | H | F | H | SPh | CH | |
| OCH₂—CH=CH₂ | H | H | OCH₃ | SPh | SPh | CH | |
| OCH₂—CH=CH₂ | H | H | CF₃ | H | SeCH₃ | CH | |
| OCH₂—CH=CH₂ | H | H | CF₃ | H | SPh | CH | |
| OCH₂—CH=CH₂ | H | H | OCH₃ | H | OPh | N | |
| OCH₂—CH=CH₂ | H | H | OCH₂CH₃ | H | SeCH₃ | N | |
| OCH₂—CH=CH₂ | H | H | OCH₂CH₃ | SeCH₃ | SeCH₃ | CH | |
| OCH₂—CH=CH₂ | H | CH₃ | OCH₃ | H | SPh | CH | |
| OCH₂—CH=CH₂ | 3-OCH₃ | H | OCH₃ | H | SPh | CH | |
| OCH₂—CH=CH₂ | 6-CF₃ | H | OCH₃ | H | SPh | CH | |
| OCH₂—CH=CH₂ | 5-F | H | OCH₃ | H | SePh | CH | |
| OCF₃ | H | H | OCH₃ | H | SeCH₃ | CH | |
| OCF₃ | H | H | OCH₃ | H | SPh | CH | |
| OCF₃ | H | H | CH₃ | H | SePh | CH | |
| OCF₃ | H | H | OCH₃ | H | SO₂Ph | CH | |
| OCF₃ | H | H | CH₃ | SPh | SPh | CH | |
| OCF₃ | H | H | OCH₂CH₃ | H | SPh | CH | |
| OCF₃ | H | H | OCH₃ | SePh | SePh | CH | |
| OCF₃ | H | H | Br | H | SePh | CH | |
| OCF₃ | H | H | OCH₃ | H | OPh | CH | |
| OCF₃ | H | H | OCH₃ | SeCH₃ | SeCH₃ | CH | |
| OCF₃ | H | H | OCH₃ | H | SPh | N | |
| OCF₃ | H | H | OCF₂H | H | SPh | CH | |

TABLE 1a-continued

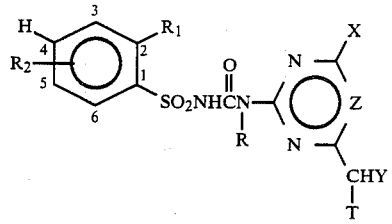

| R₁ | R₂ | R | X | T | Y | Z | m.p. (°C.) |
|---|---|---|---|---|---|---|---|
| OCF₃ | H | H | OCH₃ | SCH₃ | SeCH₃ | CH | |
| OCF₃ | H | H | OCH₃ | SPh | SPh | N | |
| OCF₃ | H | H | CH₃ | SCH₃ | SeCH₃ | N | |
| OCF₃ | H | H | F | H | SPh | CH | |
| OCF₃ | H | H | OCH₃ | SPh | SPh | CH | |
| OCF₃ | H | H | CF₃ | H | SeCH₃ | CH | |
| OCF₃ | H | H | CF₃ | H | SPh | CH | |
| OCF₃ | H | H | OCH₃ | H | OPh | N | |
| OCF₃ | H | H | OCH₂CH₃ | H | SeCH₃ | N | |
| OCF₃ | H | H | OCH₂CH₃ | SeCH₃ | SeCH₃ | CH | |
| OCF₃ | H | CH₃ | OCH₃ | H | SPh | CH | |
| OCF₃ | 3-OCH₃ | H | OCH₃ | H | SPh | CH | |
| OCF₃ | 6-CF₃ | H | OCH₃ | H | SPh | CH | |
| OCF₃ | 5-F | H | OCH₃ | H | SePh | CH | |
| OCHF₂ | H | H | OCH₃ | H | SeCH₃ | CH | |
| OCHF₂ | H | H | OCH₃ | H | SPh | CH | |
| OCHF₂ | H | H | CH₃ | H | SePh | CH | |
| OCHF₂ | H | H | OCH₃ | H | SO₂Ph | CH | |
| OCHF₂ | H | H | CH₃ | SPh | SPh | CH | |
| OCHF₂ | H | H | OCH₂CH₃ | H | SPh | CH | |
| OCHF₂ | H | H | OCH₃ | SePh | SePh | CH | |
| OCHF₂ | H | H | Br | H | SePh | CH | |
| OCHF₂ | H | H | OCH₃ | H | OPh | CH | |
| OCHF₂ | H | H | OCH₃ | SeCH₃ | SeCH₃ | CH | |
| OCHF₂ | H | H | OCH₃ | H | SPh | N | |
| OCHF₂ | H | H | OCF₂H | H | SPh | CH | |
| OCHF₂ | H | H | OCH₃ | SCH₃ | SeCH₃ | CH | |
| OCHF₂ | H | H | OCH₃ | SPh | SPh | N | |
| OCHF₂ | H | H | CH₃ | SCH₃ | SeCH₃ | N | |
| OCHF₂ | H | H | F | H | SPh | CH | |
| OCHF₂ | H | H | OCH₃ | SPh | SPh | CH | |
| OCHF₂ | H | H | CF₃ | H | SeCH₃ | CH | |
| OCHF₂ | H | H | CF₃ | H | SPh | CH | |
| OCHF₂ | H | H | OCH₃ | H | OPh | N | |
| OCHF₂ | H | H | OCH₂CH₃ | H | SeCH₃ | N | |
| OCHF₂ | H | H | OCH₂CH₃ | SeCH₃ | SeCH₃ | CH | |
| OCHF₂ | H | CH₃ | OCH₃ | H | SPh | CH | |
| OCHF₂ | 3-OCH₃ | H | OCH₃ | H | SPh | CH | |
| OCHF₂ | 5-CF₃ | H | OCH₃ | H | SPh | CH | |
| OCHF₂ | 6-F | H | OCH₃ | H | SePh | CH | |
| SCHF₂ | H | H | OCH₃ | H | SeCH₃ | CH | |
| SCHF₂ | H | H | OCH₃ | H | SPh | CH | |
| SCHF₂ | H | H | CH₃ | H | SePh | CH | |
| SCHF₂ | H | H | OCH₃ | H | SO₂Ph | CH | |
| SCHF₂ | H | H | CH₃ | SPh | SPh | CH | |
| SCHF₂ | H | H | OCH₂CH₃ | H | SPh | CH | |
| SCHF₂ | H | H | OCH₃ | SePh | SePh | CH | |
| SCHF₂ | H | H | Br | H | SePh | CH | |
| SCHF₂ | H | H | OCH₃ | H | OPh | CH | |
| SCHF₂ | H | H | OCH₃ | SeCH₃ | SeCH₃ | CH | |
| SCHF₂ | H | H | OCH₃ | H | SPh | N | |
| SCHF₂ | H | H | OCF₂H | H | SPh | CH | |
| SCHF₂ | H | H | OCH₃ | SCH₃ | SeCH₃ | CH | |
| SCHF₂ | H | H | OCH₃ | SPh | SPh | N | |
| SCHF₂ | H | H | CH₃ | SCH₃ | SeCH₃ | N | |
| SCHF₂ | H | H | F | H | SPh | CH | |
| SCHF₂ | H | H | OCH₃ | SPh | SPh | CH | |
| SCHF₂ | H | H | CF₃ | H | SeCH₃ | CH | |
| SCHF₂ | H | H | CF₃ | H | SPh | CH | |
| SCHF₂ | H | H | OCH₃ | H | OPh | N | |
| SCHF₂ | H | H | OCH₂CH₃ | H | SeCH₃ | N | |
| SCHF₂ | H | H | OCH₂CH₃ | SeCH₃ | SeCH₃ | CH | |
| SCHF₂ | H | CH₃ | OCH₃ | H | SPh | CH | |
| SCHF₂ | 3-OCH₃ | H | OCH₃ | H | SPh | CH | |
| SCHF₂ | 5-CF₃ | H | OCH₃ | H | SPh | CH | |
| SCHF₂ | 6-F | H | OCH₃ | H | SePh | CH | |
| SCH₃ | H | H | OCH₃ | H | SeCH₃ | CH | |
| SCH₃ | H | H | OCH₃ | H | SPh | CH | |
| SCH₃ | H | H | CH₃ | H | SePh | CH | |

TABLE 1a-continued

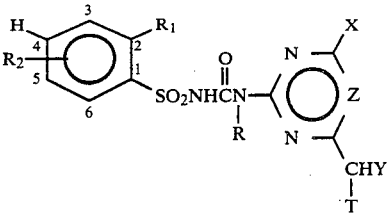

| R₁ | R₂ | R | X | T | Y | Z | m.p. (°C.) |
|---|---|---|---|---|---|---|---|
| SCH₃ | H | H | OCH₃ | H | SO₂Ph | CH | |
| SCH₃ | H | H | CH₃ | SPh | SPh | CH | |
| SCH₃ | H | H | OCH₂CH₃ | H | SPh | CH | |
| SCH₃ | H | H | OCH₃ | SePh | SePh | CH | |
| SCH₃ | H | H | Br | H | SePh | CH | |
| SCH₃ | H | H | OCH₃ | H | OPh | CH | |
| SCH₃ | H | H | OCH₃ | SeCH₃ | SeCH₃ | CH | |
| SCH₃ | H | H | OCH₃ | H | SPh | N | |
| SCH₃ | H | H | OCF₂H | H | SPh | CH | |
| SCH₃ | H | H | OCH₃ | SCH₃ | SeCH₃ | CH | |
| SCH₃ | H | H | OCH₃ | SPh | SPh | N | |
| SCH₃ | H | H | CH₃ | SCH₃ | SeCH₃ | N | |
| SCH₃ | H | H | F | H | SPh | CH | |
| SCH₃ | H | H | OCH₃ | SPh | SPh | CH | |
| SCH₃ | H | H | CF₃ | H | SeCH₃ | CH | |
| SCH₃ | H | H | CF₃ | H | SPh | CH | |
| SCH₃ | H | H | OCH₃ | H | OPh | N | |
| SCH₃ | H | H | OCH₂CH₃ | H | SeCH₃ | N | |
| SCH₃ | H | H | OCH₂CH₃ | SeCH₃ | SeCH₃ | CH | |
| SCH₃ | H | CH₃ | OCH₃ | H | SPh | CH | |
| SCH₃ | 3-OCH₃ | H | OCH₃ | H | SPh | CH | |
| SCH₃ | 5-CF₃ | H | OCH₃ | H | SPh | CH | |
| SCH₃ | 6-F | H | OCH₃ | H | SePh | CH | |
| CO₂CH₂CH₃ | H | H | OCH₃ | H | SeCH₃ | CH | |
| CO₂CH₂CH₃ | H | H | OCH₃ | H | SPh | CH | 105–109 |
| CO₂CH₂CH₃ | H | H | CH₃ | H | SePh | CH | |
| CO₂CH₂CH₃ | H | H | OCH₃ | H | SO₂Ph | CH | |
| CO₂CH₂CH₃ | H | H | CH₃ | SPh | SPh | CH | |
| CO₂CH₂CH₃ | H | H | OCH₂CH₃ | H | SPh | CH | |
| CO₂CH₂CH₃ | H | H | OCH₃ | SePh | SePh | CH | |
| CO₂CH₂CH₃ | H | H | Br | H | SePh | CH | |
| CO₂CH₂CH₃ | H | H | OCH₃ | H | OPh | CH | |
| CO₂CH₂CH₃ | H | H | OCH₃ | SeCH₃ | SeCH₃ | CH | |
| CO₂CH₂CH₃ | H | H | OCH₃ | H | SPh | N | |
| CO₂CH₂CH₃ | H | H | OCF₂H | H | SPh | CH | |
| CO₂CH₂CH₃ | H | H | OCH₃ | SCH₃ | SeCH₃ | CH | |
| CO₂CH₂CH₃ | H | H | OCH₃ | SPh | SPh | N | |
| CO₂CH₂CH₃ | H | H | CH₃ | SCH₃ | SeCH₃ | N | |
| CO₂CH₂CH₃ | H | H | F | H | SPh | CH | |
| CO₂CH₂CH₃ | H | H | OCH₃ | SPh | SPh | CH | |
| CO₂CH₂CH₃ | H | H | CF₃ | H | SeCH₃ | CH | |
| CO₂CH₂CH₃ | H | H | CF₃ | H | SPh | CH | |
| CO₂CH₂CH₃ | H | H | OCH₃ | H | OPh | N | |
| CO₂CH₂CH₃ | H | H | OCH₂CH₃ | H | SeCH₃ | N | |
| CO₂CH₂CH₃ | H | H | OCH₂CH₃ | SeCH₃ | SeCH₃ | CH | |
| CO₂CH₂CH₃ | H | CH₃ | OCH₃ | H | SPh | CH | |
| CO₂CH₂CH₃ | 3-OCH₃ | H | OCH₃ | H | SPh | CH | |
| CO₂CH₂CH₃ | 5-CF₃ | H | OCH₃ | H | SPh | CH | |
| CO₂CH₂CH₃ | 6-F | H | OCH₃ | H | SePh | CH | |
| OCH₂CH₂OCH₃ | H | H | OCH₃ | H | SeCH₃ | CH | |
| OCH₂CH₂OCH₃ | H | H | OCH₃ | H | SPh | CH | |
| OCH₂CH₂OCH₃ | H | H | CH₃ | H | SePh | CH | |
| OCH₂CH₂OCH₃ | H | H | OCH₃ | H | SO₂Ph | CH | |
| OCH₂CH₂OCH₃ | H | H | CH₃ | SPh | SPh | CH | |
| OCH₂CH₂OCH₃ | H | H | OCH₂CH₃ | H | SPh | CH | |
| OCH₂CH₂OCH₃ | H | H | OCH₃ | SePh | SePh | CH | |
| OCH₂CH₂OCH₃ | H | H | Br | H | SePh | CH | |
| OCH₂CH₂OCH₃ | H | H | OCH₃ | H | OPh | CH | |
| OCH₂CH₂OCH₃ | H | H | OCH₃ | SeCH₃ | SeCH₃ | CH | |
| OCH₂CH₂OCH₃ | H | H | OCH₃ | H | SPh | N | |
| OCH₂CH₂OCH₃ | H | H | OCF₂H | H | SPh | CH | |
| OCH₂CH₂OCH₃ | H | H | OCH₃ | SCH₃ | SeCH₃ | CH | |
| OCH₂CH₂OCH₃ | H | H | OCH₃ | SPh | SPh | N | |
| OCH₂CH₂OCH₃ | H | H | CH₃ | SCH₃ | SeCH₃ | N | |
| OCH₂CH₂OCH₃ | H | H | F | H | SPh | CH | |
| OCH₂CH₂OCH₃ | H | H | OCH₃ | SPh | SPh | CH | |
| OCH₂CH₂OCH₃ | H | H | CF₃ | H | SeCH₃ | CH | |
| OCH₂CH₂OCH₃ | H | H | CF₃ | H | SPh | CH | |
| OCH₂CH₂OCH₃ | H | H | OCH₃ | H | OPh | N | |

TABLE 1a-continued

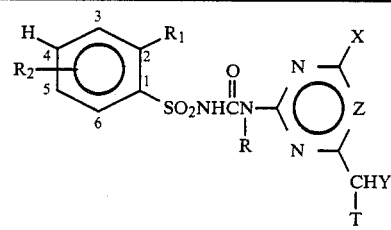

| R₁ | R₂ | R | X | T | Y | Z | m.p. (°C.) |
|---|---|---|---|---|---|---|---|
| OCH₂CH₂OCH₃ | H | H | OCH₂CH₃ | H | SeCH₃ | N | |
| OCH₂CH₂OCH₃ | H | H | OCH₂CH₃ | SeCH₃ | SeCH₃ | CH | |
| OCH₂CH₂OCH₃ | H | CH₃ | OCH₃ | H | SPh | CH | |
| OCH₂CH₂OCH₃ | 3-OCH₃ | H | OCH₃ | H | SPh | CH | |
| OCH₂CH₂OCH₃ | 5-CF₃ | H | OCH₃ | H | SPh | CH | |
| OCH₂CH₂OCH₃ | 6-F | H | OCH₃ | H | SePh | CH | |
| Br | H | H | OCH₃ | H | SeCH₃ | CH | |
| Br | H | H | OCH₃ | H | SPh | CH | |
| Br | H | H | CH₃ | H | SePh | CH | |
| Br | H | H | OCH₃ | H | SO₂Ph | CH | |
| Br | H | H | CH₃ | SPh | SPh | CH | |
| Br | H | H | OCH₂CH₃ | H | SPh | CH | |
| Br | H | H | OCH₃ | SePh | SePh | CH | |
| Br | H | H | Br | H | SePh | CH | |
| Br | H | H | OCH₃ | H | OPh | CH | |
| Br | H | H | OCH₃ | SeCH₃ | SeCH₃ | CH | |
| Br | H | H | OCH₃ | H | SPh | N | |
| Br | H | H | OCF₂H | H | SPh | CH | |
| Br | H | H | OCH₃ | SCH₃ | SeCH₃ | CH | |
| Br | H | H | OCH₃ | SPh | SPh | N | |
| Br | H | H | CH₃ | SCH₃ | SeCH₃ | N | |
| Br | H | H | F | H | SPh | CH | |
| Br | H | H | OCH₃ | SPh | SPh | CH | |
| Br | H | H | CF₃ | H | SeCH₃ | CH | |
| Br | H | H | CF₃ | H | SPh | CH | |
| Br | H | H | OCH₃ | H | OPh | N | |
| Br | H | H | OCH₂CH₃ | H | SeCH₃ | N | |
| Br | H | H | OCH₂CH₃ | SeCH₃ | SeCH₃ | CH | |
| Br | H | CH₃ | OCH₃ | H | SPh | CH | |
| Br | 3-OCH₃ | H | OCH₃ | H | SPh | CH | |
| Br | 5-CF₃ | H | OCH₃ | H | SPh | CH | |
| Br | 6-F | H | OCH₃ | H | SePh | CH | |
| OCH₃ | H | H | OCH₃ | H | SeCH₃ | CH | |
| OCH₃ | H | H | OCH₃ | H | SPh | CH | |
| OCH₃ | H | H | CH₃ | H | SePh | CH | |
| OCH₃ | H | H | OCH₃ | H | SO₂Ph | CH | |
| OCH₃ | H | H | CH₃ | SPh | SPh | CH | |
| OCH₃ | H | H | OCH₂CH₃ | H | SPh | CH | |
| OCH₃ | H | H | OCH₃ | SePh | SePh | CH | |
| OCH₃ | H | H | Br | H | SePh | CH | |
| OCH₃ | H | H | OCH₃ | H | OPh | CH | |
| OCH₃ | H | H | OCH₃ | SeCH₃ | SeCH₃ | CH | |
| OCH₃ | H | H | OCH₃ | H | SPh | N | |
| OCH₃ | H | H | OCF₂H | H | SPh | CH | |
| OCH₃ | H | H | OCH₃ | SCH₃ | SeCH₃ | CH | |
| OCH₃ | H | H | OCH₃ | SPh | SPh | N | |
| OCH₃ | H | H | CH₃ | SCH₃ | SeCH₃ | N | |
| OCH₃ | H | H | F | H | SPh | CH | |
| OCH₃ | H | H | OCH₃ | SPh | SPh | CH | |
| OCH₃ | H | H | CF₃ | H | SeCH₃ | CH | |
| OCH₃ | H | H | CF₃ | H | SPh | CH | |
| OCH₃ | H | H | OCH₃ | H | OPh | N | |
| OCH₃ | H | H | OCH₂CH₃ | H | SeCH₃ | N | |
| OCH₃ | H | H | OCH₂CH₃ | SeCH₃ | SeCH₃ | CH | |
| OCH₃ | H | CH₃ | OCH₃ | H | SPh | CH | |
| OCH₃ | 3-OCH₃ | H | OCH₃ | H | SPh | CH | |
| OCH₃ | 5-CF₃ | H | OCH₃ | H | SPh | CH | |
| OCH₃ | 6-F | H | OCH₃ | H | SePh | CH | |
| CH(OCH₃)CH₃ | H | H | OCH₃ | H | SeCH₃ | CH | |
| CH(OCH₃)CH₃ | H | H | OCH₃ | H | SPh | CH | |
| CH(OCH₃)CH₃ | H | H | CH₃ | H | SePh | CH | |
| CH(OCH₃)CH₃ | H | H | OCH₃ | H | SO₂Ph | CH | |
| CH(OCH₃)CH₃ | H | H | CH₃ | SPh | SPh | CH | |
| CH(OCH₃)CH₃ | H | H | OCH₂CH₃ | H | SPh | CH | |
| CH(OCH₃)CH₃ | H | H | OCH₃ | SePh | SePh | CH | |
| CH(OCH₃)CH₃ | H | H | Br | H | SePh | CH | |
| CH(OCH₃)CH₃ | H | H | OCH₃ | H | OPh | CH | |
| CH(OCH₃)CH₃ | H | H | OCH₃ | SeCH₃ | SeCH₃ | CH | |
| CH(OCH₃)CH₃ | H | H | OCH₃ | H | SPh | N | |

TABLE 1a-continued

| $R_1$ | $R_2$ | R | X | T | Y | Z | m.p. (°C.) |
|---|---|---|---|---|---|---|---|
| CH(OCH$_3$)CH$_3$ | H | H | OCF$_2$H | H | SPh | CH | |
| CH(OCH$_3$)CH$_3$ | H | H | OCH$_3$ | SCH$_3$ | SeCH$_3$ | CH | |
| CH(OCH$_3$)CH$_3$ | H | H | OCH$_3$ | SPh | SPh | N | |
| CH(OCH$_3$)CH$_3$ | H | H | CH$_3$ | SCH$_3$ | SeCH$_3$ | N | |
| CH(OCH$_3$)CH$_3$ | H | H | F | H | SPh | CH | |
| CH(OCH$_3$)CH$_3$ | H | H | OCH$_3$ | SPh | SPh | CH | |
| CH(OCH$_3$)CH$_3$ | H | H | CF$_3$ | H | SeCH$_3$ | CH | |
| CH(OCH$_3$)CH$_3$ | H | H | CF$_3$ | H | SPh | CH | |
| CH(OCH$_3$)CH$_3$ | H | H | OCH$_3$ | H | OPh | N | |
| CH(OCH$_3$)CH$_3$ | H | H | OCH$_2$CH$_3$ | H | SeCH$_3$ | N | |
| CH(OCH$_3$)CH$_3$ | H | H | OCH$_2$CH$_3$ | SeCH$_3$ | SeCH$_3$ | CH | |
| CH(OCH$_3$)CH$_3$ | H | CH$_3$ | OCH$_3$ | H | SPh | CH | |
| CH(OCH$_3$)CH$_3$ | 3-OCH$_3$ | H | OCH$_3$ | H | SPh | CH | |
| CH(OCH$_3$)CH$_3$ | 5-CF$_3$ | H | OCH$_3$ | H | SPh | CH | |
| CH(OCH$_3$)CH$_3$ | 6-F | H | OCH$_3$ | H | SePh | CH | |
| SO$_2$N(CH$_2$CH$_3$)$_2$ | H | H | OCH$_3$ | H | SeCH$_3$ | CH | |
| SO$_2$N(CH$_2$CH$_3$)$_2$ | H | H | OCH$_3$ | H | SPh | CH | |
| SO$_2$N(CH$_2$CH$_3$)$_2$ | H | H | CH$_3$ | H | SePh | CH | |
| SO$_2$N(CH$_2$CH$_3$)$_2$ | H | H | OCH$_3$ | H | SO$_2$Ph | CH | |
| SO$_2$N(CH$_2$CH$_3$)$_2$ | H | H | CH$_3$ | SPh | SPh | CH | |
| SO$_2$N(CH$_2$CH$_3$)$_2$ | H | H | OCH$_2$CH$_3$ | H | SPh | CH | |
| SO$_2$N(CH$_2$CH$_3$)$_2$ | H | H | OCH$_3$ | SePh | SePh | CH | |
| SO$_2$N(CH$_2$CH$_3$)$_2$ | H | H | Br | H | SePh | CH | |
| SO$_2$N(CH$_2$CH$_3$)$_2$ | H | H | OCH$_3$ | H | OPh | CH | |
| SO$_2$N(CH$_2$CH$_3$)$_2$ | H | H | OCH$_3$ | SeCH$_3$ | SeCH$_3$ | CH | |
| SO$_2$N(CH$_2$CH$_3$)$_2$ | H | H | OCH$_3$ | H | SPh | N | |
| SO$_2$N(CH$_2$CH$_3$)$_2$ | H | H | OCF$_2$H | H | SPh | CH | |
| SO$_2$N(CH$_2$CH$_3$)$_2$ | H | H | OCH$_3$ | SCH$_3$ | SeCH$_3$ | CH | |
| SO$_2$N(CH$_2$CH$_3$)$_2$ | H | H | OCH$_3$ | SPh | SPh | N | |
| SO$_2$N(CH$_2$CH$_3$)$_2$ | H | H | CH$_3$ | SCH$_3$ | SeCH$_3$ | N | |
| SO$_2$N(CH$_2$CH$_3$)$_2$ | H | H | F | H | SPh | CH | |
| SO$_2$N(CH$_2$CH$_3$)$_2$ | H | H | OCH$_3$ | SPh | SPh | CH | |
| SO$_2$N(CH$_2$CH$_3$)$_2$ | H | H | CF$_3$ | H | SeCH$_3$ | CH | |
| SO$_2$N(CH$_2$CH$_3$)$_2$ | H | H | CF$_3$ | H | SPh | CH | |
| SO$_2$N(CH$_2$CH$_3$)$_2$ | H | H | OCH$_3$ | H | OPh | N | |
| SO$_2$N(CH$_2$CH$_3$)$_2$ | H | H | OCH$_2$CH$_3$ | H | SeCH$_3$ | N | |
| SO$_2$N(CH$_2$CH$_3$)$_2$ | H | H | OCH$_2$CH$_3$ | SeCH$_3$ | SeCH$_3$ | CH | |
| SO$_2$N(CH$_2$CH$_3$)$_2$ | H | CH$_3$ | OCH$_3$ | H | SPh | CH | |
| SO$_2$N(CH$_2$CH$_3$)$_2$ | 3-OCH$_3$ | H | OCH$_3$ | H | SPh | CH | |
| SO$_2$N(CH$_2$CH$_3$)$_2$ | 5-CF$_3$ | H | OCH$_3$ | H | SPh | CH | |
| SO$_2$N(CH$_2$CH$_3$)$_2$ | 6-F | H | OCH$_3$ | H | SePh | CH | |
| C$_2$H$_5$ | H | H | OCH$_3$ | H | SeCH$_3$ | CH | |
| CH$_2$CH$_2$CH$_3$ | H | H | OCH$_3$ | H | SPh | CH | |
| CH$_2$CH$_2$CH$_2$CH$_3$ | H | H | CH$_3$ | H | SePh | CH | |
| OCH$_2$CH$_3$ | H | H | OCH$_3$ | H | SO$_2$Ph | CH | |
| OCH$_2$CH$_2$CH$_3$ | H | H | CH$_3$ | SPh | SPh | CH | |
| F | H | H | OCH$_2$CH$_3$ | H | SPh | CH | |
| F | H | H | OCH$_3$ | SePh | SePh | CH | |
| F | H | H | Br | H | SePh | CH | |
| F | H | H | OCH$_3$ | H | OPh | CH | |
| F | H | H | OCH$_3$ | SeCH$_3$ | SeCH$_3$ | CH | |
| CO$_2$CH$_2$CH$_2$CH$_3$ | H | H | OCH$_3$ | H | SPh | N | |
| CO$_2$CH$_2$CH$_2$CH$_3$ | H | H | OCF$_2$H | H | SPh | CH | |
| CO$_2$CH$_2$CH$_2$CH$_3$ | H | H | OCH$_3$ | SCH$_3$ | SeCH$_3$ | CH | |
| CO$_2$CH$_2$CH$_2$CH$_3$ | H | H | OCH$_3$ | SPh | SPh | N | |
| CO$_2$CH$_2$CH$_2$CH$_3$ | H | H | CH$_3$ | SCH$_3$ | SeCH$_3$ | N | |
| SO$_2$N(OCH$_3$)$_3$CH$_3$ | H | H | F | H | SPh | CH | |
| SO$_2$N(OCH$_3$)$_3$CH$_3$ | H | H | OCH$_3$ | SPh | SPh | CH | |
| OSO$_2$N(CH$_3$)$_2$ | H | H | CF$_3$ | H | SeCH$_3$ | CH | |
| SOCH$_3$ | H | H | OCH$_3$ | H | OPh | N | |
| SOCH$_3$ | H | H | OCH$_2$CH$_3$ | H | SeCH$_3$ | N | |
| SOCH$_3$ | H | H | OCH$_2$CH$_3$ | SeCH$_3$ | SeCH$_3$ | CH | |
| SCF$_3$ | H | CH$_3$ | OCH$_3$ | H | SPh | CH | |
| SF$_3$ | 3-OCH$_3$ | H | OCH$_3$ | H | SPh | CH | |
| OCH$_2$CH$_2$CH=CH$_2$ | 5-CF$_3$ | H | OCH$_3$ | H | SPh | CH | |
| OCH$_2$CH—C≡CH | 6-F | H | OCH$_3$ | H | SePh | CH | |
| CO$_2$CH$_3$ | H | H | CH$_3$ | H | CH$_2$OSi(CH$_3$)$_3$ | CH | 137–140 |
| Cl | H | H | CH$_3$ | H | CH$_2$OSi(CH$_3$)$_3$ | CH | 121–124 |
| CO$_2$C$_2$H$_5$ | H | H | CH$_3$ | H | CH$_2$OSi(CH$_3$)$_3$ | CH | |

TABLE 1a-continued

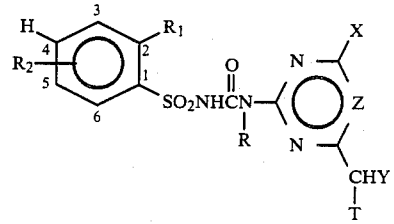

| R₁ | R₂ | R | X | T | Y | Z | m.p. (°C.) |
|---|---|---|---|---|---|---|---|
| CF₃ | H | H | CH₃ | H | CH₂OSi(CH₃)₃ | CH | 102–105 |
| SO₂CH₃ | H | H | CH₃ | H | CH₂OSi(CH₃)₃ | CH | 176–178 |
| CO₂CH₃ | H | H | CH₃ | H | CH₂OH | CH | 138–141 |
| SO₂CH₃ | H | H | CH₃ | H | CH₂OH | CH | 156–158 |
| Cl | H | H | CH₃ | H | CH₂OH | CH | 124–125 |
| CF₃ | H | H | CH₃ | H | CH₂OH | CH | 126–127.5 |
| CO₂CH₃ | H | H | OCH₃ | H | OSi(CH₃)₃ | CH | 111–114 |
| CO₂CH₂CH₃ | H | H | OCH₃ | H | OSi(CH₃)₃ | CH | |
| Cl | H | H | OCH₃ | H | OSi(CH₃)₃ | CH | 169–171 |
| SO₂N(CH₃)₂ | H | H | OCH₃ | H | OSi(CH₃)₃ | CH | 145–148 |
| CF₃ | H | H | OCH₃ | H | OSi(CH₃)₃ | CH | 139–141 |
| SO₂CH₃ | H | H | OCH₃ | H | OSi(CH₃)₃ | CH | 172–174 |
| Br | H | H | OCH₃ | H | OSi(CH₃)₃ | CH | 161–163 |
| NO₂ | H | H | OCH₃ | H | OSi(CH₃)₃ | N | |
| SO₂CH₂CH₂CH₃ | H | H | OCH₃ | H | OSi(CH₃)₃ | N | |
| CO₂CH₂CH₂CH₃ | H | H | OCH₃ | H | OSi(CH₃)₃ | N | |
| CH₃ | H | H | OCH₃ | H | CH₂OH | N | |
| F | H | H | OCH₃ | H | CH₂OH | N | |

TABLE 1b

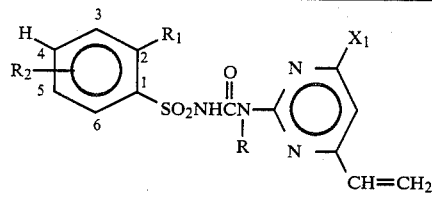

| R₁ | R₂ | R | X₁ | m.p. (°C.) |
|---|---|---|---|---|
| CO₂CH₃ | H | H | CH₃ | 154–160 |
| CO₂CH₃ | H | H | OCH₃ | 136.5–141 |
| CO₂CH₂CH₃ | H | H | OCH₃ | |
| CO₂CH₂CH₂CH₃ | H | H | OCH₃ | |
| SO₂N(CH₃)₂ | H | H | CH₃ | 173–178 |
| SO₂N(CH₃)₂ | H | H | OCH₃ | |
| CH₂CH₃ | H | H | OCH₃ | |
| CH₂OCH₃ | H | H | OCH₃ | |
| OCH₂CH₂OCH₃ | H | H | OCH₃ | |
| SO₂N(OCH₃)CH₃ | H | H | OCH₃ | |
| OSO₂CH₃ | H | H | CH₃ | |
| OSO₂CH₃ | H | H | OCH₃ | |
| OSO₂CH₂CH₂CH₃ | H | H | OCH₃ | |
| Ph | H | H | OCH₃ | |
|  | H | H | OCH₃ | |
| 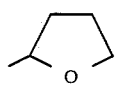 | H | H | OCH₃ | |
| 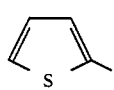 | H | H | OCH₃ | |
| CO₂CH₃ | 3-OCH₃ | H | OCH₃ | |
| CO₂CH₃ | 5-Cl | H | OCH₃ | |
| SO₂N(CH₃)₂ | 6-CF₃ | H | OCH₃ | |
| CO₂CH₃ | H | CH₃ | OCH₃ | |
| CO₂CH₃ | H | H | OCH₃ | |

TABLE 1b-continued

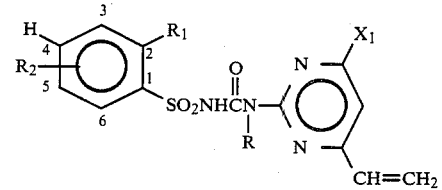

| R₁ | R₂ | R | X₁ | m.p. (°C.) |
|---|---|---|---|---|
| CO₂CH₃ | H | H | CH₃ | |
| SO₂N(CH₃)₂ | H | H | CH₃ | |
| OSO₂CH₃ | H | H | OCH₃ | |
| CH₂CH₃ | H | H | OCH₃ | |
| CO₂CH₃ | 3-OCH₃ | H | OCH₃ | |

TABLE 1c

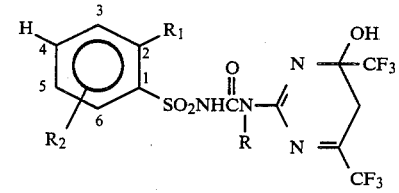

| R₁ | R₂ | R | m.p. (°C.) |
|---|---|---|---|
| H | H | H | |
| CO₂CH₃ | H | H | |
| Cl | H | H | 187–194 |
| Br | H | H | |
| SO₂N(CH₃)₂ | H | H | |
| NO₂ | H | H | |
| CF₃ | H | H | |
| OSO₂CH₃ | H | H | |
| CH₃ | H | H | |
| CO₂CH₂CH₃ | H | H | |
| SO₂N(OCH₃)CH₃ | H | H | |
| SO₂N(CH₂CH₃)₂ | H | H | |
| CH₂CH₃ | H | H | |
| CH₂OCH₃ | H | H | |
| OCH₃ | H | H | |

TABLE 1c-continued

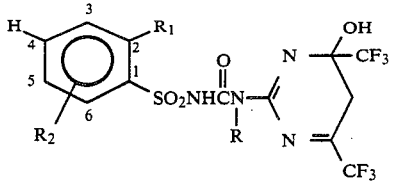

| R₁ | R₂ | R | m.p. (°C.) |
|---|---|---|---|
| OCH₂CH=CH₂ | H | H | |
| OCH₂C≡CH | H | H | |
| Ph | H | H | |
| CO₂CH₃ | 3-OCH₃ | H | |
| SO₂N(CH₃)₂ | 5-Cl | H | |
| CO₂CH₃ | 6-CF₃ | H | |
| CO₂CH₃ | 3-CH₃ | H | |
| CO₂CH₃ | H | CH₃ | |

TABLE 1d

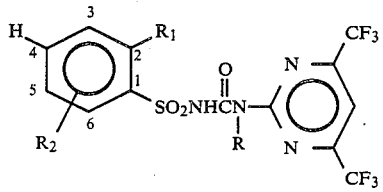

| R₁ | R₂ | R | m.p. (°C.) |
|---|---|---|---|
| CO₂CH₃ | H | H | 153–161 |
| Cl | H | H | 158–162 |
| Br | H | H | |
| SO₂N(CH₃)₂ | H | H | 138–142 |
| NO₂ | H | H | 180–190 |
| CF₃ | H | H | |
| OSO₂CH₃ | H | H | 173–178 |
| CH₃ | H | H | 133–153 |
| CO₂CH₂CH₃ | H | H | 103–107 |
| SO₂N(OCH₃)CH₃ | H | H | |
| SO₂N(CH₂CH₃)₂ | H | H | |
| CH₂CH₃ | H | H | |
| CH₂OCH₃ | H | H | |
| OCH₃ | H | H | |
| Ph | H | H | |
| CO₂CH₃ | 3-OCH₃ | H | |
| SO₂N(CH₃)₂ | 5-Cl | H | |
| CO₂CH₃ | 6-CF₃ | H | |
| CO₂CH₃ | 6-CH₃ | H | |

TABLE 1d-continued

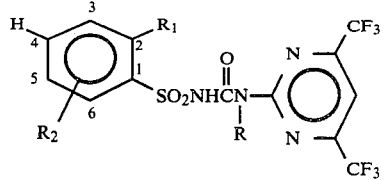

| R₁ | R₂ | R | m.p. (°C.) |
|---|---|---|---|
| CO₂CH₃ | H | CH₃ | |
| SCH₃ | H | H | |
| SO₂CH₃ | H | H | 200–205 |
| SO₂CH₂CH₂CH₃ | H | H | 195–200 |

TABLE 1e

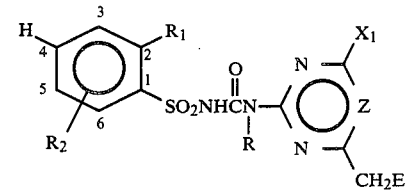

| R₁ | R₂ | R | X₁ | E | Z | m.p. (°C.) |
|---|---|---|---|---|---|---|
| OCH₂CH₃ | H | H | CH₃ | F | CH | |
| OCH₂CH₂CH₃ | H | H | CH₃ | F | CH | |
| SO₂N(CH₃)₂ | H | H | CH₃ | F | CH | 221–224 |
| SO₂N(CH₃)₂ | H | H | OCH₃ | F | CH | 215–220 |
| SO₂N(CH₃)₂ | H | H | OCH₃ | F | N | |
| SO₂N(CH₂CH₃)₂ | H | H | OCH₃ | F | CH | |
| SO₂N(OCH₃)CH₃ | H | H | CH₃ | F | CH | |
| OCH₂CH₂CH₃ | H | H | OCH₃ | Cl | CH | |
| SO₂N(CH₃)₂ | H | H | OCH₃ | Br | CH | |
| SO₂(CH₃)₂ | H | H | OCH₃ | Br | N | |
|  | H | H | OCH₃ | F | CH | |
| SO₂N(CH₃)₂ | 3-OCH₃ | H | OCH₃ | F | CH | |
| SO₂N(CH₃)₂ | 6-CF₃ | H | OCH₃ | F | CH | |
| SO₂N(CH₃)₂ | H | CH₃ | OCH₃ | F | CH | |
| SO₂N(CH₃)₂ | H | H | OCH₃ | F | N | |
| SO₂N(CH₂CH₃)₂ | H | H | CH₃ | F | N | |
| CH₂CH₃ | H | H | OCH₃ | F | N | |

TABLE 1f

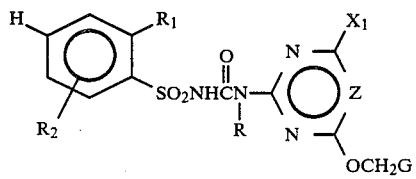

| R₁ | R₂ | R | X₁ | Z | G | m.p. (°C.) |
|---|---|---|---|---|---|---|
| CH₃ | H | H | OCH₃ | CH | CH(—OCH₂CH₂O—) | |
| CH₃ | H | H | CH₃ | N | CH(OCH₃)₂ | |
| C₂H₅ | H | CH₃ | OCH₃ | CH | CH(OCH₃)₂ | |
| C₂H₅ | H | H | OCH₃ | CH | CH(OC₂H₅)₂ | |
| CH(CH₃)₂ | H | H | OCH₃ | CH | CH(—OCH₂CH₂O—) | |
| CH(CH₃)C₂H₅ | H | H | OCH₃ | CH | CH(OCH₃)₂ | |
| CH₂CH₂CH₂CH₃ | H | H | OCH₃ | CH | CH(—OCH₂CH₂O—) | |
| OCH₃ | H | H | OCH₃ | CH | CH(—OCH₂CH₂O—) | |
| OCH₃ | 5-Cl | H | CH₃ | CH | CH(—OCH₂CH₂O—) | |
| OC₂H₅ | H | H | OCH₃ | CH | CH(—OCH₂CH₂O—) | |
| OCH(CH₃)₂ | H | H | OCH₃ | CH | CH(OCH₃)₂ | |

TABLE 1f-continued

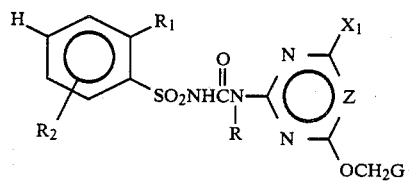

| R₁ | R₂ | R | X₁ | Z | G | m.p. (°C.) |
|---|---|---|---|---|---|---|
| OC₄H₉—n | H | H | OCH₃ | N | CH(OCH₃)₂ | |
| OCH₂CH₂OCH₃ | H | H | OCH₃ | CH | CH(OCH₃)₂ | |
| F | H | H | CH₃ | CH | CH(—OCH₂CH₂O—) | |
| Cl | H | H | CH₃ | CH | CH(—OCH₂CH₂O—) | 115–118 |
| Cl | H | H | OC₂H₅ | CH | CH(—OCH₂CH₂O—) | |
| Cl | H | H | OCH₃ | CH | CH(OCH₃)₂ | |
| Br | 5-CH₃ | H | CH₃ | CH | CH(OCH₃)₂ | |
| NO₂ | H | H | OCH₃ | CH | CH(OC₂H₅)₂ | |
| NO₂ | H | CH₃ | CH₃ | CH | CH(OCH₃)₂ | |
| CF₃ | H | H | OCH₃ | CH | CH(—OCH₂CH₂O—) | |
| CO₂CH₃ | H | H | OCH₃ | CH | CH(—OCH₂CH₂O—) | 102–104 |
| CO₂CH₃ | H | H | CH₃ | CH | CH(—OCH₂CH₂O—) | 148–150 |
| CO₂CH₃ | H | H | OC₂H₅ | CH | CH(—OCH₂CH₂O—) | |
| CO₂CH₃ | 5-OCH₃ | H | OCH₃ | N | CH(OCH₃)₂ | |
| CO₂C₂H₅ | H | H | OCH₃ | CH | CH(OCH₃)₂ | |
| CO₂CH₂CH=CH₂ | H | H | CH₃ | CH | CH(OC₂H₅)₂ | |
| CO₂C₄H₉—n | H | H | OCH₃ | CH | CH(OCH₃)₂ | |
| SO₂N(CH₃)₂ | H | H | OCH₃ | CH | CH(—OCH₂CH₂O—) | 122–124 |
| SO₂N(CH₃)₂ | H | H | CH₃ | CH | CH(—OCH₂CH₂O—) | 183–185(d) |
| SO₂N(CH₃)₂ | H | H | OC₂H₅ | CH | CH(OCH₃)₂ | |
| SO₂N(CH₃)C₂H₅ | 3-CF₃ | H | OCH₃ | CH | CH(OCH₃)₂ | |
| OSO₂CH₃ | H | H | OCH₃ | CH | CH(OCH₃)₂ | |
| OSO₂C₂H₅ | H | H | CH₃ | CH | CH(—OCH₂CH₂O—) | |
| SCF₃ | H | H | OC₂H₅ | CH | CH(OCH₃)₂ | |
| OCHF₂ | H | H | OCH₃ | CH | CH(OCH₃)₂ | |
| CO₂C₂H₅ | H | H | CH₃ | CH | CH(—OCH₂CH₂O—) | 151–153 |
| CO₂CH₃ | H | H | OCH₃ | N | CH(OCH₃)₂ | |
| CO₂CH₃ | H | H | OCH₃ | CH | CH(OC₂H₅)₂ | |
| CO₂CH₃ | H | H | CH₃ | CH | CH(OCH₃)₂ | |
| SO₂CH₃ | H | H | OCH₃ | CH | CH(—OCH₂CH₂O—) | 191–194 |
| SO₂CH₃ | H | H | CH₃ | CH | CH(—OCH₂CH₂O—) | 194–196(d) |
| SO₂CH₃ | H | H | CH₃ | CH | CH(OCH₃)₂ | |
| SO₂CH₃ | H | H | OCH₃ | CH | CH(OCH₃)₂ | |
| SO₂C₂H₅ | H | H | OCH₃ | CH | CH(—OCH₂CH₂O—) | |
| SO₂CH₂CH₂CH₃ | H | H | CH₃ | CH | CH(—OCH₂CH₂O—) | |
| SO₂CH₂CH=CH₂ | H | H | OCH₃ | CH | CH(OCH₃)₂ | |
| SO₂C₂H₅ | H | H | OCH₃ | CH | CH(OCH₃)₂ | |
| OCH₂C≡CH | H | H | OCH₃ | CH | CH(—OCH₂CH₂O—) | |
| OCH₂C≡CCH₃ | H | H | CH₃ | CH | CH(—OCH₂CH₂O—) | |
| OCH₂CH=CH₂ | H | H | OCH₃ | CH | CH(—OCH₂CH₂O—) | |
| OCH₂CH₂CH=CH₂ | H | H | OCH₃ | CH | CH(—OCH₂CH₂O—) | |
| CH₂OCH₃ | H | H | OCH₃ | CH | CH(—OCH₂CH₂O—) | |
| CH₂OC₂H₅ | H | H | OCH₃ | CH | CH(OCH₃)₂ | |
| C₆H₅ | 6-Cl | H | CH₃ | CH | CH(OC₂H₅)₂ | |
| C₆H₅ | 6-OCH₃ | H | OCH₃ | CH | CH(OCH₃)₂ | |
| ![thiadiazolyl] | H | H | OCH₃ | N | CH(—OCH₂CH₂O—) | |
| ![furyl] | H | H | CH₃ | CH | CH(—OCH₂CH₂O—) | |
| ![isoxazolyl] | H | H | OCH₃ | CH | CH(—OCH₂CH₂O—) | |
| CO₂CH₃ | H | H | OCH₃ | CH | C₆H₅ | 110–112(d) |
| CO₂CH₃ | H | H | CH₃ | CH | C₆H₅ | |
| SO₂N(CH₃)₂ | H | H | OCH₃ | CH | C₆H₅ | |
| SO₂CH₃ | H | H | OCH₃ | N | C₆H₅ | |
| Cl | H | H | OCH₃ | CH | C₆H₅ | |
| OCHF₂ | H | H | OCH₃ | CH | C₆H₅ | |

TABLE 2a

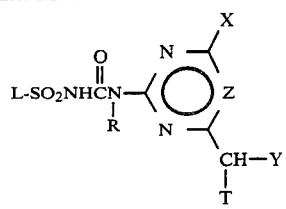

| L | R₃ | R₄ | R | X | T | Y | Z | m.p. (°C.) |
|---|---|---|---|---|---|---|---|---|
| L-2 | CH₃ | — | H | OCH₃ | H | SeCH₃ | CH | |
| L-2 | CH₃ | — | H | OCH₃ | H | SePh | CH | |
| L-2 | OCH₃ | — | H | CH₃ | H | SPh | CH | |
| L-2 | OCH₃ | — | H | OCH₃ | SPh | SPh | CH | |
| L-2 | OCH₃ | — | H | OCH₃ | SeCH₃ | SeCH₃ | CH | |
| L-2 | F | — | H | OCH₃ | H | SPh | N | |
| L-2 | F | — | H | Cl | H | SPh | CH | |
| L-2 | Cl | — | H | OCH₃ | H | SeCH₃ | CH | |
| L-2 | Cl | — | H | OCH₃ | H | SeCH₃ | N | |
| L-2 | Br | — | H | CH₃ | SPh | SPh | N | |
| L-2 | SO₂N(CH₃)₂ | — | H | OCH₃ | H | OPh | CH | |
| L-2 | SO₂N(CH₃)₂ | — | H | Br | H | SePh | CH | |
| L-2 | SO₂N(CH₃)₂ | — | H | OCH₃ | H | SePh | CH | |
| L-2 | SO₂N(CH₃)₂ | — | H | CH₃ | SeCH₃ | SeCH₃ | CH | |
| L-2 | SO₂N(CH₃)₂ | — | H | OCH₃ | H | SPh | N | |
| L-2 | OSO₂CH₃ | — | H | OCH₃ | SPh | SPh | N | |
| L-2 | OSO₂CH₃ | — | H | OCH₃ | H | SO₂Ph | N | |
| L-2 | SOCH₃ | — | H | F | H | OPh | CH | |
| L-2 | SOCH₃ | — | H | OCH₃ | H | SPh | CH | |
| L-2 | SCH₃ | — | H | OCH₃ | H | SePh | CH | |
| L-2 | SCH₃ | — | H | OCH₃ | H | SeCH₃ | CH | |
| L-2 | SO₂CH₃ | — | H | CH₃ | SeCH₃ | SePh | CH | |
| L-2 | SO₂CH₃ | — | H | OCH₃ | H | SPh | CH | |
| L-2 | SO₂CH₃ | — | H | OCH₃ | H | SPh | N | |
| L-2 | CH₃ | — | H | OCH₂CH₃ | H | SPh | CH | |
| L-2 | SO₂N(CH₃)₂ | — | H | CH₃ | H | CH₂OSi(CH₃)₃ | CH | |
| L-2 | CH₃ | — | H | OCH₃ | H | SeCH₃ | CH | |
| L-2 | OCH₃ | — | CH₃ | OCH₃ | H | SPh | CH | |
| L-3 | — | CH₃ | H | OCH₃ | H | SeCH₃ | CH | |
| L-3 | — | CH₃ | H | OCH₃ | H | SePh | CH | |
| L-3 | — | CH₂CH₃ | H | CH₃ | H | SPh | CH | |
| L-3 | — | OCH₃ | H | OCH₃ | SPh | SPh | CH | |
| L-3 | — | OCH₃ | H | OCH₃ | SeCH₃ | SeCH₃ | CH | |
| L-3 | — | F | H | OCH₃ | H | SPh | N | |
| L-3 | — | F | H | Cl | H | SPh | CH | |
| L-3 | — | Cl | H | OCH₃ | H | SeCH₃ | CH | |
| L-3 | — | Cl | H | OCH₃ | H | SeCH₃ | N | |
| L-3 | — | Br | H | CH₃ | SPh | SPh | N | |
| L-3 | — | Br | H | OCH₃ | H | OPh | CH | |
| L-3 | — | OCH₂CH₃ | H | Br | H | SePh | CH | |
| L-3 | — | SO₂N(CH₃)₂ | H | OCH₃ | H | SePh | CH | |
| L-3 | — | SO₂N(CH₃)₂ | H | CH₃ | SeCH₃ | SeCH₃ | CH | |
| L-3 | — | SO₂N(CH₃)₂ | H | OCH₃ | H | SPh | N | |
| L-3 | — | SO₂N(CH₂CH₃)₂ | H | OCH₃ | SPh | SPh | N | |
| L-3 | — | SO₂N(CH₂CH₃)₂ | H | OCH₃ | H | SO₂Ph | N | |
| L-3 | — | SO₂N(OCH₃)CH₃ | H | OCH₃ | H | SePh | CH | |
| L-3 | — | SCH₃ | H | OCH₃ | H | SeCH₃ | CH | |
| L-3 | — | SCH₃ | H | CH₃ | SeCH₃ | SePh | CH | |
| L-3 | — | SOCH₃ | H | OCH₃ | H | SPh | CH | |
| L-3 | — | SO₂CH₃ | H | OCH₃ | H | SPh | N | |
| L-3 | — | SO₂CH₃ | H | OCH₂CH₃ | H | SPh | CH | |
| L-3 | — | SO₂CH₃ | H | OCH₃ | H | SeCH₃ | CH | |
| L-3 | — | SO₂CH₃ | CH₃ | OCH₃ | H | SPh | CH | |
| L-3 | — | CH₃ | H | OCH₃ | H | CH₂OH | CH | |

TABLE 2b

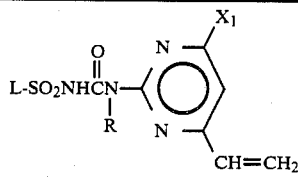

| L | R₃ | R₄ | R | X₁ | m.p. (°C.) |
|---|---|---|---|---|---|
| L-2 | SO₂N(CH₃)₂ | — | H | CH₃ | |
| L-2 | SO₂N(CH₃)₂ | — | H | OCH₃ | |
| L-2 | SO₂N(CH₃)₂ | — | H | OCH₃ | |
| L-2 | CH₃ | — | H | CH₃ | |
| L-2 | CH₃ | — | H | OCH₃ | |
| L-2 | CH₃ | — | H | OCH₂CH₃ | |
| L-2 | H | — | H | OCH₃ | |
| L-2 | H | — | H | OCH₃ | |
| L-2 | F | — | H | OCH₃ | |
| L-2 | Cl | — | H | OCH₃ | |
| L-2 | Cl | — | H | CH₃ | |
| L-2 | Br | — | H | OCH₃ | |
| L-2 | OSO₂CH₃ | — | H | OCH₃ | |
| L-2 | OSO₂CH₃ | — | H | CH₃ | |
| L-2 | SCH₃ | — | H | CH₃ | |
| L-2 | SCH₃ | — | H | OCH₃ | |
| L-2 | SOCH₃ | — | H | OCH₃ | |
| L-2 | SOCH₃ | — | H | OCH₃ | |
| L-2 | SO₂CH₃ | — | H | CH₃ | |
| L-2 | SO₂CH₃ | — | H | OCH₃ | |
| L-2 | SO₂N(CH₃)₂ | — | H | OCH₂CH₃ | |
| L-2 | OSO₂CH₃ | — | H | CH₃ | |
| L-2 | SO₂N(CH₃)₂ | — | CH₃ | OCH₂CH₃ | |
| L-2 | H | — | CH₃ | OCH₃ | |
| L-3 | — | CH₃ | H | CH₃ | |
| L-3 | — | CH₃ | H | OCH₃ | |
| L-3 | — | CH₃ | H | OCH₃ | |
| L-3 | — | CH₂CH₃ | H | OCH₃ | |
| L-3 | — | CH₂CH₃ | H | CH₃ | |
| L-3 | — | OCH₃ | H | OCH₃ | |
| L-3 | — | OCH₃ | H | OCH₂CH₃ | |
| L-3 | — | F | H | OCH₃ | |
| L-3 | — | F | H | OCH₃ | |
| L-3 | — | Cl | H | OCH₃ | |
| L-3 | — | Cl | H | OCH₃ | |
| L-3 | — | Br | H | CH₃ | |
| L-3 | — | Br | H | OCH₃ | |
| L-3 | — | OCH₂CH₃ | H | OCH₃ | |
| L-3 | — | OCH₂CH₃ | H | CH₃ | |
| L-3 | — | SO₂N(CH₃)₂ | H | CH₃ | |
| L-3 | — | SO₂N(CH₃)₂ | H | OCH₃ | |
| L-3 | — | SO₂N(CH₃)₂ | H | OCH₃ | |
| L-3 | — | SO₂N(CH₂CH₃)₂ | H | OCH₃ | |
| L-3 | — | SO₂N(CH₂CH₃)₂ | H | CH₃ | |
| L-3 | — | SO₂N(OCH₃)CH₃ | H | OCH₃ | |
| L-3 | — | SCH₃ | CH₃ | OCH₂CH₃ | |
| L-3 | — | SO₂CH₃ | CH₃ | OCH₃ | |

TABLE 2c

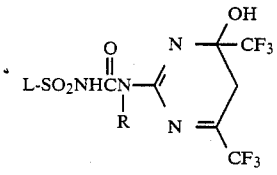

| L | R₃ | R₄ | R | m.p. (°C.) |
|---|---|---|---|---|
| L-2 | H | — | H | |
| L-2 | CH₃ | — | H | |
| L-2 | OCH₃ | — | H | |
| L-2 | F | — | H | |
| L-2 | Cl | — | H | |
| L-2 | Br | — | H | |
| L-2 | SO₂N(CH₃)₂ | — | H | |
| L-2 | OSO₂CH₃ | — | H | |
| L-2 | SCH₃ | — | H | |

TABLE 2c-continued

| L | R₃ | R₄ | R | m.p. (°C.) |
|---|---|---|---|---|
| L-2 | SOCH₃ | — | H | |
| L-2 | SO₂CH₃ | — | H | |
| L-2 | CH₃ | — | CH₃ | |
| L-3 | — | CH₃ | H | |
| L-3 | — | CH₂CH₃ | H | |
| L-3 | — | OCH₃ | H | |
| L-3 | — | OCH₂CH₃ | H | |
| L-3 | — | F | H | |
| L-3 | — | Cl | H | |
| L-3 | — | Br | H | |
| L-3 | — | SO₂N(CH₃)₂ | H | |
| L-3 | — | SO₂N(CH₂CH₃)₂ | H | |
| L-3 | — | SO₂N(OCH₃)CH₃ | H | |
| L-3 | — | SCH₃ | H | |
| L-3 | — | SO₂CH₃ | H | |
| L-3 | — | CH₃ | CH₃ | |

TABLE 2d

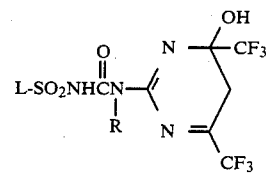

| L | R₃ | R₄ | R | m.p. (°C.) |
|---|---|---|---|---|
| L-2 | H | — | H | |
| L-2 | CH₃ | — | H | |
| L-2 | OCH₃ | — | H | |
| L-2 | F | — | H | |
| L-2 | Cl | — | H | |
| L-2 | Br | — | H | |
| L-2 | SO₂N(CH₃)₂ | — | H | |
| L-2 | OSO₂CH₃ | — | H | |
| L-2 | SCH₃ | — | H | |
| L-2 | SOCH₃ | — | H | |
| L-2 | SO₂CH₃ | — | H | |
| L-2 | CH₃ | — | CH₃ | |
| L-3 | — | CH₃ | H | |
| L-3 | — | CH₂CH₃ | H | |
| L-3 | — | OCH₃ | H | |
| L-3 | — | OCH₂CH₃ | H | |
| L-3 | — | F | H | |
| L-3 | — | Cl | H | |
| L-3 | — | Br | H | |
| L-3 | — | SO₂N(CH₃)₂ | H | |
| L-3 | — | SO₂N(CH₂CH₃)₂ | H | |
| L-3 | — | SO₂N(OCH₃)CH₃ | H | |
| L-3 | — | SCH₃ | H | |
| L-3 | — | SO₂CH₃ | H | |
| L-3 | — | CH₃ | CH₃ | |

TABLE 2e

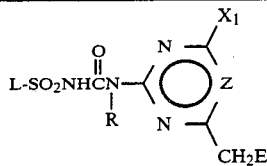

| L | R3 | R4 | R | X1 | E | Z | m.p. (°C.) |
|---|---|---|---|---|---|---|---|
| L-2 | H | — | H | OCH3 | F | CH | |
| L-2 | CH3 | — | H | OCH3 | F | CH | |
| L-2 | CH3 | — | H | OCH3 | Cl | CH | |
| L-2 | OCH3 | — | H | CH3 | F | CH | |
| L-2 | F | — | H | OCH3 | F | CH | |
| L-2 | Cl | — | H | OCH3 | F | CH | |
| L-2 | Cl | — | H | OCH3 | Cl | CH | |
| L-2 | Br | — | H | CH3 | F | N | |
| L-2 | SO2N(CH3)2 | — | H | OCH3 | F | CH | |
| L-2 | SO2N(CH3)2 | — | H | OCH3 | Br | CH | |
| L-2 | OSO2CH3 | — | H | OCH3 | F | CH | |

TABLE 2e-continued

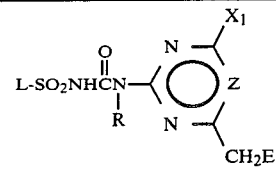

| L | R3 | R4 | R | X1 | E | Z | m.p. (°C.) |
|---|---|---|---|---|---|---|---|
| L-3 | — | CH2CH3 | H | OCH3 | F | CH | |
| L-3 | — | OCH3 | H | OCH3 | F | N | |
| L-3 | — | F | H | CH3 | F | CH | |
| L-3 | — | Br | H | OCH3 | Br | CH | |
| L-3 | — | SO2N(CH2CH3)2 | H | OCH3 | F | CH | |
| L-3 | — | SO2N(CH3)2 | H | OCH3 | F | N | |
| L-3 | — | SCH3 | H | CH3 | Cl | CH | |
| L-3 | — | SO2CH3 | H | OCH3 | F | CH | |
| L-3 | — | CH3 | CH3 | OCH3 | F | CH | |
| L-3 | — | OCH2CH3 | CH3 | CH3 | Br | N | |

TABLE 2f

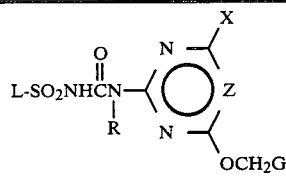

| L | R3 | R4 | R | X | Z | G | m.p. (°C.) |
|---|---|---|---|---|---|---|---|
| L-2 | Cl | — | H | OCH3 | CH | CH(—OCH2CH2O—) | |
| L-2 | Cl | — | H | CH3 | CH | CH(OCH3)2 | |
| L-2 | OCH3 | — | H | OCH3 | CH | CH(OCH3)2 | |
| L-2 | OCH3 | — | H | CH3 | CH | CH(—OCH2CH2O—) | |
| L-2 | OSO2CH3 | — | H | OCH3 | CH | CH(—OCH2CH2O—) | |
| L-2 | SO2CH3 | — | CH3 | OCH3 | CH | CH(OCH3)2 | |
| L-2 | SCH3 | — | H | OCH3 | N | CH(—OCH2CH2O—) | |
| L-2 | Br | — | H | OCH3 | CH | CH(—OCH2CH2O—) | |
| L-2 | SO2N(CH3)2 | — | H | OCH3 | CH | CH(—OCH2CH2O—) | |
| L-2 | CH3 | — | H | OCH3 | CH | CH(—OCH2CH2O—) | |
| L-3 | — | CH3 | H | OCH3 | CH | CH(—OCH2CH2O—) | |
| L-3 | — | OCH3 | H | OCH3 | CH | CH(OCH3)2 | |
| L-3 | — | OC2H5 | H | CH3 | N | CH(OC2H5)2 | |
| L-3 | — | Cl | H | CH3 | CH | CH(—OCH2CH2O—) | |
| L-3 | — | SO2C2H5 | H | OCH3 | CH | CH(—OCH2CH2O—) | |
| L-3 | — | SO2CH3 | H | OCH3 | CH | CH(—OCH2CH2O—) | |
| L-2 | Cl | — | H | OCH3 | CH | C6H5 | |
| L-2 | OCH3 | — | H | OCH3 | N | C6H5 | |
| L-3 | — | SO2CH3 | H | CH3 | CH | C6H5 | |
| L-3 | — | Cl | H | OCH3 | CH | C6H5 | |

TABLE 3a

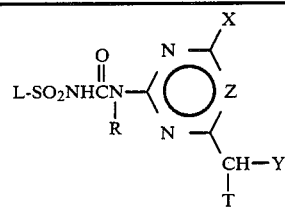

| L | R5 | R | X | T | Y | Z | m.p. (°C.) |
|---|---|---|---|---|---|---|---|
| L-4 | CH3 | H | OCH3 | H | SeCH3 | CH | |
| L-4 | CH3 | H | OCH3 | H | SePh | CH | |
| L-4 | CH2CH3 | H | OCH3 | H | SPh | CH | |
| L-4 | CH2CH2CH3 | H | OCH3 | H | SOPh | CH | |
| L-4 | F | H | OCH3 | H | SO2Ph | CH | |
| L-4 | Cl | H | CH3 | H | SeCH3 | CH | |
| L-4 | Cl | H | CH3 | H | SePh | CH | |
| L-4 | Br | H | CH3 | H | SPh | CH | |
| L-4 | Br | H | CH3 | H | SO2Ph | CH | |
| L-4 | NO2 | H | OCH3 | H | SeCH3 | CH | |

TABLE 3a-continued

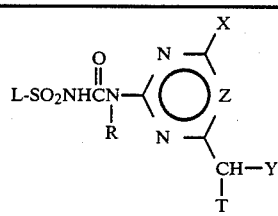

| L | R₅ | R | X | T | Y | Z | m.p. (°C.) |
|---|---|---|---|---|---|---|---|
| L-4 | NO₂ | H | OCH₃ | H. | SPh | CH | |
| L-4 | NO₂ | H | OCH₃ | H | SePh | CH | |
| L-4 | NO₂ | H | OCH₃ | H | SO₂Ph | CH | |
| L-4 | NO₂ | H | CH₃ | H | SeCH₃ | CH | |
| L-4 | NO₂ | H | CH₃ | H | SPh | CH | |
| L-4 | NO₂ | H | OCH₃ | SeCH₃ | SeCH₃ | CH | |
| L-4 | NO₂ | H | OCH₃ | H | OPh | CH | |
| L-4 | NO₂ | H | OCH₃ | H | SeCH₃ | N | |
| L-4 | NO₂ | H | OCH₃ | H | SPh | N | |
| L-4 | NO₂ | H | CH₃ | SePh | SePh | N | |
| L-4 | CO₂CH₃ | H | OCH₃ | H | SeCH₃ | CH | |
| L-4 | CO₂CH₃ | H | OCH₃ | H | SePh | CH | |
| L-4 | CO₂CH₃ | H | OCH₃ | H | SPh | CH | |
| L-4 | CO₂CH₃ | H | OCH₃ | H | SOPh | CH | |
| L-4 | CO₂CH₃ | H | OCH₃ | H | SO₂Ph | CH | |
| L-4 | CO₂CH₃ | H | OCH₃ | H | OPh | CH | |
| L-4 | CO₂CH₃ | H | OCH₃ | SeCH₃ | SeCH₃ | CH | |
| L-4 | CO₂CH₃ | H | OCH₃ | SPh | SPh | CH | |
| L-4 | CO₂CH₃ | H | OCH₃ | SeCH₃ | SePh | CH | |
| L-4 | CO₂CH₃ | H | OCH₃ | H | SPh | N | |
| L-4 | CO₂CH₃ | H | OCH₃ | H | SePh | N | |
| L-4 | CO₂CH₃ | H | OCH₃ | H | SeCH₃ | N | |
| L-4 | CO₂CH₃ | H | OCH₃ | H | SO₂Ph | N | |
| L-4 | CO₂CH₃ | H | OCH₃ | SeCH₃ | SeCH₃ | N | |
| L-4 | CO₂CH₃ | H | OCH₃ | SePh | SePh | N | |
| L-4 | CO₂CH₃ | H | OCH₃ | SPh | SPh | N | |
| L-4 | CO₂CH₃ | CH₃ | OCH₃ | H | SePh | CH | |
| L-4 | CO₂CH₃ | CH₃ | OCH₃ | H | SPH | CH | |
| L-4 | CO₂CH₃ | H | CH₃ | H | SeCH₃ | CH | |
| L-4 | CO₂CH₃ | H | CH₃ | H | SePh | CH | |
| L-4 | CO₂CH₃ | H | CH₃ | H | SPh | CH | |
| L-4 | CO₂CH₃ | H | CH₃ | H | SOPh | CH | |
| L-4 | CO₂CH₃ | H | CH₃ | H | SO₂Ph | CH | |
| L-4 | CO₂CH₃ | H | CH₃ | SeCH₃ | SeCH₃ | CH | |
| L-4 | CO₂CH₃ | H | CH₃ | SeCH₃ | SePh | CH | |
| L-4 | CO₂CH₃ | H | CH₃ | SeCH₃ | SPh | CH | |
| L-4 | CO₂CH₃ | H | CH₃ | SPh | SO₂Ph | CH | |
| L-4 | CO₂CH₃ | H | CH₃ | H | SeCH₃ | N | |
| L-4 | CO₂CH₃ | H | CH₃ | H | SePh | N | |
| L-4 | CO₂CH₃ | H | CH₃ | H | SO₂Ph | N | |
| L-4 | CO₂CH₃ | H | CH₃ | H | OPh | CH | |
| L-4 | CO₂CH₃ | H | OCH₂CH₃ | H | SPh | CH | |
| L-4 | CO₂CH₃ | H | F | H | SPh | CH | |
| L-4 | CO₂CH₃ | H | Cl | H | SPh | CH | |
| L-4 | CO₂CH₃ | H | CF₃ | H | SeCH₃ | CH | |
| L-4 | CO₂CH₃ | H | CF₃ | H | SePh | CH | |
| L-4 | CO₂CH₃ | H | OCHF₂ | H | SeCH₃ | CH | |
| L-4 | CO₂CH₃ | H | OCHF₂ | H | SPh | CH | |
| L-4 | CO₂CH₃ | H | Br | H | SPh | CH | |
| L-4 | CO₂CH₂CH₃ | H | OCH₃ | H | SeCH₃ | CH | |
| L-4 | CO₂CH₂CH₃ | H | OCH₃ | H | SePh | CH | |
| L-4 | CO₂CH₂CH₃ | H | OCH₃ | H | SPh | CH | |
| L-4 | CO₂CH₂CH₃ | H | OCH₃ | H | SO₂Ph | CH | |
| L-4 | CO₂CH₂CH₃ | H | OCH₃ | SPh | SPh | CH | |
| L-4 | CO₂CH₂CH₃ | H | CH₃ | H | SPh | N | |
| L-4 | CO₂CH₂CH₃ | H | OCH₃ | H | SPh | CH | |
| L-4 | CO₂CH₂CH₂CH₃ | H | OCH₃ | H | SeCH₃ | CH | |
| L-4 | CO₂CH₂CH₃ | H | CH₃ | H | SeCH₃ | CH | |
| L-4 | CO₂CH₂CH₃ | H | CH₃ | H | SePh | CH | |
| L-4 | CO₂CH₂CH₃ | H | CH₃ | H | SPh | CH | |
| L-4 | SO₂N(CH₃)₂ | H | OCH₃ | H | SeCH₃ | CH | |
| L-4 | SO₂N(CH₃)₂ | H | OCH₃ | H | SePh | CH | |
| L-4 | SO₂N(CH₃)₂ | H | OCH₃ | H | SPh | CH | |
| L-4 | SO₂N(CH₃)₂ | H | OCH₃ | H | SO₂Ph | CH | |
| L-4 | SO₂N(CH₃)₂ | H | OCH₃ | H | SPh | N | |
| L-4 | SO₂N(CH₃)₂ | H | OCH₃ | SeCH₃ | SeCH₃ | CH | |
| L-4 | SO₂N(CH₃)₂ | H | OCH₃ | SePh | SePh | CH | |
| L-4 | SO₂N(CH₃)₂ | H | OCH₃ | SPh | SPh | CH | |
| L-4 | SO₂N(CH₃)₂ | H | OCH₃ | H | OPh | CH | |
| L-4 | SO₂N(CH₃)₂ | H | CH₃ | H | SeCH₃ | CH | |

TABLE 3a-continued

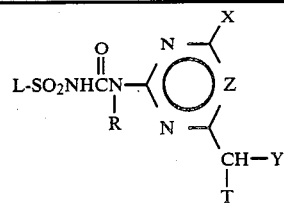

| L | R₅ | R | X | T | Y | Z | m.p. (°C.) |
|---|---|---|---|---|---|---|---|
| L-4 | SO₂N(CH₃)₂ | H | CH₃ | H | SePh | CH | |
| L-4 | SO₂N(CH₃)₂ | H | CH₃ | H | SPh | CH | |
| L-4 | SO₂N(CH₃)₂ | H | CH₃ | H | SO₂Ph | CH | |
| L-4 | SO₂N(CH₃)₂ | H | CH₃ | H | SeCH₃ | N | |
| L-4 | SO₂N(CH₃)₂ | H | CH₃ | SeCH₃ | SeCH₃ | CH | |
| L-4 | SO₂N(CH₃)₂ | H | CH₃ | SPh | SPh | CH | |
| L-4 | SO₂N(CH₂CH₃)₂ | H | OCH₃ | H | SeCH₃ | CH | |
| L-4 | SO₂N(CH₂CH₃)₂ | H | OCH₃ | H | SePh | CH | |
| L-4 | SO₂N(CH₂CH₃)₂ | H | OCH₃ | H | SPh | CH | |
| L-4 | SO₂N(CH₂CH₃)₂ | H | OCH₃ | H | SO₂Ph | CH | |
| L-4 | SO₂N(CH₂CH₃)₂ | H | OCH₃ | H | SeCH₃ | N | |
| L-4 | SO₂N(CH₂CH₃)₂ | H | OCH₃ | H | SePh | N | |
| L-4 | SO₂N(CH₂CH₃)₂ | H | OCH₃ | H | SPh | N | |
| L-4 | SO₂N(CH₂CH₃)₂ | H | CH₃ | H | SeCH₃ | N | |
| L-4 | SO₂N(CH₂CH₃)₂ | H | CH₃ | H | SeCH₃ | CH | |
| L-4 | SO₂N(CH₂CH₃)₂ | H | CH₃ | H | SPh | CH | |
| L-4 | SO₂N(OCH₃)CH₃ | H | OCH₃ | H | SeCH₃ | CH | |
| L-4 | SO₂N(OCH₃)CH₃ | H | OCH₃ | H | SePh | CH | |
| L-4 | SO₂N(OCH₃)CH₃ | H | OCH₃ | H | SPh | CH | |
| L-4 | SO₂N(OCH₃)CH₃ | H | OCH₃ | H | SO₂Ph | CH | |
| L-4 | SO₂N(OCH₃)CH₃ | H | CH₃ | H | SePh | CH | |
| L-4 | SCH₃ | H | OCH₃ | H | SeCH₃ | CH | |
| L-4 | SCH₃ | H | OCH₃ | H | SePh | CH | |
| L-4 | SCH₃ | H | OCH₃ | H | SPh | CH | |
| L-4 | SOCH₃ | H | OCH₃ | H | SePh | CH | |
| L-4 | SO₂CH₃ | H | OCH₃ | H | SeCH₃ | CH | |
| L-4 | SO₂CH₃ | H | OCH₃ | H | SePh | CH | |
| L-4 | SO₂CH₃ | H | OCH₃ | H | SPh | CH | |
| L-4 | SO₂CH₃ | H | OCH₃ | H | SO₂Ph | CH | |
| L-4 | SO₂CH₃ | H | OCH₃ | H | SePh | N | |
| L-5 | CH₃ | H | OCH₃ | H | SeCH₃ | CH | |
| L-5 | CH₃ | H | OCH₃ | H | SePh | CH | |
| L-5 | CH₂CH₃ | H | OCH₃ | H | SPh | CH | |
| L-5 | CH₂CH₂CH₃ | H | OCH₃ | H | SOPh | CH | |
| L-5 | F | H | OCH₃ | H | SO₂Ph | CH | |
| L-5 | Cl | H | CH₃ | H | SeCH₃ | CH | |
| L-5 | Cl | H | CH₃ | H | SePh | CH | |
| L-5 | Br | H | CH₃ | H | SPh | CH | |
| L-5 | Br | H | CH₃ | H | SO₂Ph | CH | |
| L-5 | NO₂ | H | OCH₃ | H | SeCH₃ | CH | |
| L-5 | NO₂ | H | OCH₃ | H | SPh | CH | |
| L-5 | NO₂ | H | OCH₃ | H | SePh | CH | |
| L-5 | NO₂ | H | OCH₃ | H | SO₂Ph | CH | |
| L-5 | NO₂ | H | CH₃ | H | SeCH₃ | CH | |
| L-5 | NO₂ | H | CH₃ | H | SPh | CH | |
| L-5 | NO₂ | H | OCH₃ | SeCH₃ | SeCH₃ | CH | |
| L-5 | NO₂ | H | OCH₃ | H | OPh | CH | |
| L-5 | NO₂ | H | OCH₃ | H | SeCH₃ | N | |
| L-5 | NO₂ | H | OCH₃ | H | SPh | N | |
| L-5 | NO₂ | H | CH₃ | SePh | SePh | N | |
| L-5 | CO₂CH₃ | H | OCH₃ | H | SeCH₃ | CH | |
| L-5 | CO₂CH₃ | H | OCH₃ | H | SePh | CH | |
| L-5 | CO₂CH₃ | H | OCH₃ | H | SPh | CH | |
| L-5 | CO₂CH₃ | H | OCH₃ | H | SOPh | CH | |
| L-5 | CO₂CH₃ | H | OCH₃ | H | SO₂Ph | CH | |
| L-5 | CO₂CH₃ | H | OCH₃ | H | OPh | CH | |
| L-5 | CO₂CH₃ | H | OCH₃ | SeCH₃ | SeCH₃ | CH | |
| L-5 | CO₂CH₃ | H | OCH₃ | SPh | SPh | CH | |
| L-5 | CO₂CH₃ | H | OCH₃ | SeCH₃ | SePh | CH | |
| L-5 | CO₂CH₃ | H | OCH₃ | H | SPh | N | |
| L-5 | CO₂CH₃ | H | OCH₃ | H | SePh | N | |
| L-5 | CO₂CH₃ | H | OCH₃ | H | SeCH₃ | N | |
| L-5 | CO₂CH₃ | H | OCH₃ | H | SO₂Ph | N | |
| L-5 | CO₂CH₃ | H | OCH₃ | SeCH₃ | SeCH₃ | N | |
| L-5 | CO₂CH₃ | H | OCH₃ | SePh | SePh | N | |
| L-5 | CO₂CH₃ | H | OCH₃ | SPh | SPh | N | |
| L-5 | CO₂CH₃ | CH₃ | OCH₃ | H | SePh | CH | |
| L-5 | CO₂CH₃ | CH₃ | OCH₃ | H | SPh | CH | |
| L-5 | CO₂CH₃ | H | CH₃ | H | SeCH₃ | CH | |
| L-5 | CO₂CH₃ | H | CH₃ | H | SePh | CH | |

TABLE 3a-continued

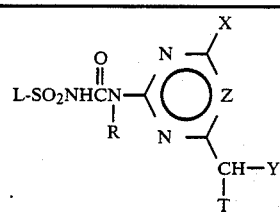

| L | R₅ | R | X | T | Y | Z | m.p. (°C.) |
|---|---|---|---|---|---|---|---|
| L-5 | CO₂CH₃ | H | CH₃ | H | SPh | CH | |
| L-5 | CO₂CH₃ | H | CH₃ | H | SOPh | CH | |
| L-5 | CO₂CH₃ | H | CH₃ | H | SO₂Ph | CH | |
| L-5 | CO₂CH₃ | H | CH₃ | SeCH₃ | SeCH₃ | CH | |
| L-5 | CO₂CH₃ | H | CH₃ | SeCH₃ | SePh | CH | |
| L-5 | CO₂CH₃ | H | CH₃ | SeCH₃ | SPh | CH | |
| L-5 | CO₂CH₃ | H | CH₃ | SPh | SO₂Ph | CH | |
| L-5 | CO₂CH₃ | H | CH₃ | H | SeCH₃ | N | |
| L-5 | CO₂CH₃ | H | CH₃ | H | SePh | N | |
| L-5 | CO₂CH₃ | H | CH₃ | H | SO₂Ph | N | |
| L-5 | CO₂CH₃ | H | CH₃ | H | OPh | CH | |
| L-5 | CO₂CH₃ | H | OCH₂CH₃ | H | SPh | CH | |
| L-5 | CO₂CH₃ | H | F | H | SPh | CH | |
| L-5 | CO₂CH₃ | H | Cl | H | SPh | CH | |
| L-5 | CO₂CH₃ | H | CF₃ | H | SeCH₃ | CH | |
| L-5 | CO₂CH₃ | H | CF₃ | H | SePh | CH | |
| L-5 | CO₂CH₃ | H | OCHF₂ | H | SeCH₃ | CH | |
| L-5 | CO₂CH₃ | H | OCHF₂ | H | SPh | CH | |
| L-5 | CO₂CH₃ | H | Br | H | SPh | CH | |
| L-5 | CO₂CH₂CH₃ | H | OCH₃ | H | SeCH₃ | CH | |
| L-5 | CO₂CH₂CH₃ | H | OCH₃ | H | SePh | CH | |
| L-5 | CO₂CH₂CH₃ | H | OCH₃ | H | SPh | CH | |
| L-5 | CO₂CH₂CH₃ | H | OCH₃ | H | SO₂Ph | CH | |
| L-5 | CO₂CH₂CH₃ | H | OCH₃ | SPh | SPh | CH | |
| L-5 | CO₂CH₂CH₃ | H | CH₃ | H | SPh | N | |
| L-5 | CO₂CH₂CH₂CH₃ | H | OCH₃ | H | SPh | CH | |
| L-5 | CO₂CH₂CH₂CH₃ | H | OCH₃ | H | SeCH₃ | CH | |
| L-5 | CO₂CH₂CH₂CH₃ | H | CH₃ | H | SeCH₃ | CH | |
| L-5 | CO₂CH₂CH₂CH₃ | H | CH₃ | H | SePh | CH | |
| L-5 | CO₂CH₂CH₂CH₃ | H | CH₃ | H | SPh | CH | |
| L-5 | SO₂N(CH₃)₂ | H | OCH₃ | H | SeCH₃ | CH | |
| L-5 | SO₂N(CH₃)₂ | H | OCH₃ | H | SePh | CH | |
| L-5 | SO₂N(CH₃)₂ | H | OCH₃ | H | SPh | CH | |
| L-5 | SO₂N(CH₃)₂ | H | OCH₃ | H | SO₂Ph | CH | |
| L-5 | SO₂N(CH₃)₂ | H | OCH₃ | H | SPh | N | |
| L-5 | SO₂N(CH₃)₂ | H | OCH₃ | SeCH₃ | SeCH₃ | CH | |
| L-5 | SO₂N(CH₃)₂ | H | OCH₃ | SePh | SePh | CH | |
| L-5 | SO₂N(CH₃)₂ | H | OCH₃ | SPh | SPh | CH | |
| L-5 | SO₂N(CH₃)₂ | H | OCH₃ | H | OPh | CH | |
| L-5 | SO₂N(CH₃)₂ | H | CH₃ | H | SeCH₃ | CH | |
| L-5 | SO₂N(CH₃)₂ | H | CH₃ | H | SePh | CH | |
| L-5 | SO₂N(CH₃)₂ | H | CH₃ | H | SPh | CH | |
| L-5 | SO₂N(CH₃)₂ | H | CH₃ | H | SO₂Ph | CH | |
| L-5 | SO₂N(CH₃)₂ | H | CH₃ | H | SeCH₃ | N | |
| L-5 | SO₂N(CH₃)₂ | H | CH₃ | SeCH₃ | SeCH₃ | CH | |
| L-5 | SO₂N(CH₃)₂ | H | CH₃ | SPh | SPh | CH | |
| L-5 | SO₂N(CH₂CH₃)₂ | H | OCH₃ | H | SeCH₃ | CH | |
| L-5 | SO₂N(CH₂CH₃)₂ | H | OCH₃ | H | SePh | CH | |
| L-5 | SO₂N(CH₂CH₃)₂ | H | OCH₃ | H | SPh | CH | |
| L-5 | SO₂N(CH₂CH₃)₂ | H | OCH₃ | H | SO₂Ph | CH | |
| L-5 | SO₂N(CH₂CH₃)₂ | H | OCH₃ | H | SeCH₃ | N | |
| L-5 | SO₂N(CH₂CH₃)₂ | H | OCH₃ | H | SePh | N | |
| L-5 | SO₂N(CH₂CH₃)₂ | H | OCH₃ | H | SPh | N | |
| L-5 | SO₂N(CH₂CH₃)₂ | H | CH₃ | H | SeCH₃ | N | |
| L-5 | SO₂N(CH₂CH₃)₂ | H | CH₃ | H | SeCH₃ | CH | |
| L-5 | SO₂N(CH₂CH₃)₂ | H | CH₃ | H | SPh | CH | |
| L-5 | SO₂N(OCH₃)CH₃ | H | OCH₃ | H | SeCH₃ | CH | |
| L-5 | SO₂N(OCH₃)CH₃ | H | OCH₃ | H | SePh | CH | |
| L-5 | SO₂N(OCH₃)CH₃ | H | OCH₃ | H | SPh | CH | |
| L-5 | SO₂N(OCH₃)CH₃ | H | OCH₃ | H | SO₂Ph | CH | |
| L-5 | SO₂N(OCH₃)CH₃ | H | CH₃ | H | SePh | CH | |
| L-5 | SCH₃ | H | OCH₃ | H | SeCH₃ | CH | |
| L-5 | SCH₃ | H | OCH₃ | H | SePh | CH | |
| L-5 | SCH₃ | H | OCH₃ | H | SPh | CH | |
| L-5 | SOCH₃ | H | OCH₃ | H | SePh | CH | |
| L-5 | SO₂CH₃ | H | OCH₃ | H | SeCH₃ | CH | |
| L-5 | SO₂CH₃ | H | OCH₃ | H | SePh | CH | |
| L-5 | SO₂CH₃ | H | OCH₃ | H | SPh | CH | |
| L-5 | SO₂CH₃ | H | OCH₃ | H | SO₂Ph | CH | |
| L-5 | SO₂CH₃ | H | OCH₃ | H | SePh | N | |

TABLE 3a-continued

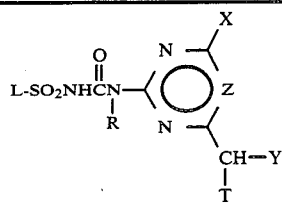

| L | R5 | R | X | T | Y | Z | m.p. (°C.) |
|---|---|---|---|---|---|---|---|
| L-6 | CH3 | H | OCH3 | H | SeCH3 | CH | |
| L-6 | CH3 | H | OCH3 | H | SePh | CH | |
| L-6 | CH2CH3 | H | OCH3 | H | SPh | CH | |
| L-6 | CH2CH2CH3 | H | OCH3 | H | SOPh | CH | |
| L-6 | F | H | OCH3 | H | SO2Ph | CH | |
| L-6 | Cl | H | CH3 | H | SeCH3 | CH | |
| L-6 | Cl | H | CH3 | H | SePh | CH | |
| L-6 | Br | H | CH3 | H | SPh | CH | |
| L-6 | Br | H | CH3 | H | SO2Ph | CH | |
| L-6 | NO2 | H | OCH3 | H | SeCH3 | CH | |
| L-6 | NO2 | H | OCH3 | H | SPh | CH | |
| L-6 | NO2 | H | OCH3 | H | SePh | CH | |
| L-6 | NO2 | H | OCH3 | H | SO2Ph | CH | |
| L-6 | NO2 | H | CH3 | H | SeCH3 | CH | |
| L-6 | NO2 | H | CH3 | H | SPh | CH | |
| L-6 | NO2 | H | OCH3 | SeCH3 | SeCH3 | CH | |
| L-6 | NO2 | H | OCH3 | H | OPh | CH | |
| L-6 | NO2 | H | OCH3 | H | SeCH3 | N | |
| L-6 | NO2 | H | OCH3 | H | SPh | N | |
| L-6 | NO2 | H | CH3 | SePh | SePh | N | |
| L-6 | CO2CH3 | H | OCH3 | H | SeCH3 | CH | |
| L-6 | CO2CH3 | H | OCH3 | H | SePh | CH | |
| L-6 | CO2CH3 | H | OCH3 | H | SPh | CH | |
| L-6 | CO2CH3 | H | OCH3 | H | SOPh | CH | |
| L-6 | CO2CH3 | H | OCH3 | H | SO2Ph | CH | |
| L-6 | CO2CH3 | H | OCH3 | H | OPh | CH | |
| L-6 | CO2CH3 | H | OCH3 | SeCH3 | SeCH3 | CH | |
| L-6 | CO2CH3 | H | OCH3 | SPh | SPh | CH | |
| L-6 | CO2CH3 | H | OCH3 | SeCH3 | SePh | CH | |
| L-6 | CO2CH3 | H | OCH3 | H | SPh | N | |
| L-6 | CO2CH3 | H | OCH3 | H | SePh | N | |
| L-6 | CO2CH3 | H | OCH3 | H | SeCH3 | N | |
| L-6 | CO2CH3 | H | OCH3 | H | SO2Ph | N | |
| L-6 | CO2CH3 | H | OCH3 | SeCH3 | SeCH3 | N | |
| L-6 | CO2CH3 | H | OCH3 | SePh | SePh | N | |
| L-6 | CO2CH3 | H | OCH3 | SPh | SPh | N | |
| L-6 | CO2CH3 | CH3 | OCH3 | H | SePh | CH | |
| L-6 | CO2CH3 | CH3 | OCH3 | H | SPh | CH | |
| L-6 | CO2CH3 | H | CH3 | H | SeCH3 | CH | |
| L-6 | CO2CH3 | H | CH3 | H | SePh | CH | |
| L-6 | CO2CH3 | H | CH3 | H | SPh | CH | |
| L-6 | CO2CH3 | H | CH3 | H | SOPh | CH | |
| L-6 | CO2CH3 | H | CH3 | H | SO2Ph | CH | |
| L-6 | CO2CH3 | H | CH3 | SeCH3 | SeCH3 | CH | |
| L-6 | CO2CH3 | H | CH3 | SeCH3 | SePh | CH | |
| L-6 | CO2CH3 | H | CH3 | SeCH3 | SPh | CH | |
| L-6 | CO2CH3 | H | CH3 | SPh | SO2Ph | CH | |
| L-6 | CO2CH3 | H | CH3 | H | SeCH3 | N | |
| L-6 | CO2CH3 | H | CH3 | H | SePh | N | |
| L-6 | CO2CH3 | H | CH3 | H | SO2Ph | N | |
| L-6 | CO2CH3 | H | CH3 | H | OPh | CH | |
| L-6 | CO2CH3 | H | OCH2CH3 | H | SPh | CH | |
| L-6 | CO2CH3 | H | F | H | SPh | CH | |
| L-6 | CO2CH3 | H | Cl | H | SPh | CH | |
| L-6 | CO2CH3 | H | CF3 | H | SeCH3 | CH | |
| L-6 | CO2CH3 | H | CF3 | H | SePh | CH | |
| L-6 | CO2CH3 | H | OCHF2 | H | SeCH3 | CH | |
| L-6 | CO2CH3 | H | OCHF2 | H | SPh | CH | |
| L-6 | CO2CH3 | H | Br | H | SPh | CH | |
| L-6 | CO2CH2CH3 | H | OCH3 | H | SeCH3 | CH | |
| L-6 | CO2CH2CH3 | H | OCH3 | H | SePh | CH | |
| L-6 | CO2CH2CH3 | H | OCH3 | H | SPh | CH | |
| L-6 | CO2CH2CH3 | H | OCH3 | H | SO2Ph | CH | |
| L-6 | CO2CH2CH3 | H | OCH3 | SPh | SPh | CH | |
| L-6 | CO2CH2CH3 | H | CH3 | H | SPh | N | |
| L-6 | CO2CH2CH2CH3 | H | OCH3 | H | SPh | CH | |
| L-6 | CO2CH2CH2CH3 | H | OCH3 | H | SeCH3 | CH | |
| L-6 | CO2CH2CH3 | H | CH3 | H | SeCH3 | CH | |
| L-6 | CO2CH2CH3 | H | CH3 | H | SePh | CH | |
| L-6 | CO2CH2CH3 | H | CH3 | H | SPH | CH | |

TABLE 3a-continued

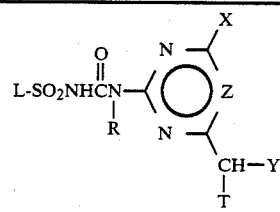

| L | R₅ | R | X | T | Y | Z | m.p. (°C.) |
|---|---|---|---|---|---|---|---|
| L-6 | SO$_2$N(CH$_3$)$_2$ | H | OCH$_3$ | H | SeCH$_3$ | CH | |
| L-6 | SO$_2$N(CH$_3$)$_2$ | H | OCH$_3$ | H | SePh | CH | |
| L-6 | SO$_2$N(CH$_3$)$_2$ | H | OCH$_3$ | H | SPh | CH | |
| L-6 | SO$_2$N(CH$_3$)$_2$ | H | OCH$_3$ | H | SO$_2$Ph | CH | |
| L-6 | SO$_2$N(CH$_3$)$_2$ | H | OCH$_3$ | H | SPh | N | |
| L-6 | SO$_2$N(CH$_3$)$_2$ | H | OCH$_3$ | SeCH$_3$ | SeCH$_3$ | CH | |
| L-6 | SO$_2$N(CH$_3$)$_2$ | H | OCH$_3$ | SePh | SePh | CH | |
| L-6 | SO$_2$N(CH$_3$)$_2$ | H | OCH$_3$ | SPh | SPh | CH | |
| L-6 | SO$_2$N(CH$_3$)$_2$ | H | OCH$_3$ | H | OPh | CH | |
| L-6 | SO$_2$N(CH$_3$)$_2$ | H | CH$_3$ | H | SeCH$_3$ | CH | |
| L-6 | SO$_2$N(CH$_3$)$_2$ | H | CH$_3$ | H | SePh | CH | |
| L-6 | SO$_2$N(CH$_3$)$_2$ | H | CH$_3$ | H | SPh | CH | |
| L-6 | SO$_2$N(CH$_3$)$_2$ | H | CH$_3$ | H | SO$_2$Ph | CH | |
| L-6 | SO$_2$N(CH$_3$)$_2$ | H | CH$_3$ | H | SeCH$_3$ | N | |
| L-6 | SO$_2$N(CH$_3$)$_2$ | H | CH$_3$ | SeCH$_3$ | SeCH$_3$ | CH | |
| L-6 | SO$_2$N(CH$_3$)$_2$ | H | CH$_3$ | SPh | SPh | CH | |
| L-6 | SO$_2$N(CH$_2$CH$_3$)$_2$ | H | OCH$_3$ | H | SeCH$_3$ | CH | |
| L-6 | SO$_2$N(CH$_2$CH$_3$)$_2$ | H | OCH$_3$ | H | SePh | CH | |
| L-6 | SO$_2$N(CH$_2$CH$_3$)$_2$ | H | OCH$_3$ | H | SPh | CH | |
| L-6 | SO$_2$N(CH$_2$CH$_3$)$_2$ | H | OCH$_3$ | H | SO$_2$Ph | CH | |
| L-6 | SO$_2$N(CH$_2$CH$_3$)$_2$ | H | OCH$_3$ | H | SeCH$_3$ | N | |
| L-6 | SO$_2$N(CH$_2$CH$_3$)$_2$ | H | OCH$_3$ | H | SePh | N | |
| L-6 | SO$_2$N(CH$_2$CH$_3$)$_2$ | H | OCH$_3$ | H | SPh | N | |
| L-6 | SO$_2$N(CH$_2$CH$_3$)$_2$ | H | CH$_3$ | H | SeCH$_3$ | N | |
| L-6 | SO$_2$N(CH$_2$CH$_3$)$_2$ | H | CH$_3$ | H | SeCH$_3$ | CH | |
| L-6 | SO$_2$N(CH$_2$CH$_3$)$_2$ | H | CH$_3$ | H | SPh | CH | |
| L-6 | SO$_2$N(OCH$_3$)CH$_3$ | H | OCH$_3$ | H | SeCH$_3$ | CH | |
| L-6 | SO$_2$N(OCH$_3$)CH$_3$ | H | OCH$_3$ | H | SePh | CH | |
| L-6 | SO$_2$N(OCH$_3$)CH$_3$ | H | OCH$_3$ | H | SPh | CH | |
| L-6 | SO$_2$N(OCH$_3$)CH$_3$ | H | OCH$_3$ | H | SO$_2$Ph | CH | |
| L-6 | SO$_2$N(OCH$_3$)CH$_3$ | H | CH$_3$ | H | SePh | CH | |
| L-6 | SCH$_3$ | H | OCH$_3$ | H | SeCH$_3$ | CH | |
| L-6 | SCH$_3$ | H | OCH$_3$ | H | SePh | CH | |
| L-6 | SCH$_3$ | H | OCH$_3$ | H | SPh | CH | |
| L-6 | SOCH$_3$ | H | OCH$_3$ | H | SePh | CH | |
| L-6 | SO$_2$CH$_3$ | H | OCH$_3$ | H | SeCH$_3$ | CH | |
| L-6 | SO$_2$CH$_3$ | H | OCH$_3$ | H | SePh | CH | |
| L-6 | SO$_2$CH$_3$ | H | OCH$_3$ | H | SPh | CH | |
| L-6 | SO$_2$CH$_3$ | H | OCH$_3$ | H | SO$_2$Ph | CH | |
| L-6 | SO$_2$CH$_3$ | H | OCH$_3$ | H | SePh | N | |
| L-4 | CH$_3$ | H | OCH$_3$ | H | CH$_2$OH | CH | |
| L-5 | Br | H | OCH$_3$ | H | CH$_2$OSi(CH$_3$)$_3$ | CH | |
| L-6 | CO$_2$CH$_3$ | H | OCH$_3$ | H | CH$_2$OSi(CH$_3$)$_3$ | CH | |
| L-6 | CO$_2$CH$_3$ | H | OCH$_3$ | H | CH$_2$OH | N | |
| L-6 | CO$_2$CH$_3$ | H | OCH$_3$ | H | OSi(CH$_3$)$_3$ | N | |

TABLE 3b

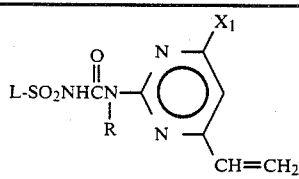

| L | R₅ | R | X₁ | m.p. (°C.) |
|---|---|---|---|---|
| L-4 | CH$_3$ | H | CH$_3$ | |
| L-4 | CH$_3$ | H | OCH$_3$ | |
| L-4 | CH$_2$CH$_3$ | H | CH$_3$ | |
| L-4 | CH$_2$CH$_3$ | H | OCH$_3$ | |
| L-4 | CH$_2$CH$_2$CH$_3$ | H | OCH$_3$ | |
| L-4 | F | H | OCH$_3$ | |
| L-4 | Cl | H | OCH$_3$ | |
| L-4 | Cl | H | CH$_3$ | |
| L-4 | Br | H | OCH$_3$ | |
| L-4 | NO$_2$ | H | CH$_3$ | |

TABLE 3b-continued

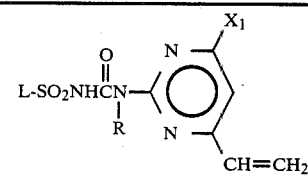

| L | R₅ | R | X₁ | m.p. (°C.) |
|---|---|---|---|---|
| L-4 | NO$_2$ | H | OCH$_3$ | |
| L-4 | NO$_2$ | H | OCH$_2$CH$_3$ | |
| L-4 | CO$_2$CH$_3$ | H | OCH$_3$ | |
| L-4 | CO$_2$CH$_3$ | H | CH$_3$ | |
| L-4 | CO$_2$CH$_3$ | H | OCH$_2$CH$_3$ | |
| L-4 | CO$_2$CH$_3$ | CH$_3$ | OCH$_3$ | |
| L-4 | SO$_2$N(CH$_3$)$_2$ | H | CH$_3$ | |
| L-4 | SO$_2$N(CH$_3$)$_2$ | H | OCH$_3$ | |
| L-4 | SO$_2$N(CH$_3$)$_2$ | H | OCH$_2$CH$_3$ | |
| L-4 | SO$_2$N(CH$_2$CH$_3$)$_2$ | H | OCH$_3$ | |

TABLE 3b-continued

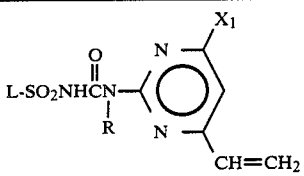

| L | R₅ | R | X₁ | m.p. (°C.) |
|---|---|---|---|---|
| L-4 | SO₂N(OCH₃)CH₃ | H | OCH₃ | |
| L-4 | SCH₃ | H | OCH₃ | |
| L-4 | SOCH₃ | H | OCH₃ | |
| L-4 | SO₂CH₃ | H | CH₃ | |
| L-4 | SO₂CH₃ | H | OCH₃ | |
| L-4 | SO₂CH₃ | H | OCH₂CH₃ | |
| L-5 | CH₃ | H | CH₃ | |
| L-5 | CH₃ | H | OCH₃ | |
| L-5 | CH₂CH₃ | H | CH₃ | |
| L-5 | CH₂CH₃ | H | OCH₃ | |
| L-5 | CH₂CH₂CH₃ | H | OCH₃ | |
| L-5 | F | H | OCH₃ | |
| L-5 | Cl | H | OCH₃ | |
| L-5 | Cl | H | CH₃ | |
| L-5 | Br | H | OCH₃ | |
| L-5 | NO₂ | H | CH₃ | |
| L-5 | NO₂ | H | OCH₃ | |
| L-5 | NO₂ | H | OCH₂CH₃ | |
| L-5 | CO₂CH₃ | H | OCH₃ | |
| L-5 | CO₂CH₃ | H | CH₃ | |
| L-5 | CO₂CH₃ | H | OCH₂CH₃ | |
| L-5 | CO₂CH₃ | CH₃ | OCH₃ | |
| L-5 | SO₂N(CH₃)₂ | H | CH₃ | |
| L-5 | SO₂N(CH₃)₂ | H | OCH₃ | |
| L-5 | SO₂N(CH₃)₂ | H | OCH₂CH₃ | |
| L-5 | SO₂N(CH₂CH₃)₂ | H | OCH₃ | |
| L-5 | SO₂N(OCH₃)CH₃ | H | OCH₃ | |
| L-5 | SCH₃ | H | OCH₃ | |
| L-5 | SOCH₃ | H | OCH₃ | |
| L-5 | SO₂CH₃ | H | CH₃ | |
| L-5 | SO₂CH₃ | H | OCH₃ | |
| L-5 | SO₂CH₃ | H | OCH₂CH₃ | |
| L-6 | CH₃ | H | CH₃ | |
| L-6 | CH₃ | H | OCH₃ | |
| L-6 | CH₂CH₃ | H | CH₃ | |
| L-6 | CH₂CH₃ | H | OCH₃ | |
| L-6 | CH₂CH₂CH₃ | H | OCH₃ | |
| L-6 | F | H | OCH₃ | |
| L-6 | Cl | H | OCH₃ | |
| L-6 | Cl | H | CH₃ | |
| L-6 | Br | H | OCH₃ | |
| L-6 | NO₂ | H | CH₃ | |
| L-6 | NO₂ | H | OCH₃ | |
| L-6 | NO₂ | H | OCH₂CH₃ | |
| L-6 | CO₂CH₃ | H | OCH₃ | |
| L-6 | CO₂CH₃ | H | CH₃ | |
| L-6 | CO₂CH₃ | H | OCH₂CH₃ | |
| L-6 | CO₂CH₃ | CH₃ | OCH₃ | |
| L-6 | SO₂N(CH₃)₂ | H | CH₃ | |
| L-6 | SO₂N(CH₃)₂ | H | OCH₃ | |
| L-6 | SO₂N(CH₃)₂ | H | OCH₂CH₃ | |
| L-6 | SO₂N(CH₂CH₃)₂ | H | OCH₃ | |
| L-6 | SO₂N(OCH₃)CH₃ | H | OCH₃ | |
| L-6 | SCH₃ | H | OCH₃ | |
| L-6 | SOCH₃ | H | OCH₃ | |
| L-6 | SO₂CH₃ | H | CH₃ | |
| L-6 | SO₂CH₃ | H | OCH₃ | |
| L-6 | SO₂CH₃ | H | OCH₂CH₃ | |

TABLE 3c

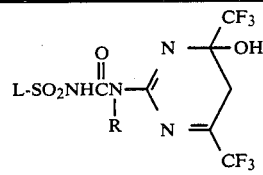

| L | R₅ | R | m.p. (°C.) |
|---|---|---|---|
| L-4 | CH₃ | H | |
| L-4 | CH₂CH₃ | H | |
| L-4 | CH₂CH₂CH₃ | H | |
| L-4 | F | H | |
| L-4 | Cl | H | |
| L-4 | Br | H | |
| L-4 | NO₂ | H | |
| L-4 | CO₂CH₃ | H | |
| L-4 | CO₂CH₂CH₃ | H | |
| L-4 | CO₂CH₂CH₂CH₃ | H | |
| L-4 | SO₂N(CH₃)₂ | H | |
| L-4 | SO₂N(CH₂CH₃)₂ | H | |
| L-4 | SO₂N(OCH₃)CH₃ | H | |
| L-4 | SCH₃ | H | |
| L-4 | SOCH₃ | H | |
| L-4 | SO₂CH₃ | H | |
| L-4 | CO₂CH₃ | CH₃ | |
| L-5 | CH₃ | H | |
| L-5 | CH₂CH₃ | H | |
| L-5 | CH₂CH₂CH₃ | H | |
| L-5 | F | H | |
| L-5 | Cl | H | |
| L-5 | Br | H | |
| L-5 | NO₂ | H | |
| L-5 | CO₂CH₃ | H | |
| L-5 | CO₂CH₂CH₃ | H | |
| L-5 | CO₂CH₂CH₂CH₃ | H | |
| L-5 | SO₂N(CH₃)₂ | H | |
| L-5 | SO₂N(CH₂CH₃)₂ | H | |
| L-5 | SO₂N(OCH₃)CH₃ | H | |
| L-5 | SCH₃ | H | |
| L-5 | SOCH₃ | H | |
| L-5 | SO₂CH₃ | H | |
| L-5 | CO₂CH₃ | CH₃ | |
| L-6 | CH₃ | H | |
| L-6 | CH₂CH₃ | H | |
| L-6 | CH₂CH₂CH₃ | H | |
| L-6 | F | H | |
| L-6 | Cl | H | |
| L-6 | Br | H | |
| L-6 | NO₂ | H | |
| L-6 | CO₂CH₃ | H | |
| L-6 | CO₂CH₂CH₃ | H | |
| L-6 | CO₂CH₂CH₂CH₃ | H | |
| L-6 | SO₂N(CH₃)₂ | H | |
| L-6 | SO₂N(CH₂CH₃)₂ | H | |
| L-6 | SO₂N(OCH₃)CH₃ | H | |
| L-6 | SCH₃ | H | |
| L-6 | SOCH₃ | H | |
| L-6 | SO₂CH₃ | H | |
| L-6 | CO₂CH₃ | CH₃ | |

TABLE 3d

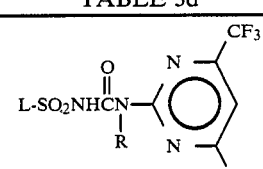

| L | R₅ | R | m.p. (°C.) |
|---|---|---|---|
| L-4 | CH₃ | H | |
| L-4 | CH₂CH₃ | H | |
| L-4 | CH₂CH₂CH₃ | H | |
| L-4 | F | H | |
| L-4 | Cl | H | |
| L-4 | Br | H | |

TABLE 3d-continued

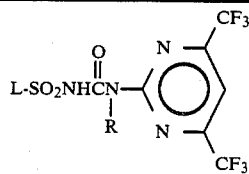

| L | R5 | R | m.p. (°C.) |
|---|---|---|---|
| L-4 | NO2 | H | |
| L-4 | CO2CH3 | H | |
| L-4 | CO2CH2CH3 | H | |
| L-4 | CO2CH2CH2CH3 | H | |
| L-4 | SO2N(CH3)2 | H | |
| L-4 | SO2N(CH2CH3)2 | H | |
| L-4 | SO2N(OCH3)CH3 | H | |
| L-4 | SCH3 | H | |
| L-4 | SOCH3 | H | |
| L-4 | SO2CH3 | H | |
| L-4 | CO2CH3 | CH3 | |
| L-5 | CH3 | H | |
| L-5 | CH2CH3 | H | |
| L-5 | CH2CH2CH3 | H | |
| L-5 | F | H | |
| L-5 | Cl | H | |
| L-5 | Br | H | |
| L-5 | NO2 | H | |
| L-5 | CO2CH3 | H | |
| L-5 | CO2CH2CH3 | H | |
| L-5 | CO2CH2CH2CH3 | H | |
| L-5 | SO2N(CH3)2 | H | |
| L-5 | SO2N(CH2CH3)2 | H | |
| L-5 | SO2N(OCH3)CH3 | H | |
| L-5 | SCH3 | H | |
| L-5 | SOCH3 | H | |
| L-5 | SO2CH3 | H | |
| L-5 | CO2CH3 | CH3 | |
| L-6 | CH3 | H | |
| L-6 | CH2CH3 | H | |
| L-6 | CH2CH2CH3 | H | |
| L-6 | F | H | |
| L-6 | Cl | H | |
| L-6 | Br | H | |
| L-6 | NO2 | H | |
| L-6 | CO2CH3 | H | |
| L-6 | CO2CH2CH3 | H | |
| L-6 | CO2CH2CH2CH3 | H | |
| L-6 | SO2N(CH3)2 | H | |
| L-6 | SO2N(CH2CH3)2 | H | |
| L-6 | SO2N(OCH3)CH3 | H | |
| L-6 | SCH3 | H | |
| L-6 | SOCH3 | H | |
| L-6 | SO2CH3 | H | |
| L-6 | CO2CH3 | CH3 | |

TABLE 3e

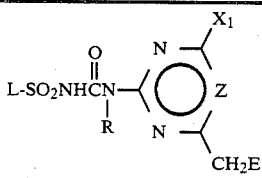

| L | R5 | R | X1 | E | Z | m.p. (°C.) |
|---|---|---|---|---|---|---|
| L-4 | CH3 | H | OCH3 | F | CH | |
| L-4 | CH3 | H | OCH3 | Cl | CH | |
| L-4 | CH3 | H | OCH3 | F | N | |
| L-4 | CH2CH3 | H | OCH3 | F | CH | |
| L-4 | CH2CH3 | H | OCH3 | Cl | CH | |
| L-4 | CH2CH3 | H | OCH3 | Br | CH | |
| L-4 | CH2CH3 | H | OCH3 | F | N | |
| L-4 | CH2CH3 | H | CH3 | F | CH | |
| L-4 | CH2CH2CH3 | H | OCH3 | F | CH | |
| L-4 | CH2CH2CH3 | H | CH3 | F | CH | |
| L-4 | F | H | OCH3 | F | CH | |

TABLE 3e-continued

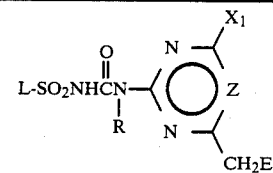

| L | R5 | R | X1 | E | Z | m.p. (°C.) |
|---|---|---|---|---|---|---|
| L-4 | F | H | OCH3 | Cl | CH | |
| L-4 | Cl | H | OCH3 | F | CH | |
| L-4 | Cl | H | CH3 | F | CH | |
| L-4 | Cl | H | OCH3 | F | N | |
| L-4 | NO2 | H | OCH3 | F | CH | |
| L-4 | NO2 | H | OCH3 | Cl | CH | |
| L-4 | NO2 | H | OCH3 | F | N | |
| L-4 | NO2 | H | CH3 | Br | CH | |
| L-4 | SO2N(CH3)2 | H | OCH3 | F | CH | |
| L-4 | SO2N(CH3)2 | H | OCH3 | Cl | CH | |
| L-4 | SO2N(CH3)2 | H | OCH3 | Br | CH | |
| L-4 | SO2N(CH3)2 | H | OCH3 | F | N | |
| L-4 | SO2N(CH3)2 | H | CH3 | F | CH | |
| L-4 | SO2N(CH3)2 | H | OCH2CH3 | F | CH | |
| L-4 | SO2N(CH3)2 | CH3 | OCH3 | F | CH | |
| L-4 | SO2N(CH2CH3)2 | H | OCH3 | F | CH | |
| L-4 | SO2N(CH2CH3)2 | H | OCH3 | F | N | |
| L-4 | SO2N(OCH3)CH3 | H | OCH3 | F | CH | |
| L-4 | SO2N(OCH3)CH3 | H | OCH3 | Cl | CH | |
| L-4 | SO2N(OCH3)CH3 | H | OCH3 | Br | CH | |
| L-4 | SO2N(OCH3)CH3 | H | CH3 | F | CH | |
| L-4 | SCH3 | H | OCH3 | F | CH | |
| L-4 | SCH3 | H | OCH3 | Cl | CH | |
| L-4 | SCH3 | H | OCH3 | Br | CH | |
| L-4 | SCH3 | H | CH3 | F | CH | |
| L-4 | SOCH3 | H | OCH3 | F | CH | |
| L-4 | SO2CH3 | H | OCH3 | F | CH | |
| L-4 | SO2CH3 | H | OCH3 | Cl | CH | |
| L-4 | SO2CH3 | H | OCH3 | Br | CH | |
| L-4 | SO2CH3 | H | OCH3 | F | N | |
| L-4 | SO2CH3 | H | CH3 | F | CH | |
| L-4 | SO2CH3 | H | CH3 | Cl | CH | |
| L-5 | CH3 | H | OCH3 | F | CH | |
| L-5 | CH3 | H | OCH3 | Cl | CH | |
| L-5 | CH3 | H | OCH3 | F | N | |
| L-5 | CH2CH3 | H | OCH3 | F | CH | |
| L-5 | CH2CH3 | H | OCH3 | Cl | CH | |
| L-5 | CH2CH3 | H | OCH3 | Br | CH | |
| L-5 | CH2CH3 | H | OCH3 | F | N | |
| L-5 | CH2CH3 | H | CH3 | F | CH | |
| L-5 | CH2CH2CH3 | H | OCH3 | F | CH | |
| L-5 | CH2CH2CH3 | H | CH3 | F | CH | |
| L-5 | F | H | OCH3 | F | CH | |
| L-5 | F | H | OCH3 | Cl | CH | |
| L-5 | Cl | H | OCH3 | F | CH | |
| L-5 | Cl | H | CH3 | F | CH | |
| L-5 | Cl | H | OCH3 | F | N | |
| L-5 | NO2 | H | OCH3 | F | CH | |
| L-5 | NO2 | H | OCH3 | Cl | CH | |
| L-5 | NO2 | H | OCH3 | F | N | |
| L-5 | NO2 | H | CH3 | Br | CH | |
| L-5 | SO2N(CH3)2 | H | OCH3 | F | CH | |
| L-5 | SO2N(CH3)2 | H | OCH3 | Cl | CH | |
| L-5 | SO2N(CH3)2 | H | OCH3 | Br | CH | |
| L-5 | SO2N(CH3)2 | H | OCH3 | F | N | |
| L-5 | SO2N(CH3)2 | H | CH3 | F | CH | |
| L-5 | SO2N(CH3)2 | H | OCH2CH3 | F | CH | |
| L-5 | SO2N(CH3)2 | CH3 | OCH3 | F | CH | |
| L-5 | SO2N(CH2CH3)2 | H | OCH3 | F | CH | |
| L-5 | SO2N(CH2CH3)2 | H | OCH3 | F | N | |
| L-5 | SO2N(OCH3)CH3 | H | OCH3 | F | CH | |
| L-5 | SO2N(OCH3)CH3 | H | OCH3 | Cl | CH | |
| L-5 | SO2N(OCH3)CH3 | H | OCH3 | Br | CH | |
| L-5 | SO2N(OCH3)CH3 | H | CH3 | F | CH | |
| L-5 | SCH3 | H | OCH3 | F | CH | |
| L-5 | SCH3 | H | OCH3 | Cl | CH | |
| L-5 | SCH3 | H | OCH3 | Br | CH | |
| L-5 | SCH3 | H | CH3 | F | CH | |
| L-5 | SOCH3 | H | OCH3 | F | CH | |
| L-5 | SO2CH3 | H | OCH3 | F | CH | |
| L-5 | SO2CH3 | H | OCH3 | Cl | CH | |

TABLE 3e-continued

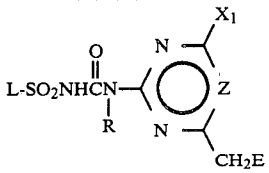

| L | R₅ | R | X₁ | E | Z | m.p. (°C.) |
|---|---|---|---|---|---|---|
| L-5 | SO₂CH₃ | H | OCH₃ | Br | CH | |
| L-5 | SO₂CH₃ | H | OCH₃ | F | N | |
| L-5 | SO₂CH₃ | H | CH₃ | F | CH | |
| L-5 | SO₂CH₃ | H | CH₃ | Cl | CH | |
| L-6 | CH₃ | H | OCH₃ | F | CH | |
| L-6 | CH₃ | H | OCH₃ | Cl | CH | |
| L-6 | CH₃ | H | OCH₃ | F | N | |
| L-6 | CH₂CH₃ | H | OCH₃ | F | CH | |
| L-6 | CH₂CH₃ | H | OCH₃ | Cl | CH | |
| L-6 | CH₂CH₃ | H | OCH₃ | Br | CH | |
| L-6 | CH₂CH₃ | H | OCH₃ | F | N | |
| L-6 | CH₂CH₃ | H | CH₃ | F | CH | |
| L-6 | CH₂CH₂CH₃ | H | OCH₃ | F | CH | |
| L-6 | CH₂CH₂CH₃ | H | CH₃ | F | CH | |
| L-6 | F | H | OCH₃ | F | CH | |
| L-6 | F | H | OCH₃ | Cl | CH | |
| L-6 | Cl | H | OCH₃ | F | CH | |
| L-6 | Cl | H | CH₃ | F | CH | |
| L-6 | Cl | H | OCH₃ | F | N | |
| L-6 | NO₂ | H | OCH₃ | F | CH | |
| L-6 | NO₂ | H | OCH₃ | Cl | CH | |
| L-6 | NO₂ | H | OCH₃ | F | N | |
| L-6 | NO₂ | H | CH₃ | Br | CH | |
| L-6 | SO₂N(CH₃)₂ | H | OCH₃ | F | CH | |
| L-6 | SO₂N(CH₃)₂ | H | OCH₃ | Cl | CH | |
| L-6 | SO₂N(CH₃)₂ | H | OCH₃ | Br | CH | |
| L-6 | SO₂N(CH₃)₂ | H | OCH₃ | F | N | |
| L-6 | SO₂N(CH₃)₂ | H | CH₃ | F | CH | |
| L-6 | SO₂N(CH₃)₂ | H | OCH₂CH₃ | F | CH | |
| L-6 | SO₂N(CH₃)₂ | CH₃ | OCH₃ | F | CH | |
| L-6 | SO₂N(CH₂CH₃)₂ | H | OCH₃ | F | CH | |
| L-6 | SO₂N(CH₂CH₃)₂ | H | OCH₃ | F | N | |
| L-6 | SO₂N(OCH₃)CH₃ | H | OCH₃ | F | CH | |
| L-6 | SO₂N(OCH₃)CH₃ | H | OCH₃ | Cl | CH | |
| L-6 | SO₂N(OCH₃)CH₃ | H | OCH₃ | Br | CH | |
| L-6 | SO₂N(OCH₃)CH₃ | H | CH₃ | F | CH | |
| L-6 | SCH₃ | H | OCH₃ | F | CH | |
| L-6 | SCH₃ | H | OCH₃ | Cl | CH | |
| L-6 | SCH₃ | H | OCH₃ | Br | CH | |
| L-6 | SCH₃ | H | CH₃ | F | CH | |
| L-6 | SOCH₃ | H | OCH₃ | F | CH | |
| L-6 | SO₂CH₃ | H | OCH₃ | F | CH | |
| L-6 | SO₂CH₃ | H | OCH₃ | Cl | CH | |

TABLE 3e-continued

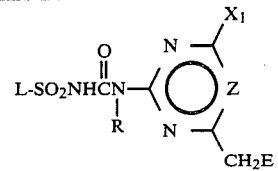

| L | R₅ | R | X₁ | E | Z | m.p. (°C.) |
|---|---|---|---|---|---|---|
| L-6 | SO₂CH₃ | H | OCH₃ | Br | CH | |
| L-6 | SO₂CH₃ | H | OCH₃ | F | N | |
| L-6 | SO₂CH₃ | H | CH₃ | F | CH | |
| L-6 | SO₂CH₃ | H | CH₃ | Cl | CH | |

TABLE 3f

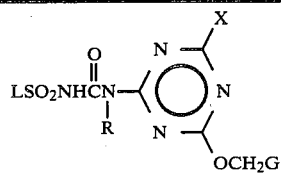

| L | R₅ | R | X | Z | G | m.p. (°C.) |
|---|---|---|---|---|---|---|
| L-4 | CO₂CH₃ | H | OCH₃ | CH | CH(—OCH₂CH₂O—) | |
| L-4 | CH₃ | H | OCH₃ | N | CH(OCH₃)₂ | |
| L-4 | Br | H | OCH₃ | CH | CH(OCH₃)₂ | |
| L-4 | CO₂CH₃ | H | OCH₃ | CH | CH(OCH₃)₂ | |
| L-5 | CO₂CH₃ | H | CH₃ | CH | CH(—OCH₂CH₂O—) | 146–148 |
| L-5 | CO₂CH₃ | H | OCH₃ | CH | C₆H₅ | |
| L-5 | SO₂CH₃ | CH₃ | OCH₃ | CH | CH(OCH₃)₂ | |
| L-5 | CH₃ | H | OCH₃ | N | CH(OCH₃)₂ | |
| L-5 | SO₂N(CH₃)₂ | H | OCH₃ | CH | CH(OCH₃)₂ | |
| L-5 | Cl | H | OCH₃ | CH | CH(—OCH₂CH₂O—) | |
| L-6 | CO₂CH₃ | H | OCH₃ | CH | CH(—OCH₂CH₂O—) | |
| L-6 | CO₂CH₃ | H | OCH₃ | CH | C₆H₅ | |
| L-6 | SCH₃ | H | CH₃ | CH | CH(OCH₃)₂ | |

TABLE 4a

| R₆ | R | X | Y | T | Z | m.p. (°C.) |
|---|---|---|---|---|---|---|
| Cl | H | OCH₃ | H | SPh | CH | |
| NO₂ | H | OCH₃ | H | SPh | CH | |
| CO₂CH₃ | H | OCH₃ | H | SeCH₃ | CH | |
| CO₂CH₃ | H | OCH₃ | H | SePh | CH | |
| CO₂CH₃ | H | OCH₃ | H | SPh | CH | |
| CO₂CH₃ | H | OCH₃ | H | SO₂Ph | CH | |
| CO₂CH₃ | H | OCH₃ | H | OPh | CH | |
| CO₂CH₃ | H | OCH₃ | H | SeCH₃ | N | |
| CO₂CH₃ | H | OCH₃ | H | SePh | N | |
| CO₂CH₃ | H | OCH₃ | H | SPh | N | |
| CO₂CH₂CH₃ | H | OCH₃ | H | SeCH₃ | CH | |
| CO₂CH₂CH₃ | H | OCH₃ | H | SPh | CH | |
| SO₂N(CH₃)₂ | H | OCH₃ | H | SeCH₃ | CH | |
| SO₂N(CH₃)₂ | H | OCH₃ | H | SePh | CH | |
| SO₂N(CH₃)₂ | H | OCH₃ | H | SPh | CH | |
| SO₂N(CH₃)₂ | H | OCH₃ | H | SO₂Ph | CH | |
| SO₂N(CH₃)₂ | H | OCH₃ | H | OPh | CH | |
| SO₂N(CH₃)₂ | H | OCH₃ | H | SPh | N | |
| SO₂CH₂CH₃ | H | OCH₃ | H | SPh | CH | |
| SO₂CH₂CH₃ | H | OCH₃ | H | SPh | N | |
| OCH₃ | H | OCH₃ | H | SeCH₃ | CH | |

TABLE 4a-continued

Structure: phenyl with R6 substituent, CH2-SO2NHC(=O)N(R)- connected to a pyrimidine/triazine ring with X, Z, and CH(Y)T substituents.

| R6 | R | X | Y | T | Z | m.p. (°C.) |
|---|---|---|---|---|---|---|
| OCH3 | H | OCH3 | H | SePh | CH | |
| OCH2CH3 | H | OCH3 | H | SeCH3 | CH | |
| SO2CH3 | H | OCH3 | H | SeCH3 | CH | |
| SO2CH3 | H | OCH3 | H | SePh | CH | |
| SO2CH3 | CH3 | OCH3 | H | SPh | CH | |
| SO2CH3 | CH3 | OCH3 | H | SO2Ph | CH | |
| Cl | CH3 | CH3 | H | SPh | CH | |
| NO2 | H | CH3 | H | SPh | CH | |
| CO2CH3 | H | CH3 | H | SeCH3 | CH | |
| CO2CH3 | H | CH3 | H | SePh | CH | |
| CO2CH3 | H | OCH3 | SPh | SPh | CH | |
| CO2CH3 | H | OCH3 | SeCH3 | SO2Ph | CH | |
| CO2CH3 | H | CH3 | H | OPh | CH | |
| CO2CH3 | H | OCH3 | SeCH3 | SeCH3 | N | |
| CO2CH3 | H | OCH3 | SePh | SePh | N | |
| CO2CH3 | H | CH3 | H | SPh | N | |
| CO2CH2CH3 | H | OCH3 | SeCH3 | SeCH3 | CH | |
| CO2CH2CH3 | H | CH3 | H | SPh | CH | |
| SO2N(CH3)2 | H | CH3 | H | SeCH3 | CH | |
| SO2N(CH3)2 | CH3 | CH3 | H | SePh | CH | |
| SO2N(CH3)2 | CH3 | CH3 | H | SPh | CH | |
| SO2N(CH3)2 | H | OCH3 | SPh | SO2Ph | CH | |
| SO2N(CH3)2 | H | CH3 | H | OPh | CH | |
| SO2N(CH3)2 | H | CH3 | H | SPh | N | |
| SO2CH2CH3 | H | CH3 | H | SPh | CH | |
| SO2CH2CH3 | H | OCH3 | SPh | SPh | N | |
| OCH3 | H | OCH3 | SeCH3 | SeCH3 | CH | |
| CH3 | H | CH3 | H | SePh | CH | |
| CH2CH3 | H | CH3 | H | SeCH3 | CH | |
| SO2CH3 | H | CH3 | H | SeCH3 | CH | |
| SO2CH3 | H | OCH3 | SePh | SePh | CH | |
| SO2CH3 | H | OCH3 | SPh | SPh | CH | |
| SO2CH3 | CH3 | CH3 | H | SO2Ph | CH | |
| CO2CH3 | H | OCH3 | H | OSi(CH3)3 | CH | |
| SO2CH3 | H | CH3 | H | CH2OH | N | |

TABLE 4b

Structure: phenyl with R6, CH2-SO2NHC(=O)N(R)- attached to pyrimidine with X1 and CH=CH2 substituents.

| R6 | R | X1 | m.p. (°C.) |
|---|---|---|---|
| Cl | H | OCH3 | |
| NO2 | H | OCH3 | |
| CO2CH3 | H | CH3 | |
| CO2CH3 | H | OCH3 | |
| CO2CH3 | H | OCH2CH3 | |
| CO2CH2CH3 | H | CH3 | |
| CO2CH2CH3 | H | OCH3 | |
| CO2CH2CH3 | H | OCH2CH3 | |
| SO2N(CH3)2 | H | OCH3 | |
| SO2N(CH3)2 | H | CH3 | |
| OSO2CH3 | H | OCH3 | |
| SO2CH3 | H | OCH3 | |
| SO2CH2CH3 | H | OCH3 | |
| OCH3 | CH3 | OCH3 | |
| OCH2CH3 | CH3 | OCH3 | |

TABLE 4c

Structure: phenyl with R6, CH2-SO2NHC(=O)N(R)- attached to a ring bearing C(OH)(CF3) and C(CF3) groups.

| R6 | R | m.p. (°C.) |
|---|---|---|
| Cl | H | |
| NO2 | H | |
| CO2CH3 | H | |
| CO2CH2CH3 | H | |
| SO2N(CH3)2 | H | |
| OSO2CH3 | H | |
| SO2CH3 | H | |
| SO2CH2CH3 | H | |
| OCH3 | CH3 | |
| OCH2CH3 | CH3 | |

TABLE 4d

Structure: phenyl with R6, CH2-SO2NHC(=O)N(R)- attached to pyrimidine with two CF3 substituents.

| R6 | R | m.p. (°C.) |
|---|---|---|
| Cl | H | |
| NO2 | H | |
| CO2CH3 | H | |
| CO2CH2CH3 | H | |
| SO2N(CH3)2 | H | |
| OSO2CH3 | H | |
| SO2CH3 | H | |
| SO2CH2CH3 | H | |
| OCH3 | H | |
| OCH2CH3 | CH3 | |

TABLE 4e

Structure: phenyl with R6, CH2-SO2NHC(=O)N(R)- attached to pyrimidine with X1, Z, and CH2E substituents.

| R6 | R | X1 | E | Z | m.p. (°C.) |
|---|---|---|---|---|---|
| Cl | H | OCH3 | F | CH | |
| NO2 | H | CH3 | F | CH | |
| NO2 | H | OCH3 | F | CH | |
| NO2 | H | OCH3 | Cl | CH | |
| CO2CH3 | H | OCH3 | F | CH | |
| CO2CH3 | H | CH3 | Cl | CH | |
| CO2CH3 | H | OCH3 | Br | CH | |
| CO2CH3 | H | OCH3 | F | N | |
| CO2CH3 | H | CH3 | F | CH | |
| CO3CH3 | H | OCH2CH3 | F | CH | |
| CO2CH2CH3 | H | OCH3 | F | CH | |
| SO2N(CH3)2 | CH3 | OCH3 | F | CH | |
| SO2N(CH3)2 | CH3 | OCH3 | F | N | |
| SO2N(CH3)2 | CH3 | OCH3 | Cl | CH | |
| SO2N(CH3)2 | CH3 | CH3 | Br | CH | |
| OSO2CH3 | CH3 | OCH3 | F | CH | |
| SO2CH3 | H | OCH3 | F | CH | |
| SO2CH3 | H | CH3 | F | CH | |
| SO2CH2CH3 | H | OCH3 | F | CH | |
| OCH3 | H | OCH3 | F | CH | |
| OCH2CH3 | H | OCH3 | F | CH | |

TABLE 4e-continued

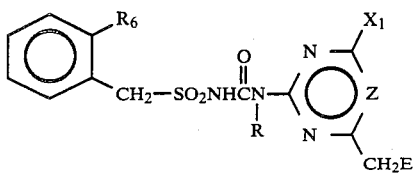

| $R_6$ | R | $X_1$ | E | Z | m.p. (°C.) |
|---|---|---|---|---|---|
| $OCH_2CH_3$ | H | $OCH_3$ | Br | CH | |
| $OCH_2CH_3$ | H | $OCH_3$ | F | N | |

TABLE 4f

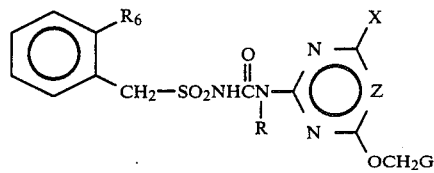

| $R_6$ | R | X | Z | G | m.p. (°C.) |
|---|---|---|---|---|---|
| Cl | H | $OCH_3$ | CH | $CH(-OCH_2CH_2O-)$ | |
| $NO_2$ | H | $OCH_3$ | N | $CH(-OCH_2CH_2O-)$ | |
| $CO_2CH_3$ | H | $OCH_3$ | CH | $CH(-OCH_2CH_2O-)$ | |
| $CO_2CH_3$ | H | $CH_3$ | CH | $CH(OCH_3)_2$ | |
| $SO_2CH_3$ | H | $OCH_3$ | CH | $CH(-OCH_2CH_2O-)$ | |
| $OCH_3$ | H | $OCH_3$ | CH | $C_6H_5$ | |
| $OSO_2CH_3$ | H | $OCH_3$ | CH | $CH(-OCH_2CH_2O-)$ | |

TABLE 5a

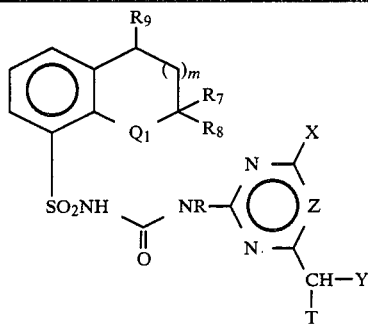

| $R_7$ | $R_8$ | $R_9$ | R | $Q_1$ | X | T | Y | Z | m | m.p. (°C.) |
|---|---|---|---|---|---|---|---|---|---|---|
| $CH_3$ | H | H | H | O | $OCH_3$ | H | $SeCH_3$ | CH | 0 | |
| $CH_3$ | H | H | H | O | $OCH_3$ | H | SePh | CH | 0 | |
| $CH_3$ | H | H | H | O | $OCH_3$ | H | SPh | CH | 0 | |
| $CH_3$ | H | H | H | O | $OCH_3$ | H | $SO_2Ph$ | CH | 0 | |
| $CH_3$ | H | H | H | O | $OCH_3$ | H | SPh | N | 0 | |
| $CH_3$ | H | H | H | O | $OCH_3$ | $SeCH_3$ | $SeCH_3$ | CH | 0 | |
| $CH_3$ | H | H | H | O | $CH_3$ | H | $SeCH_3$ | CH | 0 | |
| $CH_3$ | H | H | H | O | $CH_3$ | H | SePh | CH | 0 | |
| $CH_3$ | $CH_3$ | H | H | O | $CH_3$ | H | SPh | CH | 0 | |
| $CH_3$ | H | H | $CH_3$ | O | $CH_3$ | $SeCH_3$ | $SeCH_3$ | CH | 0 | |
| $CH_3$ | H | H | H | O | $CH_3$ | $SeCH_3$ | SPh | CH | 0 | |
| $CH_3$ | H | H | H | O | $CH_3$ | SPh | SPh | CH | 0 | |
| $CH_3$ | H | H | H | O | $CH_3$ | H | OPh | CH | 0 | |
| $CH_3$ | H | H | H | O | $OCH_3$ | H | OPh | CH | 0 | |
| $CH_2CH_3$ | H | H | H | O | $OCH_3$ | H | $SeCH_3$ | CH | 0 | |
| $CH_2CH_3$ | H | H | H | O | $OCH_3$ | H | SePh | CH | 0 | |
| $CH_2CH_3$ | H | H | H | O | $OCH_3$ | H | SPh | CH | 0 | |
| $CH_2CH_3$ | H | H | H | O | $OCH_3$ | H | $SO_2Ph$ | CH | 0 | |
| $CH_2CH_3$ | H | H | H | O | $OCH_3$ | H | SPh | N | 0 | |
| $CH_2CH_3$ | H | H | H | O | $OCH_3$ | H | $SeCH_3$ | N | 0 | |
| $CH_2CH_3$ | H | H | H | O | $CH_3$ | H | $SeCH_3$ | CH | 0 | |
| $CH_2CH_3$ | H | H | H | O | $CH_3$ | H | SePh | CH | 0 | |
| $CH_2CH_3$ | H | H | H | O | $CH_3$ | H | SPh | CH | 0 | |
| $CH_2CH_3$ | H | H | H | O | $OCH_3$ | $SeCH_3$ | $SeCH_3$ | CH | 0 | |
| $CH_2CH_3$ | H | H | H | O | $OCH_3$ | SPh | SPh | CH | 0 | |
| $CH_3$ | H | $CH_3$ | H | O | $OCH_3$ | H | SePh | CH | 0 | |
| $CH_3$ | H | $CH_3$ | H | O | $OCH_3$ | H | SPh | CH | 0 | |
| $CH_3$ | H | H | H | O | $OCH_3$ | H | $SeCH_3$ | CH | 1 | |
| $CH_3$ | H | H | H | O | $OCH_3$ | H | SePh | CH | 1 | |
| $CH_3$ | H | H | H | O | $OCH_3$ | H | SPh | CH | 1 | |
| $CH_3$ | H | H | H | O | $OCH_3$ | H | $SO_2Ph$ | CH | 1 | |
| $CH_3$ | H | H | H | O | $OCH_3$ | H | SPh | N | 1 | |
| $CH_3$ | H | H | H | O | $OCH_3$ | $SeCH_3$ | $SeCH_3$ | CH | 1 | |
| $CH_3$ | H | H | H | O | $CH_3$ | H | $SeCH_3$ | CH | 1 | |
| $CH_3$ | H | H | H | O | $CH_3$ | H | SePh | CH | 1 | |
| $CH_3$ | $CH_3$ | H | H | O | $CH_3$ | H | SPh | CH | 1 | |
| $CH_3$ | H | H | $CH_3$ | O | $CH_3$ | $SeCH_3$ | $SeCH_3$ | CH | 1 | |
| $CH_3$ | H | H | H | O | $CH_3$ | $SeCH_3$ | SPh | CH | 1 | |
| $CH_3$ | H | H | H | O | $CH_3$ | SPh | SPh | CH | 1 | |
| $CH_3$ | H | H | H | O | $CH_3$ | H | OPh | CH | 1 | |
| $CH_3$ | H | H | H | O | $OCH_3$ | H | OPh | CH | 1 | |

TABLE 5a-continued

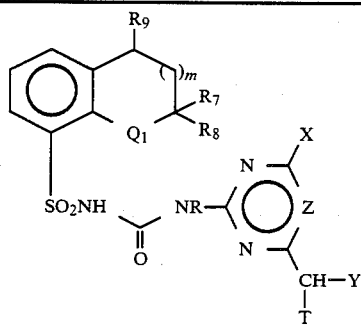

| R7 | R8 | R9 | R | Q1 | X | T | Y | Z | m | m.p. (°C.) |
|---|---|---|---|---|---|---|---|---|---|---|
| CH2CH3 | H | H | H | O | OCH3 | H | SeCH3 | CH | 1 | |
| CH2CH3 | H | H | H | O | OCH3 | H | SePh | CH | 1 | |
| CH2CH3 | H | H | H | O | OCH3 | H | SPh | CH | 1 | |
| CH2CH3 | H | H | H | O | OCH3 | H | SO2Ph | CH | 1 | |
| CH2CH3 | H | H | H | O | OCH3 | H | SPh | N | 1 | |
| CH2CH3 | H | H | H | O | OCH3 | H | SeCH3 | N | 1 | |
| CH2CH3 | H | H | H | O | CH3 | H | SeCH3 | CH | 1 | |
| CH2CH3 | H | H | H | O | CH3 | H | SePh | CH | 1 | |
| CH2CH3 | H | H | H | O | CH3 | H | SPh | CH | 1 | |
| CH2CH3 | H | H | H | O | OCH3 | SeCH3 | SeCH3 | CH | 1 | |
| CH2CH3 | H | H | H | O | OCH3 | SPh | SPh | CH | 1 | |
| CH3 | H | H | H | S | OCH3 | H | SeCH3 | CH | 0 | |
| CH3 | H | H | H | S | OCH3 | H | SePh | CH | 0 | |
| CH3 | H | H | H | S | OCH3 | H | SPh | CH | 0 | |
| CH3 | H | H | H | S | OCH3 | H | SO2Ph | CH | 0 | |
| CH3 | H | H | H | S | OCH3 | H | SPh | N | 0 | |
| CH3 | H | H | H | S | OCH3 | SeCH3 | SeCH3 | CH | 0 | |
| CH3 | H | H | H | S | CH3 | H | SeCH3 | CH | 0 | |
| CH3 | H | H | H | S | CH3 | H | SePh | CH | 0 | |
| CH3 | CH3 | H | H | S | CH3 | H | SPh | CH | 0 | |
| CH3 | H | H | CH3 | S | CH3 | SeCH3 | SeCH3 | CH | 0 | |
| CH3 | H | H | H | S | CH3 | SeCH3 | SPh | CH | 0 | |
| CH3 | H | H | H | S | CH3 | SPh | SPh | CH | 0 | |
| CH3 | H | H | H | S | CH3 | H | OPh | CH | 0 | |
| CH3 | H | H | H | S | OCH3 | H | OPh | CH | 0 | |
| CH2CH3 | H | H | H | S | OCH3 | H | SeCH3 | CH | 0 | |
| CH2CH3 | H | H | H | S | OCH3 | H | SePh | CH | 0 | |
| CH2CH3 | H | H | H | S | OCH3 | H | SPh | CH | 0 | |
| CH2CH3 | H | H | H | S | OCH3 | H | SO2Ph | CH | 0 | |
| CH2CH3 | H | H | H | S | OCH3 | H | SPh | N | 0 | |
| CH2CH3 | H | H | H | S | OCH3 | H | SeCH3 | N | 0 | |
| CH2CH3 | H | H | H | S | CH3 | H | SeCH3 | CH | 0 | |
| CH2CH3 | H | H | H | S | CH3 | H | SePh | CH | 0 | |
| CH2CH3 | H | H | H | S | CH3 | H | SPh | CH | 0 | |
| CH2CH3 | H | H | H | S | OCH3 | SeCH3 | SeCH3 | CH | 0 | |
| CH2CH3 | H | H | H | S | OCH3 | SPh | SPh | CH | 0 | |
| CH3 | H | H | H | S | OCH3 | H | SeCH3 | CH | 1 | |
| CH3 | H | H | H | S | OCH3 | H | SePh | CH | 1 | |
| CH3 | H | H | H | S | OCH3 | H | SPh | CH | 1 | |
| CH3 | H | H | H | S | OCH3 | H | SO2Ph | CH | 1 | |
| CH3 | H | H | H | S | OCH3 | H | SPh | N | 1 | |
| CH3 | H | H | H | S | OCH3 | SeCH3 | SeCH3 | CH | 1 | |
| CH3 | H | H | H | S | CH3 | H | SeCH3 | CH | 1 | |
| CH3 | H | H | H | S | CH3 | H | SePh | CH | 1 | |
| CH3 | CH3 | H | H | S | CH3 | H | SPh | CH | 1 | |
| CH3 | H | H | CH3 | S | CH3 | SeCH3 | SeCH3 | CH | 1 | |
| CH3 | H | H | H | S | CH3 | SeCH3 | SPh | CH | 1 | |
| CH3 | H | H | H | S | CH3 | SPh | SPh | CH | 1 | |
| CH3 | H | H | H | S | CH3 | H | OPh | CH | 1 | |
| CH3 | H | H | H | S | OCH3 | H | OPh | CH | 1 | |
| CH2CH3 | H | H | H | S | OCH3 | H | SeCH3 | CH | 1 | |
| CH2CH3 | H | H | H | S | OCH3 | H | SePh | CH | 1 | |
| CH2CH3 | H | H | H | S | OCH3 | H | SPh | CH | 1 | |
| CH2CH3 | H | H | H | S | OCH3 | H | SO2Ph | CH | 1 | |
| CH2CH3 | H | H | H | S | OCH3 | H | SPh | N | 1 | |
| CH2CH3 | H | H | H | S | OCH3 | H | SeCH3 | N | 1 | |
| CH2CH3 | H | H | H | S | CH3 | H | SeCH3 | CH | 1 | |
| CH2CH3 | H | H | H | S | CH3 | H | SePh | CH | 1 | |
| CH2CH3 | H | H | H | S | CH3 | H | SPh | CH | 1 | |
| CH2CH3 | H | H | H | S | OCH3 | SeCH3 | SeCH3 | CH | 1 | |
| CH2CH3 | H | H | H | S | OCH3 | SPh | SPh | CH | 1 | |
| CH3 | H | H | H | SO2 | OCH3 | H | SeCH3 | CH | 0 | |
| CH3 | H | H | H | SO2 | OCH3 | H | SePh | CH | 0 | |
| CH3 | H | H | H | SO2 | OCH3 | H | SPh | CH | 0 | |
| CH3 | H | H | H | SO2 | OCH3 | H | SO2Ph | CH | 0 | |

TABLE 5a-continued

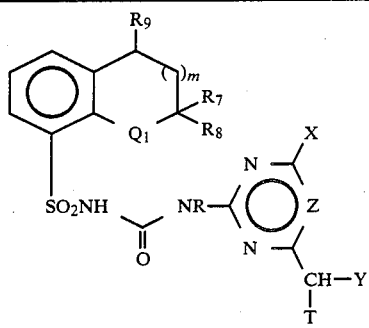

| R₇ | R₈ | R₉ | R | Q₁ | X | T | Y | Z | m | m.p. (°C.) |
|---|---|---|---|---|---|---|---|---|---|---|
| CH₃ | H | H | H | SO₂ | OCH₃ | H | SPh | N | 0 | |
| CH₃ | H | H | H | SO₂ | OCH₃ | SeCH₃ | SeCH₃ | CH | 0 | |
| CH₃ | H | H | H | SO₂ | CH₃ | H | SeCH₃ | CH | 0 | |
| CH₃ | H | H | H | SO₂ | CH₃ | H | SePh | CH | 0 | |
| CH₃ | CH₃ | H | H | SO₂ | CH₃ | H | SPh | CH | 0 | |
| CH₃ | H | H | CH₃ | SO₂ | CH₃ | SeCH₃ | SeCH₃ | CH | 0 | |
| CH₃ | H | H | H | SO₂ | CH₃ | SeCH₃ | SPh | CH | 0 | |
| CH₃ | H | H | H | SO₂ | CH₃ | SPh | SPh | CH | 0 | |
| CH₃ | H | H | H | SO₂ | CH₃ | H | OPh | CH | 0 | |
| CH₃ | H | H | H | SO₂ | OCH₃ | H | OPh | CH | 0 | |
| CH₂CH₃ | H | H | H | SO₂ | OCH₃ | H | SeCH₃ | CH | 0 | |
| CH₂CH₃ | H | H | H | SO₂ | OCH₃ | H | SePh | CH | 0 | |
| CH₂CH₃ | H | H | H | SO₂ | OCH₃ | H | SPh | CH | 0 | |
| CH₂CH₃ | H | H | H | SO₂ | OCH₃ | H | SO₂Ph | CH | 0 | |
| CH₂CH₃ | H | H | H | SO₂ | OCH₃ | H | SPh | N | 0 | |
| CH₂CH₃ | H | H | H | SO₂ | OCH₃ | H | SeCH₃ | N | 0 | |
| CH₂CH₃ | H | H | H | SO₂ | CH₃ | H | SeCH₃ | CH | 0 | |
| CH₂CH₃ | H | H | H | SO₂ | CH₃ | H | SePh | CH | 0 | |
| CH₂CH₃ | H | H | H | SO₂ | CH₃ | H | SPh | CH | 0 | |
| CH₂CH₃ | H | H | H | SO₂ | OCH₃ | SeCH₃ | SeCH₃ | CH | 0 | |
| CH₂CH₃ | H | H | H | SO₂ | OCH₃ | SPh | SPh | CH | 0 | |
| CH₃ | H | H | H | SO₂ | OCH₃ | H | SeCH₃ | CH | 1 | |
| CH₃ | H | H | H | SO₂ | OCH₃ | H | SePh | CH | 1 | |
| CH₃ | H | H | H | SO₂ | OCH₃ | H | SPh | CH | 1 | |
| CH₃ | H | H | H | SO₂ | OCH₃ | H | SO₂Ph | CH | 1 | |
| CH₃ | H | H | H | SO₂ | OCH₃ | H | SPh | N | 1 | |
| CH₃ | H | H | H | SO₂ | OCH₃ | SeCH₃ | SeCH₃ | CH | 1 | |
| CH₃ | H | H | H | SO₂ | CH₃ | H | SeCH₃ | CH | 1 | |
| CH₃ | H | H | H | SO₂ | CH₃ | H | SePh | CH | 1 | |
| CH₃ | CH₃ | H | H | SO₂ | CH₃ | H | SPh | CH | 1 | |
| CH₃ | H | H | CH₃ | SO₃ | CH₃ | SeCH₃ | SeCH₃ | CH | 1 | |
| CH₃ | H | H | H | SO₂ | CH₃ | SeCH₃ | SPh | CH | 1 | |
| CH₃ | H | H | H | SO₂ | CH₃ | SPh | SPh | CH | 1 | |
| CH₃ | H | H | H | SO₂ | CH₃ | H | OPh | CH | 1 | |
| CH₃ | H | H | H | SO₂ | OCH₃ | H | OPh | CH | 1 | |
| CH₂CH₃ | H | H | H | SO₂ | OCH₃ | H | SeCH₃ | CH | 1 | |
| CH₂CH₃ | H | H | H | SO₂ | OCH₃ | H | SePh | CH | 1 | |
| CH₂CH₃ | H | H | H | SO₂ | OCH₃ | H | SPh | CH | 1 | |
| CH₂CH₃ | H | H | H | SO₂ | OCH₃ | H | SO₂Ph | CH | 1 | |
| CH₂CH₃ | H | H | H | SO₂ | OCH₃ | H | SPh | N | 1 | |
| CH₂CH₃ | H | H | H | SO₂ | OCH₃ | H | SeCH₃ | N | 1 | |
| CH₂CH₃ | H | H | H | SO₂ | CH₃ | H | SeCH₃ | CH | 1 | |
| CH₂CH₃ | H | H | H | SO₂ | CH₃ | H | SePh | CH | 1 | |
| CH₂CH₃ | H | H | H | SO₂ | CH₃ | H | SPh | CH | 1 | |
| CH₂CH₃ | H | H | H | SO₂ | OCH₃ | H | OSi(CH₃)₃ | CH | 0 | |

TABLE 5b

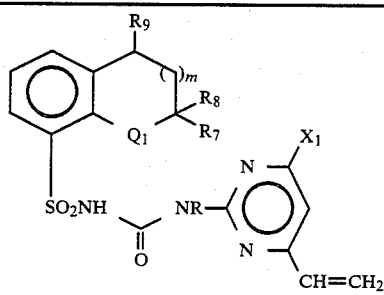

| R7 | R8 | R9 | m | Q1 | R | X1 | m.p. (°C.) |
|---|---|---|---|---|---|---|---|
| CH3 | H | H | 0 | S | H | OCH3 | |
| CH3 | H | H | 0 | S | H | CH3 | |
| CH3 | H | H | 0 | S | H | OCH2CH3 | |
| CH2CH3 | H | H | 0 | S | H | OCH3 | |
| CH2CH3 | H | H | 0 | S | H | CH3 | |
| CH2CH3 | H | H | 0 | S | H | OCH2CH3 | |
| CH3 | CH3 | H | 0 | S | H | OCH3 | |
| CH3 | CH3 | H | 0 | S | H | OCH2CH3 | |
| CH3 | CH3 | H | 0 | S | H | CH3 | |
| CH3 | H | CH3 | 0 | S | H | CH3 | |
| CH3 | H | CH3 | 0 | S | H | OCH3 | |
| CH3 | H | CH3 | 0 | S | H | OCH2CH3 | |
| CH2CH3 | H | CH3 | 0 | S | H | OCH3 | |
| CH3 | H | H | 1 | S | H | OCH3 | |
| CH3 | H | H | 1 | S | H | CH3 | |
| CH3 | H | H | 1 | S | H | OCH2CH3 | |
| CH2CH3 | H | H | 1 | S | H | OCH3 | |
| CH2CH3 | H | H | 1 | S | H | CH3 | |
| CH2CH3 | H | H | 1 | S | H | OCH2CH3 | |
| CH3 | CH3 | H | 1 | S | H | OCH3 | |
| CH3 | CH3 | H | 1 | S | H | OCH2CH3 | |
| CH3 | H | H | 1 | S | CH3 | OCH3 | |
| CH3 | H | H | 0 | O | H | OCH3 | |
| CH3 | H | H | 0 | O | H | CH3 | |
| CH3 | H | H | 0 | O | H | OCH2CH3 | |
| CH2CH3 | H | H | 0 | O | H | OCH3 | |
| CH2CH3 | H | H | 0 | O | H | CH3 | |
| CH2CH3 | H | H | 0 | O | H | OCH2CH3 | |
| CH3 | CH3 | H | 0 | O | H | OCH3 | |
| CH3 | CH3 | H | 0 | O | H | OCH2CH3 | |
| CH3 | CH3 | H | 0 | O | H | CH3 | |
| CH3 | H | CH3 | 0 | O | H | CH3 | |
| CH3 | H | CH3 | 0 | O | H | OCH3 | |
| CH3 | H | CH3 | 0 | O | H | OCH2CH3 | |
| CH2CH3 | H | CH3 | 0 | O | H | OCH3 | |
| CH3 | H | H | 1 | O | H | OCH3 | |
| CH3 | H | H | 1 | O | H | CH3 | |
| CH3 | H | H | 1 | O | H | OCH2CH3 | |
| CH2CH3 | H | H | 1 | O | H | OCH3 | |
| CH2CH3 | H | H | 1 | O | H | CH3 | |
| CH2CH3 | H | H | 1 | O | H | OCH2CH3 | |
| CH3 | CH3 | H | 1 | O | H | OCH3 | |
| CH3 | CH3 | H | 1 | O | H | OCH2CH3 | |
| CH3 | H | H | 1 | O | CH3 | OCH3 | |
| CH3 | H | H | 0 | SO2 | H | OCH3 | |
| CH3 | H | H | 0 | SO2 | H | CH3 | |
| CH3 | H | H | 0 | SO2 | H | OCH2CH3 | |
| CH2CH3 | H | H | 0 | SO2 | H | OCH3 | |
| CH2CH3 | H | H | 0 | SO2 | H | CH3 | |
| CH2CH3 | H | H | 0 | SO2 | H | OCH2CH3 | |
| CH3 | CH3 | H | 0 | SO2 | H | OCH3 | |
| CH3 | CH3 | H | 0 | SO2 | H | OCH2CH3 | |
| CH3 | CH3 | H | 0 | SO2 | H | CH3 | |
| CH3 | H | CH3 | 0 | SO2 | H | CH3 | |
| CH3 | H | CH3 | 0 | SO2 | H | OCH3 | |
| CH3 | H | CH3 | 0 | SO2 | H | OCH2CH3 | |
| CH2CH3 | H | CH3 | 0 | SO2 | H | OCH3 | |
| CH3 | H | H | 1 | SO2 | H | OCH3 | |
| CH3 | H | H | 1 | SO2 | H | CH3 | |
| CH3 | H | H | 1 | SO2 | H | OCH2CH3 | |
| CH2CH3 | H | H | 1 | SO2 | H | OCH3 | |
| CH2CH3 | H | H | 1 | SO2 | H | CH3 | |
| CH2CH3 | H | H | 1 | SO2 | H | OCH2CH3 | |
| CH3 | CH3 | H | 1 | SO2 | H | OCH3 | |
| CH3 | CH3 | H | 1 | SO2 | H | OCH2CH3 | |

TABLE 5b-continued

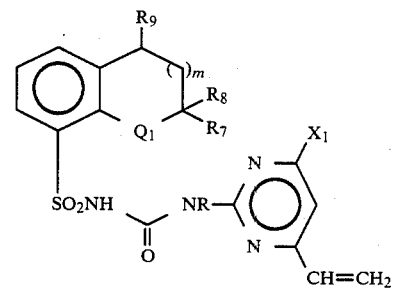

| R7 | R8 | R9 | m | Q1 | R | X1 | m.p. (°C.) |
|---|---|---|---|---|---|---|---|
| CH3 | H | H | 1 | SO2 | CH3 | OCH3 | |

TABLE 5c

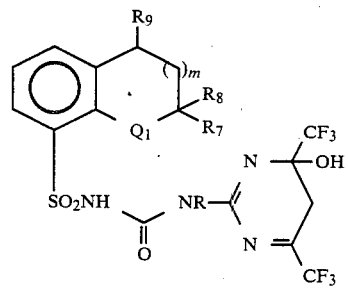

| R7 | R8 | R9 | Q1 | R | m | m.p. (°C.) |
|---|---|---|---|---|---|---|
| CH3 | H | H | O | H | 0 | |
| CH3 | CH3 | H | O | H | 0 | |
| CH3 | H | CH3 | O | H | 0 | |
| CH2CH3 | H | H | O | H | 0 | |
| CH2CH3 | H | CH3 | O | H | 0 | |
| CH3 | CH3 | CH3 | O | H | 0 | |
| CH3 | H | H | O | CH3 | 0 | |
| CH3 | H | H | O | H | 1 | |
| CH3 | CH3 | H | O | H | 1 | |
| CH2CH3 | H | H | O | H | 1 | |
| CH3 | H | H | S | H | 0 | |
| CH3 | CH3 | H | S | H | 0 | |
| CH3 | H | CH3 | S | H | 0 | |
| CH2CH3 | H | H | S | H | 0 | |
| CH2CH3 | H | CH3 | S | H | 0 | |
| CH3 | CH3 | CH3 | S | H | 0 | |
| CH3 | H | H | S | CH3 | 0 | |
| CH3 | H | H | S | H | 1 | |
| CH3 | CH3 | H | S | H | 1 | |
| CH2CH3 | H | H | S | H | 1 | |
| CH3 | H | H | SO2 | H | 0 | |
| CH3 | CH3 | H | SO2 | H | 0 | |
| CH3 | H | CH3 | SO2 | H | 0 | |
| CH2CH3 | H | H | SO2 | H | 0 | |
| CH2CH3 | H | CH3 | SO2 | H | 0 | |
| CH3 | CH3 | CH3 | SO2 | H | 0 | |
| CH3 | H | H | SO2 | CH3 | 0 | |
| CH3 | H | H | SO2 | H | 1 | |
| CH3 | CH3 | H | SO2 | H | 1 | |
| CH2CH3 | H | H | SO2 | H | 1 | |

TABLE 5d

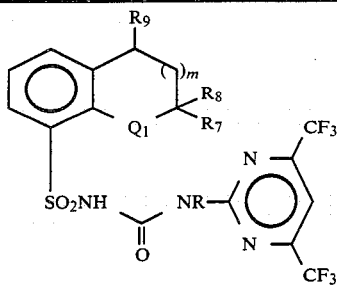

| R7 | R8 | R9 | Q1 | R | m | m.p. (°C.) |
|---|---|---|---|---|---|---|
| CH3 | H | H | O | H | 0 | |
| CH3 | CH3 | H | O | H | 0 | |
| CH3 | H | CH3 | O | H | 0 | |
| CH2CH3 | H | H | O | H | 0 | |
| CH2CH3 | H | CH3 | O | H | 0 | |
| CH3 | CH3 | CH3 | O | H | 0 | |
| CH3 | H | H | O | CH3 | 0 | |
| CH3 | H | H | O | H | 1 | |
| CH3 | CH3 | H | O | H | 1 | |
| CH2CH3 | H | H | O | H | 1 | |
| CH3 | H | H | S | H | 0 | |
| CH3 | CH3 | H | S | H | 0 | |
| CH3 | H | CH3 | S | H | 0 | |
| CH2CH3 | H | H | S | H | 0 | |
| CH2CH3 | H | CH3 | S | H | 0 | |
| CH3 | CH3 | CH3 | S | H | 0 | |
| CH3 | H | H | S | CH3 | 0 | |
| CH3 | H | H | S | H | 1 | |
| CH3 | CH3 | H | S | H | 1 | |
| CH2CH3 | H | H | S | H | 1 | |
| CH3 | H | H | SO2 | H | 0 | |
| CH3 | CH3 | H | SO2 | H | 0 | |
| CH3 | H | CH3 | SO2 | H | 0 | |
| CH2CH3 | H | H | SO2 | H | 0 | |
| CH2CH3 | H | CH3 | SO2 | H | 0 | |
| CH3 | CH3 | CH3 | SO2 | H | 0 | |
| CH3 | H | H | SO2 | CH3 | 0 | |
| CH3 | H | H | SO2 | H | 1 | |
| CH3 | CH3 | H | SO2 | H | 1 | |
| CH2CH3 | H | H | SO2 | H | 1 | |

TABLE 6a

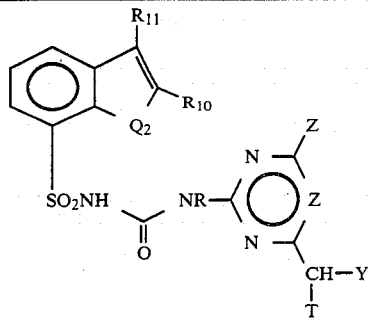

| R10 | R11 | Q2 | R | X | T | Y | Z | m.p. (°C.) |
|---|---|---|---|---|---|---|---|---|
| H | H | O | H | OCH3 | H | SeCH3 | CH | |
| H | H | O | H | OCH3 | H | SePh | CH | |
| H | H | O | H | OCH3 | H | SPh | CH | |
| CH3 | H | O | H | OCH3 | H | SeCH3 | CH | |
| CH3 | H | O | H | OCH3 | H | SePh | CH | |
| CH3 | H | O | H | OCH3 | H | SPh | CH | |
| CH3 | H | O | H | OCH3 | H | SO2Ph | CH | |
| CH3 | H | O | H | CH3 | H | SPh | CH | |
| CH3 | H | O | H | CH3 | H | SPh | N | |
| CH3 | H | O | H | CH3 | SeCH3 | SeCH3 | CH | |
| CH3 | H | O | H | OCH3 | SPh | SPh | CH | |
| H | CH3 | O | H | OCH3 | H | SeCH3 | CH | |
| H | CH3 | O | H | OCH3 | H | SePh | CH | |
| H | CH3 | O | H | OCH3 | H | SPh | CH | |
| H | CH3 | O | H | OCH3 | SeCH3 | SeCH3 | CH | |
| CH3 | CH3 | O | H | OCH3 | H | SeCH3 | CH | |
| CH3 | CH3 | O | H | OCH3 | H | SPh | CH | |
| CH3 | H | O | CH3 | OCH3 | H | SeCH3 | CH | |
| H | H | S | H | OCH3 | H | SeCH3 | CH | |
| H | H | S | H | OCH3 | H | SePh | CH | |
| H | H | S | H | OCH3 | H | SPh | CH | |
| CH3 | H | S | H | OCH3 | H | SeCH3 | CH | |
| CH3 | H | S | H | OCH3 | H | SePh | CH | |
| CH3 | H | S | H | OCH3 | H | SPh | CH | |
| CH3 | H | S | H | OCH3 | H | SO2Ph | CH | |
| CH3 | H | S | H | CH3 | H | SPh | CH | |
| CH3 | H | S | H | CH3 | H | SPh | N | |
| CH3 | H | S | H | CH3 | SeCH3 | SeCH3 | CH | |
| CH3 | H | S | H | OCH3 | SPh | SPh | CH | |
| H | CH3 | S | H | OCH3 | H | SeCH3 | CH | |
| H | CH3 | S | H | OCH3 | H | SePh | CH | |
| H | CH3 | S | H | OCH3 | H | SPh | CH | |

TABLE 5e

| Q1 | m | R7 | R8 | R9 | R | X | Z | G | m.p. (°C.) |
|---|---|---|---|---|---|---|---|---|---|
| O | 0 | H | H | H | H | OCH3 | CH | CH(—OCH2CH2O—) | |
| O | 0 | CH3 | H | H | H | OCH3 | N | CH(OCH3)2 | |
| S | 1 | H | H | H | H | OCH3 | CH | CH(OCH3)2 | |
| S | 0 | CH3 | H | H | H | OCH3 | CH | C6H5 | |
| SO2 | 0 | H | H | H | H | OCH3 | CH | CH(—OCH2CH2O—) | |
| SO2 | 0 | CH3 | CH3 | CH3 | H | OCH3 | CH | CH(—OCH2CH2O—) | |
| SO2 | 1 | H | H | H | H | CH3 | CH | CH(—OCH2CH2O—) | |
| S | 0 | H | H | H | H | OCH3 | CH | CH(—OCH2CH2O—) | |
| O | 0 | H | H | H | H | OCH3 | CH | CH(OCH3)2 | |
| S | 0 | H | H | H | H | OCH3 | CH | C6H5 | |
| SO2 | 1 | H | H | H | H | OCH3 | CH | CH(OCH3)2 | |

TABLE 6a-continued

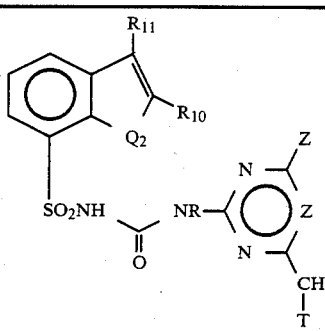

| R10 | R11 | Q2 | R | X | T | Y | Z | m.p. (°C.) |
|---|---|---|---|---|---|---|---|---|
| H | CH3 | S | H | OCH3 | SeCH3 | SeCH3 | CH | |
| CH3 | CH3 | S | H | OCH3 | H | SeCH3 | CH | |
| CH3 | CH3 | S | H | OCH3 | H | SPh | CH | |
| CH3 | H | S | CH3 | OCH3 | H | SeCH3 | CH | |
| CH3 | H | O | CH3 | OCH3 | H | OSi(CH3)3 | CH | |
| CH3 | H | S | CH3 | OCH3 | H | OSi(CH3)3 | N | |
| H | H | S | CH3 | OCH3 | H | CH2OSi(CH3)3 | N | |

TABLE 6b

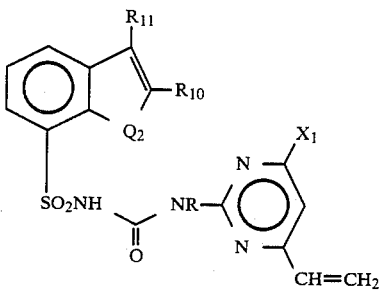

| R10 | R11 | Q2 | R | X1 | m.p. (°C.) |
|---|---|---|---|---|---|
| H | H | O | H | OCH3 | |
| CH3 | H | O | H | OCH3 | |
| CH3 | H | O | H | CH3 | |
| CH3 | H | O | H | OCH2CH3 | |
| H | CH3 | O | H | OCH3 | |
| CH3 | CH3 | O | H | OCH3 | |
| CH3 | H | O | CH3 | OCH3 | |
| H | H | S | H | OCH3 | |
| CH3 | H | S | H | OCH3 | |
| CH3 | H | S | H | CH3 | |
| CH3 | H | S | H | OCH2CH3 | |
| H | CH3 | S | H | OCH3 | |
| CH3 | CH3 | S | H | OCH3 | |
| CH3 | H | S | CH3 | OCH3 | |

TABLE 6c

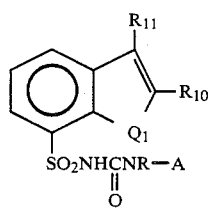

| R10 | R11 | Q1 | R | A | m.p. (°C.) |
|---|---|---|---|---|---|
| CH3 | H | O | H | A-3 | |
| H | H | O | H | A-3 | |
| CH3 | CH3 | O | H | A-3 | |
| CH3 | H | O | CH3 | A-3 | |
| CH3 | H | S | H | A-3 | |
| H | H | S | H | A-3 | |

TABLE 6c-continued

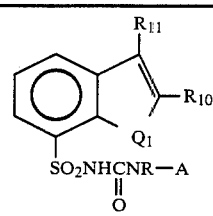

| R10 | R11 | Q1 | R | A | m.p. (°C.) |
|---|---|---|---|---|---|
| CH3 | CH3 | S | H | A-3 | |
| H | CH3 | S | H | A-3 | |
| H | H | O | H | A-4 | |
| CH3 | H | O | H | A-4 | |
| CH3 | CH3 | O | H | A-4 | |
| CH3 | H | O | CH3 | A-4 | |
| H | CH3 | O | H | A-4 | |
| H | H | S | H | A-4 | |
| CH3 | H | S | H | A-4 | |
| CH3 | CH3 | S | H | A-4 | |
| H | CH3 | S | H | A-4 | |

TABLE 6d

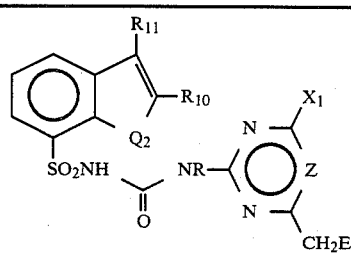

| R10 | R11 | Q1 | R | X1 | E | Z | m.p. (°C.) |
|---|---|---|---|---|---|---|---|
| H | H | O | H | OCH3 | F | CH | |
| H | H | O | H | OCH3 | Cl | CH | |
| CH3 | H | O | H | OCH3 | F | CH | |
| CH3 | H | O | H | CH3 | F | CH | |
| CH3 | H | O | H | CH3 | F | N | |
| H | CH3 | O | H | OCH3 | F | CH | |
| H | CH3 | O | H | OCH3 | Br | CH | |
| H | H | S | H | OCH3 | F | CH | |
| CH3 | H | S | H | OCH3 | F | CH | |
| CH3 | H | S | H | OCH3 | Cl | CH | |
| CH3 | H | S | H | CH3 | Br | CH | |
| CH3 | CH3 | S | H | OCH3 | F | CH | |
| CH3 | H | S | H | OCH3 | F | N | |

TABLE 6e

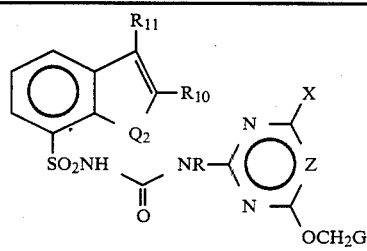

| Q2 | R10 | R11 | R | X | Z | G | m.p. (°C.) |
|---|---|---|---|---|---|---|---|
| O | H | H | H | OCH3 | CH | CH(—OCH2CH2O—) | |
| O | H | H | H | CH3 | CH | CH(—OCH2CH2O—) | |
| O | CH3 | CH3 | H | OCH3 | N | CH(—OCH2CH2O—) | |
| O | CH3 | H | H | OCH3 | CH | CH(OCH3)2 | |
| S | H | H | H | OCH3 | CH | CH(—OCH2CH2O—) | |
| S | CH3 | H | H | OCH3 | CH | C6H5 | |
| S | H | H | H | CH3 | CH | CH(—OCH2CH2O—) | |
| S | H | H | H | OCH3 | CH | CH(OCH3)2 | |

TABLE 7a

| R9 | R12 | R | m | X | T | Y | Z | m.p. (°C.) |
|---|---|---|---|---|---|---|---|---|
| H | CH3 | H | 0 | OCH3 | H | SeCH3 | CH | |
| H | CH3 | H | 0 | OCH3 | H | SePh | CH | |
| H | CH3 | H | 0 | OCH3 | H | SPh | CH | |
| H | CH3 | H | 0 | OCH3 | H | SO2Ph | CH | |
| H | CH3 | H | 0 | OCH3 | H | OPh | CH | |
| H | CH3 | H | 0 | CH3 | H | SeCH3 | CH | |
| H | CH3 | H | 0 | CH3 | H | SePh | CH | |
| H | CH3 | H | 0 | CH3 | H | SPh | CH | |
| H | CH3 | H | 0 | OCH3 | H | SeCH3 | N | |
| H | CH3 | H | 0 | OCH3 | H | SPh | N | |
| H | CH3 | H | 0 | OCH3 | SeCH3 | SeCH3 | CH | |
| H | CH3 | H | 0 | OCH3 | SPh | SPh | CH | |
| CH3 | CH3 | H | 0 | OCH3 | H | SPh | CH | |
| H | CH2CH3 | H | 0 | OCH3 | H | SeCH3 | CH | |
| H | CH2CH3 | H | 0 | OCH3 | H | SePh | CH | |
| H | CH2CH3 | H | 0 | OCH3 | H | SPh | CH | |
| H | CH2CH3 | H | 0 | OCH3 | H | SO2Ph | CH | |
| H | CH2CH3 | H | 0 | OCH3 | H | SPh | N | |
| H | CH2CH3 | H | 0 | OCH3 | H | OPh | CH | |
| H | CH2CH3 | H | 0 | CH3 | H | SeCH3 | CH | |
| H | CH2CH3 | H | 0 | CH3 | H | SePh | CH | |
| H | CH2CH3 | H | 0 | CH3 | H | SPh | CH | |
| H | CH2CH3 | H | 0 | CH3 | H | SPh | N | |
| H | CH3 | H | 0 | OCH2CH3 | H | SePh | CH | |
| H | CH3 | H | 0 | Cl | H | SPh | CH | |
| H | CH3 | H | 0 | F | H | SPh | CH | |
| H | CH3 | H | 0 | Br | H | SePh | CH | |
| H | CH3 | H | 0 | CF3 | H | SePh | CH | |
| H | CH3 | H | 0 | OCHF2 | H | SPh | CH | |
| CH3 | CH2CH3 | H | 0 | OCH3 | H | SPh | CH | |
| H | CH2CH2CH3 | H | 0 | OCH3 | H | SeCH3 | CH | |
| H | CH2CH2CH3 | H | 0 | OCH3 | H | SePh | CH | |
| H | CH2CH2CH3 | H | 0 | OCH3 | H | SPh | CH | |
| H | CH2CH2CH3 | H | 0 | OCH3 | H | SO2Ph | CH | |
| H | CH2CH2CH3 | H | 0 | OCH3 | H | OPh | CH | |
| H | CH3 | CH3 | 0 | OCH3 | H | SPh | CH | |
| H | CH3 | H | 1 | OCH3 | H | SeCH3 | CH | |
| H | CH3 | H | 1 | OCH3 | H | SePh | CH | |
| H | CH3 | H | 1 | OCH3 | H | SPh | CH | |
| H | CH3 | H | 1 | OCH3 | H | SO2Ph | CH | |
| H | CH3 | H | 1 | OCH3 | H | OPh | CH | |
| H | CH3 | H | 1 | CH3 | H | SeCH3 | CH | |
| H | CH3 | H | 1 | CH3 | H | SePh | CH | |
| H | CH3 | H | 1 | CH3 | H | SPh | CH | |
| H | CH3 | H | 1 | OCH3 | H | SeCH3 | N | |
| H | CH3 | H | 1 | OCH3 | H | SPh | N | |
| H | CH3 | H | 1 | OCH3 | SeCH3 | SeCH3 | CH | |
| H | CH3 | H | 1 | OCH3 | SPh | SPh | CH | |
| H | CH2CH3 | H | 1 | OCH3 | H | SeCH3 | CH | |
| H | CH2CH3 | H | 1 | OCH3 | H | SePh | CH | |
| H | CH2CH3 | H | 1 | OCH3 | H | SPh | CH | |
| H | CH2CH3 | H | 1 | OCH3 | H | SO2Ph | CH | |
| H | CH2CH3 | H | 1 | OCH3 | H | SPh | N | |
| H | CH2CH3 | H | 1 | OCH3 | H | OPh | CH | |
| H | CH2CH3 | H | 1 | CH3 | H | SeCH3 | CH | |

TABLE 7a-continued

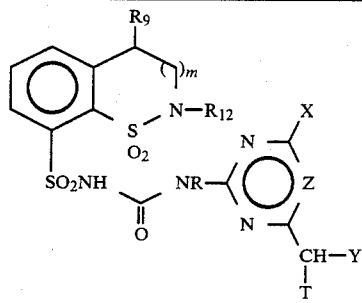

| R9 | R12 | R | m | X | T | Y | Z | m.p. (°C.) |
|---|---|---|---|---|---|---|---|---|
| H | CH2CH3 | H | 1 | CH3 | H | SePh | CH | |
| H | CH2CH3 | H | 1 | CH3 | H | SPh | CH | |
| H | CH2CH3 | H | 1 | CH3 | H | SPh | N | |
| H | CH3 | H | 1 | OCH2CH3 | H | SePh | CH | |
| H | CH3 | H | 1 | Cl | H | SPh | CH | |
| H | CH3 | H | 1 | F | H | SPh | CH | |
| H | CH3 | H | 1 | Br | H | SePh | CH | |
| H | CH3 | H | 1 | CF3 | H | SePh | CH | |
| H | CH3 | H | 1 | OCHF2 | H | SPh | CH | |
| H | CH2CH2CH3 | H | 1 | OCH3 | H | SeCH3 | CH | |
| H | CH2CH2CH3 | H | 1 | OCH3 | H | SePh | CH | |
| H | CH2CH2CH3 | H | 1 | OCH3 | H | SPh | CH | |
| H | CH2CH2CH3 | H | 1 | OCH3 | H | SO2Ph | CH | |
| H | CH2CH2CH3 | H | 1 | OCH3 | H | OPh | CH | |
| H | CH3 | H | 0 | OCH3 | H | OSi(CH3)3 | CH | |
| H | CH3 | H | 1 | OCH3 | H | OSi(CH3)3 | CH | |
| H | CH3 | H | 1 | OCH3 | H | CH2OH | CH | |
| CH3 | CH3 | H | 0 | CH3 | H | CH2OSi(CH3)2 | N | |

TABLE 7b

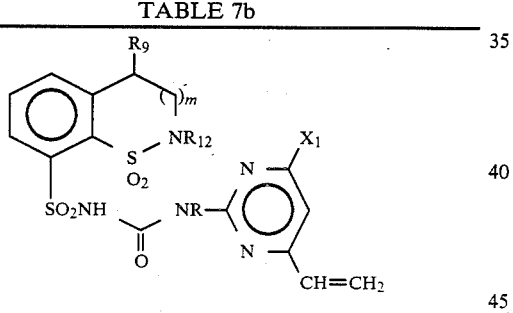

| R9 | R12 | R | m | X1 | m.p. (°C.) |
|---|---|---|---|---|---|
| H | CH3 | H | 0 | CH3 | |
| H | CH3 | H | 0 | OCH3 | |
| H | CH3 | H | 0 | OCH2CH3 | |
| CH3 | CH3 | H | 0 | OCH3 | |
| H | CH2CH3 | H | 0 | CH3 | |
| H | CH2CH3 | H | 0 | OCH3 | |
| H | CH2CH3 | H | 0 | OCH2CH3 | |
| H | CH2CH2CH3 | H | 0 | OCH3 | |
| H | CH2CH2CH3 | H | 0 | CH3 | |
| H | CH2CH2CH3 | H | 0 | OCH2CH3 | |
| H | CH3 | H | 1 | CH3 | |
| H | CH3 | H | 1 | OCH3 | |
| H | CH3 | H | 1 | OCH2CH3 | |
| CH3 | CH3 | H | 0 | CH3 | |
| H | CH2CH3 | H | 1 | CH3 | |
| H | CH2CH3 | H | 1 | OCH3 | |
| H | CH2CH3 | H | 1 | OCH2CH3 | |
| H | CH2CH2CH3 | H | 1 | CH3 | |
| H | CH2CH2CH3 | H | 1 | OCH3 | |
| H | CH2CH2CH3 | H | 1 | OCH2CH3 | |
| H | CH3 | CH3 | 0 | OCH3 | |

TABLE 7c

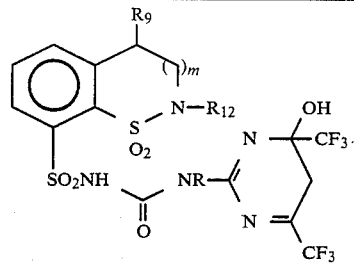

| R9 | R12 | R | m | m.p. (°C.) |
|---|---|---|---|---|
| H | CH3 | H | 0 | |
| H | CH2CH3 | H | 0 | |
| H | CH2CH2CH3 | H | 0 | |
| CH3 | CH3 | H | 0 | |
| H | CH3 | CH3 | 0 | |
| CH3 | CH2CH3 | H | 0 | |
| H | CH3 | H | 1 | |
| H | CH2CH3 | H | 1 | |
| H | CH2CH2CH3 | H | 1 | |
| H | CH3 | CH3 | 1 | |

TABLE 7d

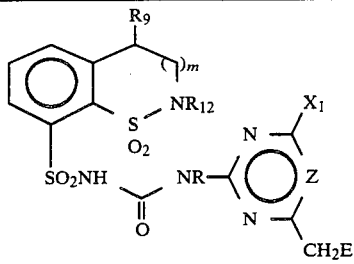

| R9 | R12 | R | m | X1 | E | Z |
|---|---|---|---|---|---|---|
| H | CH3 | H | 0 | OCH3 | Cl | CH |
| H | CH3 | H | 0 | OCH3 | Br | CH |
| H | CH2CH3 | H | 0 | OCH3 | Cl | CH |
| H | CH2CH3 | H | 0 | OCH3 | Br | CH |
| H | CH2CH2CH3 | H | 0 | OCH3 | Cl | CH |
| H | CH3 | H | 0 | OCH3 | Br | N |
| H | CH3 | H | 1 | OCH3 | Cl | CH |
| H | CH3 | H | 1 | OCH3 | Br | CH |
| H | CH2CH3 | H | 1 | OCH3 | Cl | CH |
| H | CH2CH3 | H | 1 | OCH3 | Br | CH |
| H | CH2CH2CH3 | H | 1 | OCH3 | Cl | CH |
| H | CH3 | H | 1 | OCH2CH3 | Br | CH |
| H | CH2CH3 | H | 1 | OCH2CH3 | Cl | CH |
| H | CH2CH2CH3 | H | 1 | OCH2CH3 | Cl | CH |
| H | CH3 | H | 1 | OCH3 | Br | N |

TABLE 7e

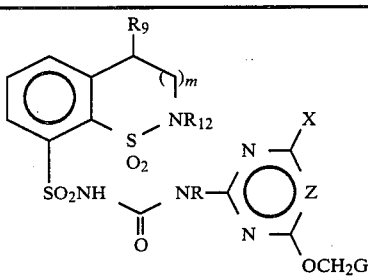

| R9 | R12 | R | m | X | Z | G | m.p. (°C.) |
|---|---|---|---|---|---|---|---|
| H | CH3 | H | 0 | OCH3 | CH | CH(—OCH2CH2O—) | |
| CH3 | CH3 | H | 0 | CH3 | CH | CH(—OCH2CH2O—) | |
| H | CH3 | H | 1 | OCH3 | N | CH(—OCH2CH2O—) | |
| H | CH3 | H | 1 | OCH3 | CH | CH(OCH3)2 | |
| H | C2H5 | H | 0 | OCH3 | CH | C6H5 | |
| H | C3H7 | H | 0 | OCH3 | CH | CH(OCH3)2 | |
| H | CH3 | H | 0 | OCH3 | CH | CH(—OCH2CH2O—) | |

TABLE 8a

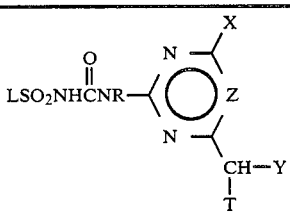

| L | m | R9 | R | X | T | Y | Z | m.p. (°C.) |
|---|---|---|---|---|---|---|---|---|
| L-11 | 0 | H | H | OCH3 | H | SeCH3 | CH | |
| L-11 | 0 | H | H | OCH3 | H | SePh | CH | |
| L-11 | 0 | H | H | OCH3 | H | SPh | CH | |
| L-11 | 0 | H | H | OCH3 | H | SO2Ph | CH | |
| L-11 | 0 | H | H | OCH3 | H | OPh | CH | |
| L-11 | 0 | H | H | OCH3 | SeCH3 | SeCH3 | CH | |
| L-11 | 0 | H | H | OCH3 | SPh | SPh | CH | |
| L-11 | 0 | H | H | OCH3 | SCH3 | SeCH3 | CH | |

TABLE 8a-continued

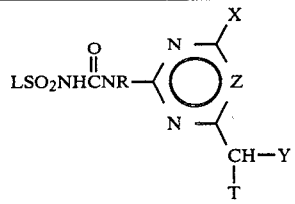

| L | m | R9 | R | X | T | Y | Z | m.p. (°C.) |
|---|---|---|---|---|---|---|---|---|
| L-11 | 0 | H | H | OCH3 | H | SeCH3 | N | |
| L-11 | 0 | H | H | OCH3 | H | SPh | N | |
| L-11 | 0 | H | H | CH3 | H | SeCH3 | CH | |
| L-11 | 0 | H | H | CH3 | H | SePh | CH | |
| L-11 | 0 | H | H | CH3 | H | SPh | CH | |
| L-11 | 0 | H | H | CH3 | H | SO2Ph | CH | |
| L-11 | 0 | H | H | OCH2CH3 | H | SPh | CH | |
| L-11 | 0 | H | H | OCHF2 | H | SPh | CH | |
| L-11 | 0 | H | H | Cl | H | SePh | CH | |
| L-11 | 0 | H | H | CF3 | H | SPh | CH | |
| L-11 | 0 | CH3 | H | OCH3 | H | SeCH3 | CH | |
| L-11 | 0 | CH3 | H | OCH3 | H | SPh | CH | |
| L-11 | 1 | H | H | OCH3 | H | SeCH3 | CH | |
| L-11 | 1 | H | H | OCH3 | H | SePh | CH | |
| L-11 | 1 | H | H | OCH3 | H | SPh | CH | |
| L-11 | 1 | H | H | OCH3 | H | SO2Ph | CH | |
| L-11 | 1 | H | H | OCH3 | H | OPh | CH | |
| L-11 | 1 | H | H | OCH3 | SeCH3 | SeCH3 | CH | |
| L-11 | 1 | H | H | OCH3 | SPh | SPh | CH | |
| L-11 | 1 | H | H | OCH3 | SCH3 | SeCH3 | CH | |
| L-11 | 1 | H | H | OCH3 | H | SeCH3 | N | |
| L-11 | 1 | H | H | OCH3 | H | SPh | N | |
| L-11 | 1 | H | H | CH3 | H | SeCH3 | CH | |
| L-11 | 1 | H | H | CH3 | H | SePh | CH | |
| L-11 | 1 | H | H | CH3 | H | SPh | CH | |
| L-11 | 1 | H | H | CH3 | H | SO2Ph | CH | |
| L-11 | 1 | H | H | OCH2CH3 | H | SPh | CH | |
| L-11 | 1 | H | H | OCHF2 | H | SPh | CH | |
| L-11 | 1 | H | H | Cl | H | SePh | CH | |
| L-11 | 1 | H | H | CF3 | H | SPh | CH | |
| L-12 | 0 | H | H | OCH3 | H | SeCH3 | CH | |
| L-12 | 0 | H | H | OCH3 | H | SePh | CH | |
| L-12 | 0 | H | H | OCH3 | H | SPh | CH | |
| L-12 | 0 | H | H | OCH3 | H | SO2Ph | CH | |
| L-12 | 0 | H | H | OCH3 | H | OPh | CH | |
| L-12 | 0 | H | H | OCH3 | SeCH3 | SeCH3 | CH | |
| L-12 | 0 | H | H | OCH3 | SPh | SPh | CH | |
| L-12 | 0 | H | H | OCH3 | SCH3 | SeCH3 | CH | |
| L-12 | 0 | H | H | OCH3 | H | SeCH3 | N | |
| L-12 | 0 | H | H | OCH3 | H | SPh | N | |
| L-12 | 0 | H | H | CH3 | H | SeCH3 | CH | |
| L-12 | 0 | H | H | CH3 | H | SePh | CH | |
| L-12 | 0 | H | H | CH3 | H | SPh | CH | |
| L-12 | 0 | H | H | CH3 | H | SO2Ph | CH | |
| L-12 | 0 | H | H | OCH2CH3 | H | SPh | CH | |
| L-12 | 0 | H | H | OCHF2 | H | SPh | CH | |
| L-12 | 0 | H | H | Cl | H | SePh | CH | |
| L-12 | 0 | H | H | CF3 | H | SPh | CH | |
| L-12 | 0 | CH3 | H | OCH3 | H | SeCH3 | CH | |
| L-12 | 0 | CH3 | H | OCH3 | H | SPh | CH | |
| L-12 | 1 | H | H | OCH3 | H | SeCH3 | CH | |
| L-12 | 1 | H | H | OCH3 | H | SePh | CH | |
| L-12 | 1 | H | H | OCH3 | H | SPh | CH | |
| L-12 | 1 | H | H | OCH3 | H | SO2Ph | CH | |
| L-12 | 1 | H | H | OCH3 | H | OPh | CH | |
| L-12 | 1 | H | H | OCH3 | SeCH3 | SeCH3 | CH | |
| L-12 | 1 | H | H | OCH3 | SPh | SPh | CH | |
| L-12 | 1 | H | H | OCH3 | SCH3 | SeCH3 | CH | |
| L-12 | 1 | H | H | OCH3 | H | SeCH3 | N | |
| L-12 | 1 | H | H | OCH3 | H | SPh | N | |
| L-12 | 1 | H | H | CH3 | H | SeCH3 | CH | |
| L-12 | 1 | H | H | CH3 | H | SePh | CH | |
| L-12 | 1 | H | H | CH3 | H | SPh | CH | |
| L-12 | 1 | H | H | CH3 | H | SO2Ph | CH | |
| L-12 | 1 | H | H | OCH2CH3 | H | SPh | CH | |
| L-12 | 1 | H | H | OCHF2 | H | SPh | CH | |
| L-12 | 1 | H | H | Cl | H | SePh | CH | |
| L-12 | 1 | H | H | CF3 | H | SPh | CH | |
| L-13 | 0 | H | H | OCH3 | H | SeCH3 | CH | |

TABLE 8a-continued

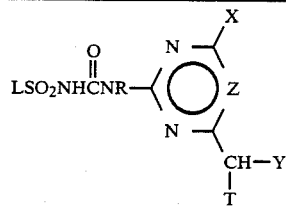

| L | m | R9 | R | X | T | Y | Z | m.p. (°C.) |
|---|---|----|---|---|---|---|---|------------|
| L-13 | 0 | H | H | OCH3 | H | SePh | CH | |
| L-13 | 0 | H | H | OCH3 | H | SPh | CH | |
| L-13 | 0 | H | H | OCH3 | H | SO2Ph | CH | |
| L-13 | 0 | H | H | OCH3 | H | OPh | CH | |
| L-13 | 0 | H | H | OCH3 | SeCH3 | SeCH3 | CH | |
| L-13 | 0 | H | H | OCH3 | SPh | SPh | CH | |
| L-13 | 0 | H | H | OCH3 | SCH3 | SeCH3 | CH | |
| L-13 | 0 | H | H | OCH3 | H | SeCH3 | N | |
| L-13 | 0 | H | H | OCH3 | H | SPh | N | |
| L-13 | 0 | H | H | CH3 | H | SeCH3 | CH | |
| L-13 | 0 | H | H | CH3 | H | SePh | CH | |
| L-13 | 0 | H | H | CH3 | H | SPh | CH | |
| L-13 | 0 | H | H | CH3 | H | SO2Ph | CH | |
| L-13 | 0 | H | H | OCH2CH3 | H | SPh | CH | |
| L-13 | 0 | H | H | OCHF2 | H | SPh | CH | |
| L-13 | 0 | H | H | Cl | H | SePh | CH | |
| L-13 | 0 | H | H | CF3 | H | SPh | CH | |
| L-13 | 0 | CH3 | H | OCH3 | H | SeCH3 | CH | |
| L-13 | 0 | CH3 | H | OCH3 | H | SPh | CH | |
| L-13 | 1 | H | H | OCH3 | H | SeCH3 | CH | |
| L-13 | 1 | H | H | OCH3 | H | SePh | CH | |
| L-13 | 1 | H | H | OCH3 | H | SPh | CH | |
| L-13 | 1 | H | H | OCH3 | H | SO2Ph | CH | |
| L-13 | 1 | H | H | OCH3 | H | OPh | CH | |
| L-13 | 1 | H | H | OCH3 | SeCH3 | SeCH3 | CH | |
| L-13 | 1 | H | H | OCH3 | SPh | SPh | CH | |
| L-13 | 1 | H | H | OCH3 | SCH3 | SeCH3 | CH | |
| L-13 | 1 | H | H | OCH3 | H | SeCH3 | N | |
| L-13 | 1 | H | H | OCH3 | H | SPh | N | |
| L-13 | 1 | H | H | CH3 | H | SeCH3 | CH | |
| L-13 | 1 | H | H | CH3 | H | SePh | CH | |
| L-13 | 1 | H | H | CH3 | H | SPh | CH | |
| L-13 | 1 | H | H | CH3 | H | SO2Ph | CH | |
| L-13 | 1 | H | H | OCH2CH3 | H | SPh | CH | |
| L-13 | 1 | H | H | OCHF2 | H | SPh | CH | |
| L-13 | 1 | H | H | Cl | H | SePh | CH | |
| L-13 | 1 | H | H | CF3 | H | SPh | CH | |
| L-11 | 0 | H | H | OCH3 | H | CH2OH | CH | |
| L-12 | 1 | H | H | OCH3 | H | CH2OH | N | |
| L-13 | 1 | H | H | OCH3 | H | OSi(CH3)3 | CH | |

TABLE 8b

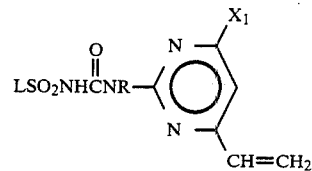

| L | R9 | R | X1 | m | m.p. (°C.) |
|---|----|---|----|----|------------|
| L-11 | H | H | CH3 | 0 | |
| L-11 | H | H | OCH3 | 0 | |
| L-11 | H | H | OCH2CH3 | 0 | |
| L-11 | CH3 | H | OCH3 | 0 | |
| L-11 | H | H | CH3 | 1 | |
| L-11 | H | H | OCH3 | 1 | |
| L-11 | H | H | OCH2CH3 | 1 | |
| L-12 | H | H | CH3 | 0 | |
| L-12 | H | H | OCH3 | 0 | |
| L-12 | H | H | OCH2CH3 | 0 | |
| L-12 | CH3 | H | OCH3 | 0 | |
| L-12 | H | H | CH3 | 1 | |
| L-12 | H | H | OCH3 | 1 | |
| L-12 | H | H | OCH2CH3 | 1 | |

TABLE 8b-continued

| L | R9 | R | X1 | m | m.p. (°C.) |
|---|----|---|----|----|------------|
| L-13 | H | H | CH3 | 0 | |
| L-13 | H | H | OCH3 | 0 | |
| L-13 | H | H | OCH2CH3 | 0 | |
| L-13 | H | H | CH3 | 1 | |
| L-13 | H | H | OCH3 | 1 | |
| L-13 | H | H | OCH2CH3 | 1 | |

TABLE 8c

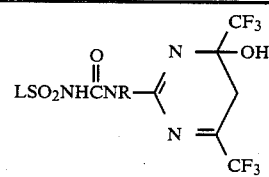

| L | R9 | R | m | m.p. (°C.) |
|---|----|---|----|------------|
| L-11 | H | H | 0 | |
| L-11 | CH3 | H | 0 | |
| L-11 | CH3 | CH3 | 0 | |
| L-11 | H | H | 1 | |
| L-11 | H | CH3 | 1 | |
| L-12 | H | H | 0 | |
| L-12 | CH3 | H | 0 | |
| L-12 | CH3 | CH3 | 0 | |
| L-12 | H | H | 1 | |
| L-12 | H | CH3 | 1 | |
| L-13 | CH3 | H | 0 | |
| L-13 | H | H | 1 | |

TABLE 8d

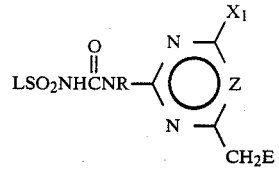

| L | R9 | R | m | X1 | E | Z | m.p. (°C.) |
|---|----|---|----|----|---|---|------------|
| L-12 | H | H | 0 | OCH3 | Cl | CH | |
| L-12 | H | H | 0 | OCH3 | Br | CH | |
| L-12 | H | H | 0 | CH3 | Cl | CH | |
| L-12 | H | H | 0 | CH2CH3 | Br | CH | |
| L-12 | H | H | 0 | OCH3 | Cl | N | |
| L-12 | H | H | 1 | OCH3 | Cl | CH | |
| L-12 | H | H | 1 | OCH3 | Br | CH | |
| L-12 | H | H | 1 | CH3 | Cl | CH | |
| L-12 | H | H | 1 | CH2CH3 | Br | CH | |
| L-12 | H | H | 1 | OCH3 | Cl | N | |
| L-12 | CH3 | H | 0 | OCH3 | Cl | CH | |
| L-12 | H | CH3 | 0 | OCH3 | Cl | CH | |
| L-13 | H | H | 0 | OCH3 | Cl | CH | |
| L-13 | H | H | 0 | OCH3 | Br | CH | |
| L-13 | H | H | 1 | OCH3 | Cl | CH | |
| L-13 | H | H | 1 | OCH3 | Br | CH | |

TABLE 8e

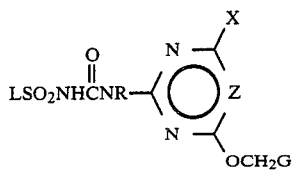

| L | R9 | R | m | X | Z | G | m.p. (°C.) |
|---|---|---|---|---|---|---|---|
| L-11 | H | H | 0 | OCH3 | CH | CH(OCH3)2 | |
| L-11 | H | H | 0 | CH3 | CH | CH(—OCH2CH2O—) | |
| L-11 | H | H | 1 | OCH3 | N | CH(—OCH2CH2O—) | |
| L-11 | CH3 | H | 1 | OCH3 | CH | CH(OCH3)2 | |
| L-12 | H | H | 0 | OCH3 | CH | CH(OCH3)2 | |
| L-12 | H | H | 1 | OCH3 | CH | CH(—OCH2CH2O—) | |
| L-13 | H | H | 0 | OCH3 | CH | C6H5 | |
| L-13 | H | H | 1 | OCH3 | CH | CH(—OCH2CH2O—) | |

TABLE 9a

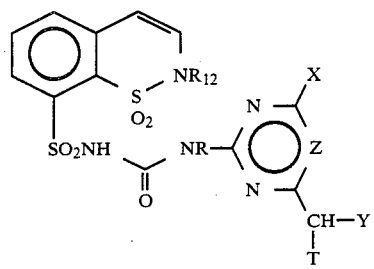

| R12 | R | X | T | Y | Z | m.p (°C). |
|---|---|---|---|---|---|---|
| CH3 | H | OCH3 | H | SeCH3 | CH | |
| CH3 | H | OCH3 | H | SePh | CH | |
| CH3 | H | CH3 | H | SPh | CH | |
| CH3 | H | CH3 | H | SO2Ph | CH | |
| CH3 | H | OCH3 | H | OPh | CH | |
| CH3 | H | OCH3 | SeCH3 | SeCH3 | CH | |
| CH3 | H | OCH3 | SPh | SPh | CH | |
| CH3 | H | OCH3 | H | SPh | N | |
| CH2CH3 | H | OCH3 | H | SeCH3 | CH | |
| CH2CH3 | H | OCH3 | H | SPh | CH | |
| CH2CH3 | H | OCH3 | H | OPh | CH | |
| CH2CH3 | H | CH3 | H | SePh | CH | |
| CH2CH3 | H | CH3 | H | SO2Ph | CH | |
| CH2CH2CH3 | H | OCH3 | H | SeCH3 | CH | |
| CH2CH2CH3 | H | OCH3 | H | OPh | CH | |
| CH2CH2CH3 | H | OCH3 | SeCH3 | SeCH3 | CH | |
| CH2CH2CH3 | H | OCH3 | H | SPh | N | |
| CH2CH2CH3 | H | OCH3 | SPh | SPh | N | |
| CH3 | H | Cl | H | SPh | CH | |
| CH3 | H | CF3 | H | SePH | CH | |
| CH3 | H | OCF2H | H | OPh | CH | |
| CH3 | H | OCH3 | H | CH2OH | CH | |
| CH2CH3 | H | CH3 | SCH3 | CH2OSi(CH3)3 | N | |

TABLE 9b

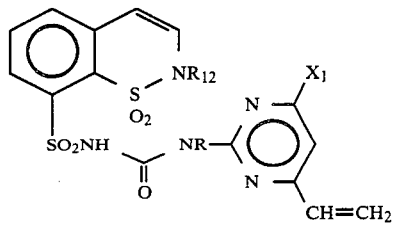

| R12 | R | X1 | m.p. (°C.) |
|---|---|---|---|
| CH3 | H | OCH3 | |
| CH3 | H | CH3 | |
| CH3 | H | OCH2CH3 | |
| CH2CH3 | H | OCH3 | |
| CH2CH3 | H | OCH2CH3 | |
| CH2CH2CH3 | H | OCH3 | |
| CH2CH2CH3 | H | CH3 | |
| CH3 | CH3 | OCH3 | |

TABLE 9c

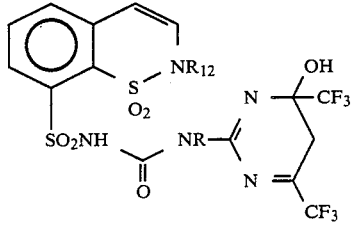

| R12 | R | m.p. (°C.) |
|---|---|---|
| CH3 | H | |
| CH2CH3 | H | |
| CH2CH2CH3 | H | |
| CH3 | CH3 | |

TABLE 9d

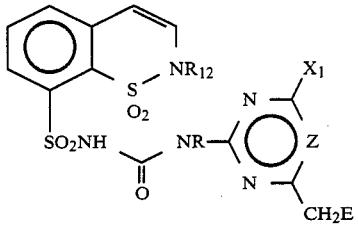

| R12 | R | X1 | E | Z | m.p. (°C.) |
|---|---|---|---|---|---|
| CH3 | H | CH3 | Cl | CH | |
| CH3 | H | CH3 | Br | CH | |
| CH3 | H | OCH3 | Cl | CH | |
| CH3 | H | OCH3 | Cl | N | |
| CH3 | H | OCH3 | Br | N | |
| CH2CH3 | H | CH3 | Cl | CH | |
| CH2CH3 | H | OCH3 | Cl | CH | |

TABLE 9d-continued

[Structure: benzene ring with CH=CH-S(O2)-NR12 group and SO2NH-C(=O)-NR-pyrimidine with X1, Z, and CH2E substituents]

| R12 | R | X1 | E | Z | m.p. (°C.) |
|---|---|---|---|---|---|
| CH2CH3 | H | OCH3 | Br | CH | |
| CH2CH2CH3 | H | OCH3 | Cl | CH | |
| CH3 | CH3 | OCH3 | Cl | CH | |

TABLE 9e

[Structure: benzene ring with CH=CH-S(O2)-NR12 group and SO2NH-C(=O)-NR-pyrimidine with X, Z, and OCH2G substituents]

| R12 | R | X | Z | G | m.p. (°C.) |
|---|---|---|---|---|---|
| CH3 | H | OCH3 | CH | CH(—OCH2CH2O—) | |
| CH3 | H | CH3 | CH | CH(—OCH2CH2O—) | |
| C2H5 | H | OCH3 | N | CH(OCH3)2 | |
| C2H5 | H | CH3 | CH | CH(OCH3)2 | |
| C3H7-n | H | OCH3 | CH | CH(OCH3)2 | |
| CH3 | CH3 | OCH3 | CH | CH(—OCH2CH2O—) | |
| CH3 | H | OCH3 | CH | C6H5 | |

TABLE 10a

[Structure: LSO2NHC(=O)NR-pyrimidine with X, Z, and CH(T)(Y) substituents]

| L | R13 | R14 | R | X | T | Y | Z | m.p. (°C.) |
|---|---|---|---|---|---|---|---|---|
| L-15 | H | — | H | OCH3 | H | SeCH3 | CH | |
| L-15 | H | — | H | OCH3 | H | SePh | CH | |
| L-15 | H | — | H | OCH3 | H | SPh | CH | |
| L-15 | H | — | H | OCH3 | H | OPh | CH | |
| L-15 | H | — | H | CH3 | H | SPh | CH | |
| L-15 | H | — | H | OCH3 | H | SPh | N | |
| L-15 | H | — | H | OCH3 | SeCH3 | SeCH3 | CH | |
| L-15 | H | — | H | OCH3 | SPh | SPh | CH | |
| L-15 | CH3 | — | H | OCH3 | H | SeCH3 | CH | |
| L-15 | CH3 | — | H | OCH3 | H | SePh | CH | |
| L-15 | CH3 | — | H | OCH3 | H | SPh | CH | |
| L-15 | CH3 | — | H | CH3 | H | SeCH3 | CH | |
| L-15 | CH3 | — | H | CH3 | H | SO2Ph | N | |
| L-15 | CH3 | — | H | OCH3 | SPh | SPh | CH | |
| L-15 | CH2CH3 | — | H | OCH3 | H | SeCH3 | CH | |
| L-15 | CH2CH3 | — | H | OCH3 | H | SPh | CH | |
| L-15 | CH2CH3 | — | H | CH3 | H | OPh | CH | |
| L-15 | CH2CH2CH3 | — | H | OCH3 | H | SPh | CH | |
| L-15 | CH3 | — | CH3 | OCH3 | H | SePh | CH | |
| L-15 | H | — | H | OCH2CH3 | H | SPh | CH | |
| L-15 | H | — | H | F | H | SPh | CH | |
| L-15 | H | — | H | Br | H | SeCH3 | CH | |
| L-15 | H | — | H | CF3 | H | SPh | CH | |
| L-15 | H | — | H | OCHF2 | H | SeCH3 | CH | |
| L-15 | H | — | CH3 | OCH3 | SPh | SPh | N | |
| L-16 | H | — | H | OCH3 | H | SeCH3 | CH | |
| L-16 | H | — | H | OCH3 | H | SePH | CH | |
| L-16 | H | — | H | OCH3 | H | SPh | CH | |
| L-16 | H | — | H | OCH3 | H | OPh | CH | |
| L-16 | H | — | H | CH3 | H | SPh | CH | |
| L-16 | H | — | H | OCH3 | H | SPh | N | |
| L-16 | H | — | H | OCH3 | SeCH3 | SeCH3 | CH | |
| L-16 | H | — | H | OCH3 | SPh | SPh | CH | |
| L-16 | CH3 | — | H | OCH3 | H | SeCH3 | CH | |
| L-16 | CH3 | — | H | OCH3 | H | SePh | CH | |
| L-16 | CH3 | — | H | OCH3 | H | SPh | CH | |
| L-16 | CH3 | — | H | CH3 | H | SeCH3 | CH | |
| L-16 | CH3 | — | H | CH3 | H | SO2Ph | N | |

TABLE 10a-continued

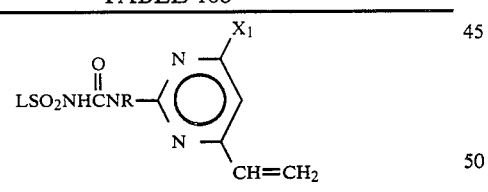

| L | R13 | R14 | R | X | T | Y | Z | m.p. (°C.) |
|---|---|---|---|---|---|---|---|---|
| L-16 | CH3 | — | H | OCH3 | SPh | SPh | CH | |
| L-16 | CH2CH3 | — | H | OCH3 | H | SeCH3 | CH | |
| L-16 | CH2CH3 | — | H | OCH3 | H | SPh | CH | |
| L-16 | CH2CH3 | — | H | CH3 | H | OPh | CH | |
| L-16 | CH2CH2CH3 | — | H | OCH3 | H | SPh | CH | |
| L-16 | CH3 | — | CH3 | OCH3 | H | SePh | CH | |
| L-16 | H | — | H | OCH2CH3 | H | SPh | CH | |
| L-16 | H | — | H | F | H | SPh | CH | |
| L-16 | H | — | H | Br | H | SeCH3 | CH | |
| L-16 | H | — | H | CF3 | H | SPh | CH | |
| L-16 | H | — | H | OCHF2 | H | SeCH3 | CH | |
| L-16 | H | — | CH3 | OCH3 | SPh | SPh | N | |
| L-17 | H | H | H | OCH3 | H | SeCH3 | CH | |
| L-17 | H | H | H | OCH3 | H | SePh | CH | |
| L-17 | H | H | H | OCH3 | H | SPh | CH | |
| L-17 | H | H | H | OCH3 | H | OPh | CH | |
| L-17 | H | H | H | CH3 | H | SPh | CH | |
| L-17 | CH3 | H | H | OCH3 | H | SPh | N | |
| L-17 | CH3 | H | H | OCH3 | SeCH3 | SeCH3 | CH | |
| L-17 | CH3 | H | H | OCH3 | SPh | SPh | CH | |
| L-17 | H | CH3 | H | OCH3 | H | SeCH3 | CH | |
| L-17 | H | CH3 | H | OCH3 | H | SePh | CH | |
| L-17 | H | CH3 | H | OCH3 | H | SPh | CH | |
| L-17 | H | CH3 | H | CH3 | H | SeCH3 | CH | |
| L-17 | H | CH3 | H | CH3 | H | SO2Ph | N | |
| L-17 | CH3 | CH3 | H | OCH3 | SPh | SPh | CH | |
| L-17 | CH3 | CH3 | CH3 | OCH3 | H | SePh | CH | |
| L-17 | CH3 | H | H | OCH2CH3 | H | SPh | CH | |
| L-17 | CH3 | H | H | F | H | SPh | CH | |
| L-17 | CH3 | H | H | Br | H | SeCH3 | CH | |
| L-17 | CH3 | H | H | CF3 | H | SPh | CH | |
| L-17 | CH3 | H | H | OCHF2 | H | SeCH3 | CH | |
| L-17 | CH3 | H | CH3 | OCH3 | SPh | SPh | N | |
| L-15 | CH3 | — | CH3 | OCH3 | H | CH2OH | CH | |
| L-16 | CH3 | — | CH3 | OCH3 | H | CH2OH | N | |
| L-17 | CH3 | H | CH3 | OCH3 | H | CH2OH | N | |

TABLE 10b

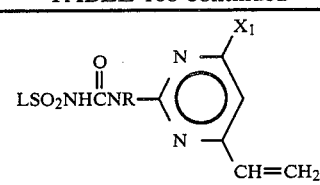

| L | R13 | R14 | R | X1 | m.p. (°C.) |
|---|---|---|---|---|---|
| L-15 | H | — | H | CH3 | |
| L-15 | H | — | H | OCH3 | |
| L-15 | H | — | H | OCH2CH3 | |
| L-15 | CH3 | — | H | CH3 | |
| L-15 | CH3 | — | H | OCH3 | |
| L-15 | CH3 | — | H | OCH2CH3 | |
| L-15 | CH2CH3 | — | H | CH3 | |
| L-15 | CH2CH3 | — | H | OCH3 | |
| L-15 | CH2CH3 | — | H | OCH2CH3 | |
| L-15 | CH2CH2CH3 | — | H | OCH3 | |
| L-15 | CH3 | — | CH3 | OCH3 | |
| L-15 | H | — | CH3 | OCH3 | |
| L-16 | H | — | H | CH3 | |
| L-16 | H | — | H | OCH3 | |
| L-16 | H | — | H | OCH2CH3 | |
| L-16 | CH3 | — | H | CH3 | |
| L-16 | CH3 | — | H | OCH3 | |
| L-16 | CH3 | — | H | OCH2CH3 | |
| L-16 | CH2CH3 | — | H | CH3 | |

TABLE 10b-continued

| L | R13 | R14 | R | X1 | m.p. (°C.) |
|---|---|---|---|---|---|
| L-16 | CH2CH3 | — | H | OCH3 | |
| L-16 | CH2CH3 | — | H | OCH2CH3 | |
| L-16 | CH2CH2CH3 | — | H | OCH3 | |
| L-16 | CH3 | — | CH3 | OCH3 | |
| L-16 | H | — | CH3 | OCH3 | |
| L-17 | H | H | H | CH3 | |
| L-17 | H | H | H | OCH3 | |
| L-17 | H | H | H | OCH2CH3 | |
| L-17 | CH3 | CH3 | H | CH3 | |
| L-17 | CH3 | CH3 | H | OCH3 | |
| L-17 | CH3 | CH3 | H | OCH2CH3 | |
| L-17 | CH3 | CH3 | CH3 | OCH3 | |
| L-17 | CH3 | H | CH3 | OCH3 | |

TABLE 10c

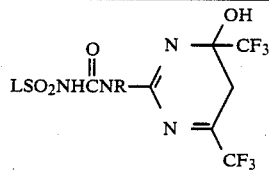

| L | R₁₃ | R₁₄ | R | m.p. (°C.) |
|---|---|---|---|---|
| L-15 | H | — | H | |
| L-15 | CH₃ | — | H | |
| L-15 | CH₂CH₃ | — | H | |
| L-15 | CH₂CH₂CH₃ | — | H | |
| L-15 | CH₃ | — | CH₃ | |
| L-16 | H | — | H | |
| L-16 | CH₃ | — | H | |
| L-16 | CH₂CH₃ | — | H | |
| L-16 | CH₂CH₂CH₃ | — | H | |
| L-16 | CH₃ | — | CH₃ | |
| L-17 | H | H | H | |
| L-17 | H | CH₃ | H | |
| L-17 | H | CH₂CH₃ | H | |
| L-17 | CH₃ | CH₂CH₂CH₃ | H | |
| L-17 | CH₃ | CH₃ | CH₃ | |

TABLE 10d

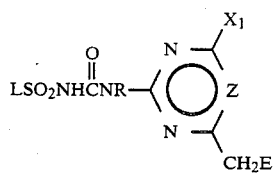

| L | R₁₃ | R₁₄ | R | X₁ | E | Z | m.p. (°C.) |
|---|---|---|---|---|---|---|---|
| L-15 | H | — | H | OCH₃ | Cl | CH | |
| L-15 | H | — | H | OCH₃ | Br | CH | |
| L-15 | H | — | H | OCH₃ | Cl | N | |
| L-15 | H | — | H | CH₃ | Cl | CH | |
| L-15 | H | — | H | OCH₂CH₃ | Cl | CH | |
| L-15 | CH₃ | — | H | OCH₃ | Cl | CH | |
| L-15 | CH₃ | — | H | OCH₃ | Br | CH | |
| L-15 | CH₃ | — | H | CH₃ | Cl | CH | |
| L-15 | CH₃ | — | H | CH₃ | Cl | N | |
| L-15 | CH₂CH₃ | — | H | OCH₃ | Cl | CH | |
| L-15 | CH₂CH₃ | — | H | OCH₃ | Br | CH | |
| L-15 | CH₂CH₃ | — | H | OCH₃ | Cl | N | |
| L-15 | CH₂CH₃ | — | H | CH₃ | Cl | CH | |
| L-15 | CH₂CH₂CH₃ | — | H | OCH₃ | Cl | CH | |
| L-15 | CH₂CH₂CH₃ | — | H | OCH₃ | Cl | N | |
| L-15 | H | — | CH₃ | OCH₃ | Cl | CH | |
| L-15 | CH₃ | — | CH₃ | OCH₃ | Br | CH | |

TABLE 10d-continued

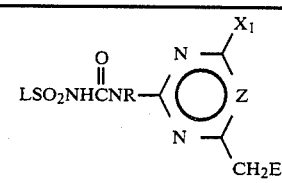

| L | R₁₃ | R₁₄ | R | X₁ | E | Z | m.p. (°C.) |
|---|---|---|---|---|---|---|---|
| L-16 | H | — | H | OCH₃ | Cl | CH | |
| L-16 | H | — | H | OCH₃ | Br | CH | |
| L-16 | H | — | H | OCH₃ | Cl | N | |
| L-16 | H | — | H | CH₃ | Cl | CH | |
| L-16 | H | — | H | OCH₂CH₃ | Cl | CH | |
| L-16 | CH₃ | — | H | OCH₃ | Cl | CH | |
| L-16 | CH₃ | — | H | OCH₃ | Br | CH | |
| L-16 | CH₃ | — | H | CH₃ | Cl | CH | |
| L-16 | CH₃ | — | H | CH₃ | Cl | N | |
| L-16 | CH₂CH₃ | — | H | OCH₃ | Cl | CH | |
| L-16 | CH₂CH₃ | — | H | OCH₃ | Br | CH | |
| L-16 | CH₂CH₃ | — | H | OCH₃ | Cl | N | |
| L-16 | CH₂CH₃ | — | H | CH₃ | Cl | CH | |
| L-16 | CH₂CH₂CH₃ | — | H | OCH₃ | Cl | CH | |
| L-16 | CH₂CH₂CH₃ | — | H | OCH₃ | Cl | N | |
| L-16 | H | — | CH₃ | OCH₃ | Cl | CH | |
| L-16 | CH₃ | — | CH₃ | OCH₃ | Br | CH | |

TABLE 10e

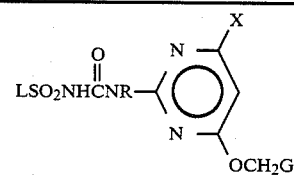

| L | R₁₃ | R₁₄ | R | X | Z | G | m.p. (°C.) |
|---|---|---|---|---|---|---|---|
| L-15 | H | — | H | OCH₃ | CH | CH(—OCH₂CH₂O—) | |
| L-15 | CH₃ | — | CH₃ | OCH₃ | CH | CH(OCH₃)₂ | |
| L-15 | H | — | H | CH₃ | CH | CH(OCH₃)₂ | |
| L-15 | C₃H₇—n | — | H | OCH₃ | N | CH(OCH₃)₂ | |
| L-16 | H | — | H | OCH₃ | CH | CH(OCH₃)₂ | |
| L-16 | CH₃ | — | H | OCH₃ | CH | C₆H₅ | |
| L-17 | H | H | H | OCH₃ | CH | CH(—OCH₂CH₂O—) | |
| L-17 | CH₃ | CH₃ | H | OCH₃ | CH | CH(OCH₃)₂ | |
| L-15 | H | — | H | OCH₃ | CH | C₆H₅ | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few points to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

| | Active Ingredient | Percent by Weight | |
|---|---|---|---|
| | | Diluent(s) | Surfactant(s) |
| Wettable Powders | 20-90 | 0-74 | 1-10 |
| Oil Suspensions, | 5-50 | 40-95 | 0-15 |

| | Active Ingredient | Percent by Weight | |
|---|---|---|---|
| | | Diluent(s) | Surfactant(s) |
| Emulsions, Solutions, (including Emulsifiable Concentrates) | | | |
| Aqueous Suspension | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foam, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 14

| Wettable Powder | |
|---|---|
| 2-[[[4-methoxy-6-(phenoxymethyl)pyrimidin-2-yl]aminocarbonyl]aminosulfonyl]benzoic acid, methyl ester | 50% |
| sodium alkylnaphthalenesulfonate | 2% |
| sodium ligninsulfonate | 2% |
| synthetic amorphous silica | 3% |
| kaolinite | 43% |

The ingredients are blended and hammer-milled.

EXAMPLE 15

| High Strength Concentrate | |
|---|---|
| 2-[[[4-methoxy-6-(phenoxymethyl)pyrimidin-2-yl]aminocarbonyl]aminosulfonyl]benzoic acid, methyl ester | 98.5% |
| silica aerogel | 0.5% |
| synthetic amorphous fine silica | 1.0% |

The ingredients are blended and ground in a hammer-mill to produce a high strength concentrate essentially all passing a U.S.S. No. 50 screen (0.3 mm opening). This material may be formulated in a variety of ways.

EXAMPLE 16

| Dust | |
|---|---|
| Wettable powder of Example 14 | 10% |
| pyrophyllite (powder) | 90% |

The wettable powder and the pyrophyllite diluent are thoroughly blended and then packaged. The product is suitable for use as a dust.

EXAMPLE 17

| Aqueous Suspension | |
|---|---|
| 2-[[[bis(4,6-trifluoromethyl)pyrimidin-2-yl]aminocarbonyl]aminosulfonyl]benzoic acid, methyl ester | 25% |
| hydrated attapulgite | 3% |
| crude calcium ligninsulfonate | 10% |
| water | 62% |

The ingredients are ground together in a ball, sand or roller mill until the solid particles have been reduced to diameters under 10 microns.

EXAMPLE 18

| Solution | |
|---|---|
| 2-[[[4-methoxy-6-(methylselenylmethyl)pyrimidin-2-yl]aminocarbonyl]aminosulfonyl]benzoic acid, methyl ester | 30% |
| dimethylformamide | 70% |

The ingredients are combined and stirred to produce a solution, which can be used for low volume applications.

EXAMPLE 19

| Granule | |
|---|---|
| Wettable Powder of Example 14 | 50% |
| sugar | 50% |

The ingredients are blended in a rotating or fluid bed mixer and water sprayed on to accomplish granulation. When most of the material has reached the desired range of 1.0 to 0.42 mm (U.S.S. #18 to 40 sieves), the granules are removed, dried, and screened. Oversize material is crushed to produce additional material in the desired range. These granules contain 25% active ingredient.

UTILITY

Test results indicate that the compounds of the present invention are active herbicides. They should have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, many of the subject compounds should be useful for the selective pre- or post-emergence weed control in crops, such as wheat and cotton.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.001 to 5 kg/ha, the lower rates being suggested for use on ligher soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types. They may also be used in combination with mefluidide.

The herbicidal properties of the subject compounds were discovered in a number of greenhouse tests. The test procedures and results follow.

Although some of the compounds do not exhibit a high degree of activity at the low rates tested, it is expected that these compounds will exhibit herbicidal effects at higher rates.

TEST A

Seeds of crabgrass (Digitaris sp.), barnyardgrass (Echinochloa crusgalli), wild oats (Avena fatua), sicklepod (Cassia obtusifolia), morningglory (Ipomoea sp.), cocklebur (Xanthium sp.), sorghum, corn, soybean, cotton, sugar beet, rice, wheat and purple nutsedge (Cyperus rotundus) tubers were planted and treated pre-emergence with the chemicals dissolved in a nonphytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

B=burn;
C=chlorosis or necrosis;
E=emergence inhibition;
G=growth retardation;
H=formative effects; and
U=unusual pigmentation.

Compounds

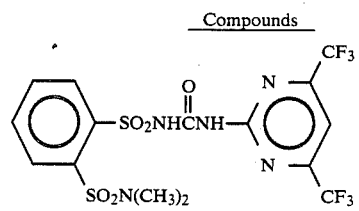

Compound 1

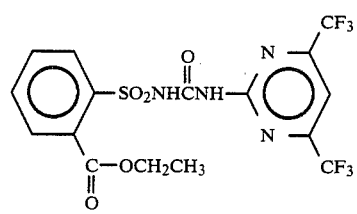

Compound 2

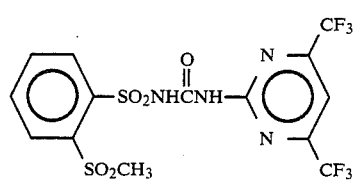

Compound 3

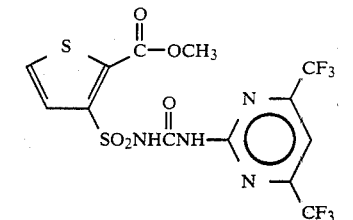

Compound 4

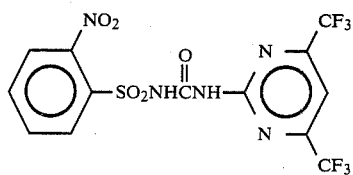

Compound 5

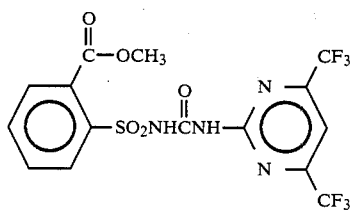

Compound 6

-continued
Compounds
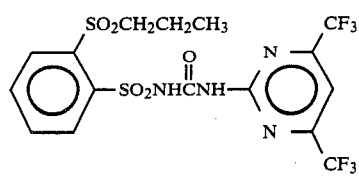
Compound 7
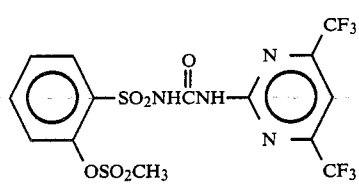
Compound 8
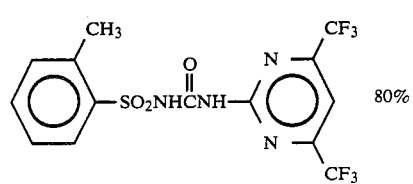
Compound 9
80%
and
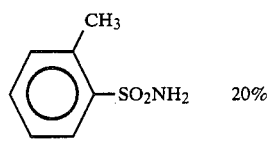
20%
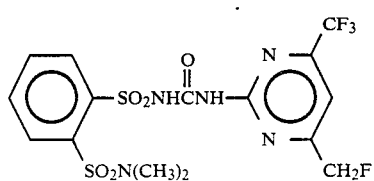
Compound 10
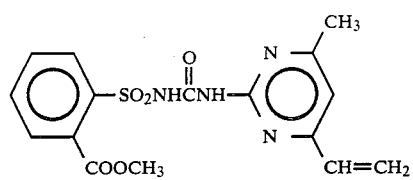
Compound 11
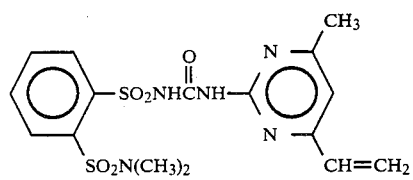
Compound 12
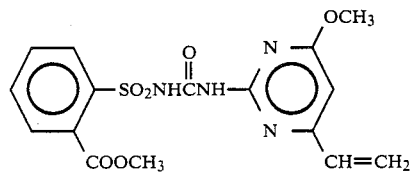
Compound 13
-continued
Compounds
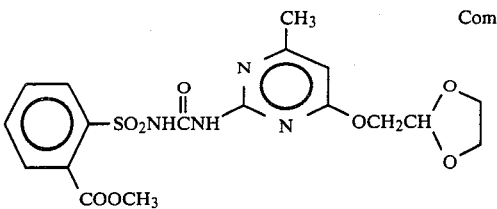
Compound 14
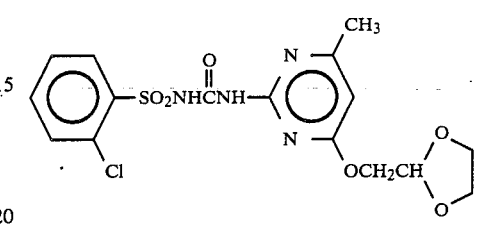
Compound 15
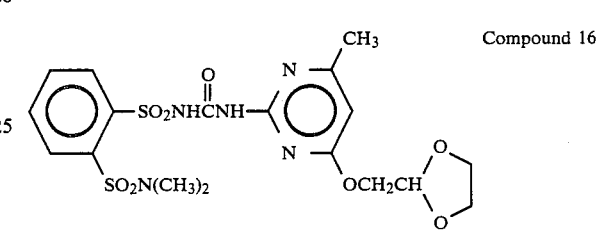
Compound 16
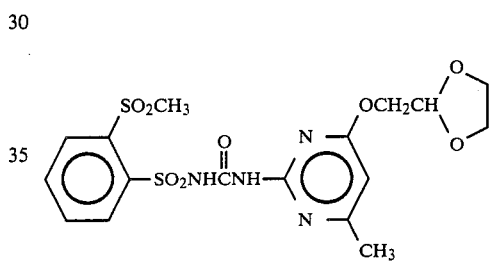
Compound 17
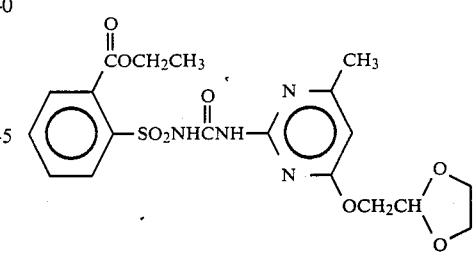
Compound 18
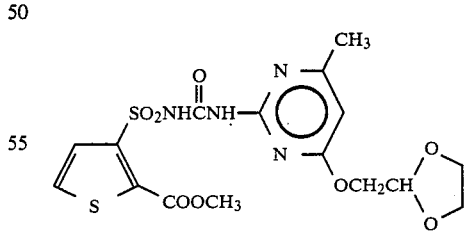
Compound 19
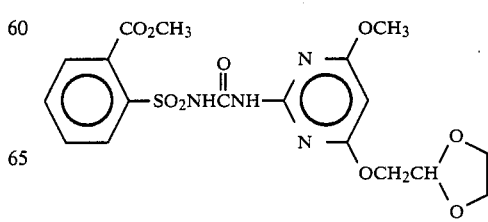
Compound 20

-continued
Compounds
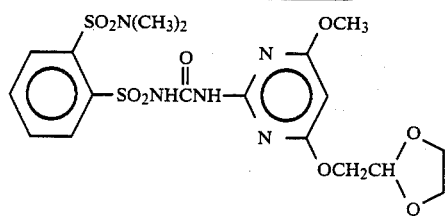
Compound 21
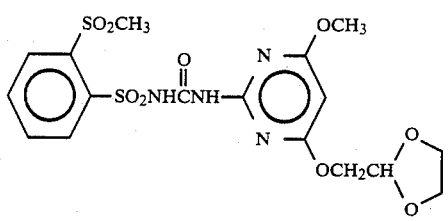
Compound 22
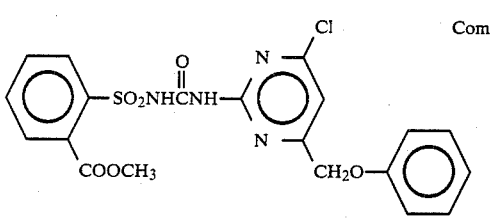
Compound 23
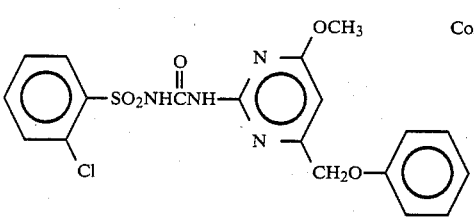
Compound 24
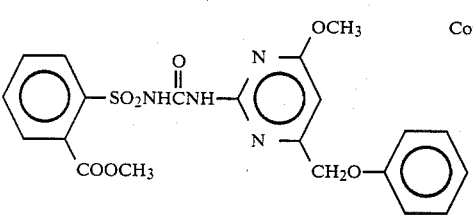
Compound 25
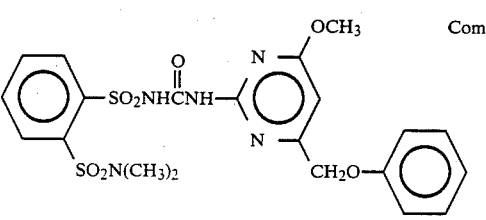
Compound 26
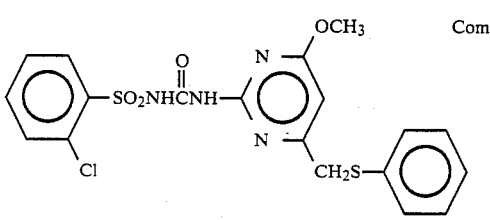
Compound 27
-continued
Compounds
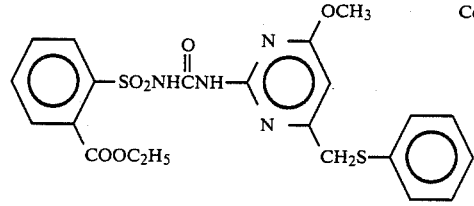
Compound 28
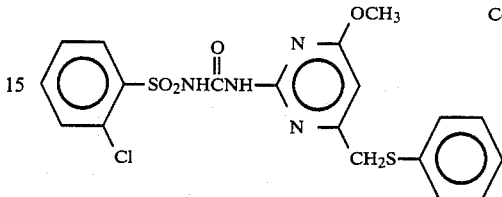
Compound 29
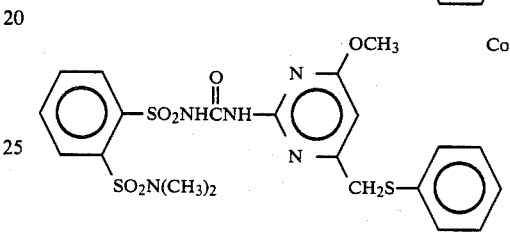
Compound 30
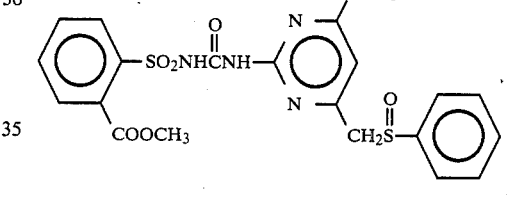
Compound 31
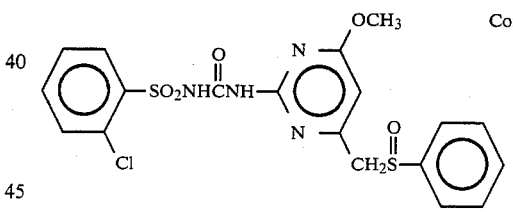
Compound 32
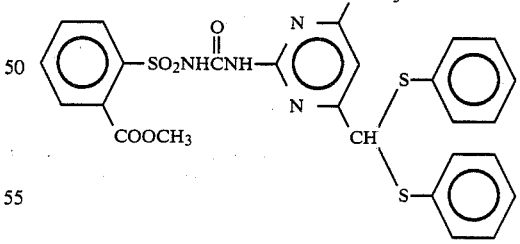
Compound 33
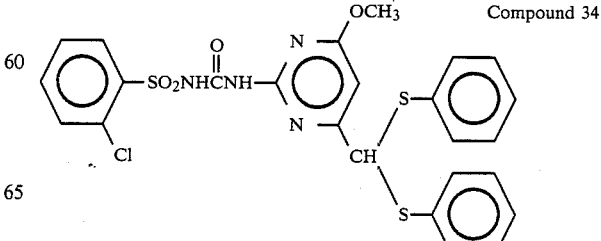
Compound 34

-continued
Compounds
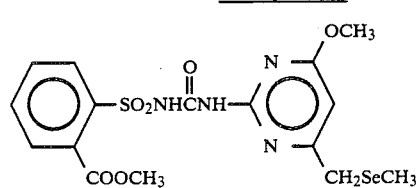
Compound 35
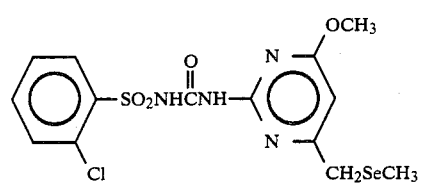
Compound 36
+
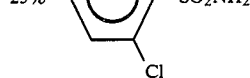 25%
-continued
Compounds
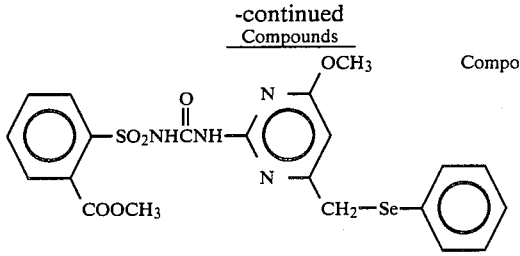
Compound 37
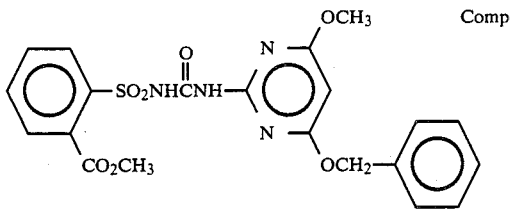
Compound 38
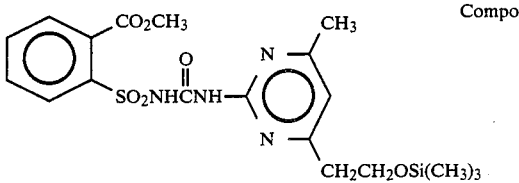
Compound 39

TABLE A

| Rate kg/ha | Cmpd. 1 0.05 | Cmpd. 2 0.05 | Cmpd. 3 0.05 | Cmpd. 4 0.05 | Cmpd. 5 0.05 | Cmpd. 6 0.05 | Cmpd. 7 0.05 | Cmpd. 8 0.05 | Cmpd. 9 0.05 | Cmpd. 10 0.05 | Cmpd. 11 0.05 | Cmpd. 12 0.05 | Cmpd. 13 0.05 | Cmpd. 14 0.05 | Cmpd. 15 0.05 |
|---|---|---|---|---|---|---|---|---|---|---|---|---|---|---|---|
| | | | | | | | POST-EMERGENCE | | | | | | | | |
| Morningglory | 9C | 2C,4H | 4C,8H | 0 | 5C,9G | 6C,9G | 2C,2H | 4C,9H | 2C,4H | 2C,7G | 3C,7G | 2C,4H | 1C | 0 | 0 |
| Cocklebur | 9C | 1C,2G | 4C,9H | 0 | 5C,9H | 6C,9H | 1C | 5C,9H | 1C | 2C,8H | 2C,5G | 5G | 1C,7G | 0 | 0 |
| Sicklepod | 2C,4G | 1C | 3C,3H | 0 | 2C,3H | 5C,6G | 0 | 3C,3H | 1C | 3G | 2G | 1C | 2C,5G | 5G | 5G |
| Nutsedge | 1C | 0 | 2C,8G | 0 | 3C,9G | 6C,9G | 0 | 3C,8G | 0 | 9G | 0 | 2C,8G | 2C,5G | 2G | 2G |
| Crabgrass | 1C | 0 | 2C,7G | 0 | 3H | 5G | 0 | 4G | 0 | 3G | 2G | 1C,3H | 9C | 0 | 0 |
| Barnyardgrass | 3C,8H | 0 | 9C | 0 | 9C | 9C | 1H | 1H | 5G | 3C,8H | 3C,9H | 2C,8H | 9C | 4C,9H | 4C,9H |
| Wild Oats | 2C,4G | 0 | 6C,9H | 0 | 4C,8G | 5C,9G | 0 | 5C,9G | 9C | 9C | 0 | 1C | 4C,8G | 0 | 0 |
| Wheat | 3C,8G | 0 | 5C,9G | 0 | 5C,9G | 9C | 0 | 6C,9G | 9C | 3C,5G | 3C,5G | 1C | 3C,9G | 0 | 0 |
| Corn | 2C,9H | 0 | 2C,9H | 0 | 6C,9H | 5C,9G | 0 | 5C,9G | 5U,9C | 0 | 3C,9G | 5C,9G | 2C,9G | 0 | 0 |
| Soybean | 3C,9G | 4G | 3C,8H | 0 | 4C,9H | 4C,9G | 0 | 4C,9H | 9C | 3C,9G | 3C,7H | 1C | 1C | 0 | 1H |
| Rice | 4C,9G | 3G | 4C,9G | 0 | 6C,9G | 5C,9G | 0 | 4C,9G | 5U,9C | 3C,7H | 4C,9G | 4G | 5C,9G | 0 | 2C,7G |
| Sorghum | 2C,9G | 2G | 4C,9G | 0 | 6C,9G | 6C,9G | 2C,5G | 5C,9G | 9C | 2C,9G | 2C,9G | 3C,9H | 4C,9G | 2C,5G | 2C,8G |
| Sugar beet | 9C | 2C,7G | 4C,8H | 0 | 4C,9G | 9C | 3C,7G | 9C | 2G | 2C,5H | 2C,5H | 2C,3H | 1C,4G | 1C | 1C |
| Cotton | 3C,9H | 0 | 4C,9H | 0 | 2C,8H | 4C,9H | 2C,5G | 3C,7H | 0 | 10C | 2C,3H | 1C,5G | 5C,9G | 1C | 1C |

| Rate kg/ha | Cmpd. 16 0.05 | Cmpd. 17 0.05 | Cmpd. 18 0.05 | Cmpd. 19 0.05 | Cmpd. 20 0.05 | Cmpd. 21 0.05 | Cmpd. 22 0.05 | Compound 23 0.05 | Compound 23 0.4 | Cmpd. 24 0.05 | Cmpd. 25 0.05 | Cmpd. 26 0.05 | Cmpd. 27 0.05 | Cmpd. 28 0.05 | Cmpd. 29 0.05 |
|---|---|---|---|---|---|---|---|---|---|---|---|---|---|---|---|
| | | | | | | | POST-EMERGENCE | | | | | | | | |
| Morningglory | 2C,5G | 0 | 0 | 0 | 2C,6G | 2C,5H | 3G | 2C,3H | 1C | 1C | 2C,7G | 3C,3H | 3C | 10C | 2G |
| Cocklebur | 2C,6G | 1C | 2H | 0 | 10C | 9C | 7H | 5C,9G | 6H | 10C | 10C | 9C | 9C | 10C | 2C,8G |
| Sicklepod | 0 | 0 | 0 | 0 | 2C,9G | 3C,8G | 2C,8G | 2C,4G | 1C | 2C | 2C,3G | 3G | 3G | 5C,9G | 2C |
| Nutsedge | 0 | 0 | 0 | 0 | 3C,7G | 8G | 2C,9G | 0 | 0 | 0 | 5G | 5G | 3C,8G | 2C,8G | 4G |
| Crabgrass | 2G | 2G | 0 | 4G | 5G | 3C,6G | 2C,5G | 6G | 2G | 5G | 2C,8G | 2C,5G | 3C,8G | 5C,9H | 0 |
| Barnyardgrass | 2C,7H | 3H | 3C,8H | 4C,8H | 3C,9H | 5C,9H | 5C,9G | 6G | 4H | 3C,9H | 5C,9H | 5C,9H | 5C,9H | 3C,9G | 3C,9H |
| Wild Oats | 1C | 0 | 0 | 0 | 2C,9G | 2C,9G | 3C,9G | 0 | 0 | 2C,8G | 5C,9H | 3C,9G | 2C,6G | 5G | 0 |
| Wheat | 8G | 3G | 0 | 0 | 7G | 9G | 9G | 2H | 0 | 6G | 2C,9G | 3G | 5G | 6G | 0 |
| Corn | 1C,1H | 2C,3H | 2C,6H | 1C | 9G | 3C,9H | 4C,9H | 1C,3G | 2C,9H | 5U,9C | 3C,9H | 9C | 3C,9G | 6G | 4C,9H |
| Soybean | 2C,2H | 4G | 2C,5H | 1C | 3C,8G | 3C,8G | 5C,9G | 3C,5G | 4C,9G | 2C,8G | 9C | 5C,9G | 4C,9G | 5C,9G | 3C,7H |
| Rice | 2C,8G | 2C,8G | 3C,9G | 2C,7G | 5C,9G | 5C,9G | 5C,9G | 8H | 5G | 4C,9G | 9C | 2C,9G | 3C,9G | 3C,9G | 2C,8G |
| Sorghum | 2C,7G | 3C,7G | 2C,8G | 2C,7G | 2C,9H | 1U,9G | 10,9G | 3C,8H | 2C,5G | 9C | 5C,9G | 3C,6H | 3C,9G | 4C,9G | 3C,9G |
| Sugar beet | 2C | 0 | 2H | 1C | 4C,6G | 2C,5G | 3G | 2G | 2G | 5C,9H | 10C | 2C,9G | 9C | 9C | 9C |
| Cotton | 2C,3H | 0 | 1C | 1C | 3C,6G | 4C,8G | 3C,8H | | | 10C | 9C | 9C | 5C,9G | 3C,8G | 4C,6G |

| Rate kg/ha | Cmpd. 30 0.05 | Cmpd. 31 0.05 | Cmpd. 32 0.05 | Cmpd. 33 0.05 | Cmpd. 34 0.05 | Cmpd. 35 0.05 | Cmpd. 36 0.05 | Cmpd. 37 0.05 | Cmpd. 38 0.05 | Cmpd. 39 0.05 |
|---|---|---|---|---|---|---|---|---|---|---|
| | | | | POST-EMERGENCE | | | | | | |
| Morningglory | 3C,8H | 3C,7H | 2C,5G | 3G | 4C,9G | 2C,6G | 10C | 5C,9G | 10C | 9C |
| Cocklebur | 9C | 5C,9G | 3C,9H | 8G | 9C | 9H | 9C | 9C | 5C,9G | 5C,9G |
| Sicklepod | 2C,2H | 2C,4G | 2C,5G | 1C | 9C | 8H | 9C | 9C | 9C | 5C,9G |
| Nutsedge | 2C,6G | 9G | 3G | 3G | 10C | 5G | 10C | 10C | 10C | 9G |
| Crabgrass | 2C,5G | 2C,7G | 3G | 2G | 3C,7G | 4G | 6G | 6G | 6G | 9G |
| Barnyardgrass | 3C,9H | 5C,9H | 5G | 3C,9H | 5C,9H | 9H | 9C | 5C,9H | 2G | 3C,9G |
| Wild Oats | 2C,5G | 4C,8G | 9H | 0 | 4C,9G | 3G | 9C | 9C | 9C | 9C |
| Wheat | 5G | 7G | 0 | 0 | 4C,9G | 3G | 4C,9G | 2C,6G | 6C,9G | 6C,9G |
| Corn | 2C,9H | 2C,9H | 2C,9H | 3C,8H | 4C,9G | 2C,9H | 5C,9G | 5C,9G | 6C,9G | 3U,9G |
| Soybean | 4C,9G | 3C,9G | 4C,9G | 3C,8G | 4C,9G | 2C,8G | 9C | 9G | 9C | 6C,9G |
| Rice | 4C,9G | 3C,9G | 4C,9G | 2C,7G | 5C,9G | 4C,9G | 5C,9G | 4C,9G | 5C,9G | 6C,9G |
| Sorghum | 3C,9H | 2C,9G | 2C,9G | 2C,7G | 9C | 5C,9G | 9C | 5C,9G | 2C,9G | 5C,9H |
| Sugar beet | 3C,7H | 9C | 9C | 3C,8H | 9C | 3C,6H | 9C | 9C | 2C,9G | 5C,9G |

TABLE A-continued

PRE-EMERGENCE

| | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 | Cmpd. 10 | Cmpd. 11 | Cmpd. 12 | Cmpd. 13 | Cmpd. 14 | Cmpd. 15 |
|---|---|---|---|---|---|---|---|---|---|---|---|---|---|---|---|
| Rate kg/ha | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |
| Morningglory | 2C,8H | 0 | 1C | 0 | 4C,9G | 9G | 1C | 3C,8H | 0 | 9H | 8H | 7H | 6G | 2C,7H | 0 |
| Cocklebur | 2C,8H | 0 | 0 | 0 | 3C,8H | 8H | 1H | 1C | 0 | 3C,9H | 9H | 8G | 9H | 8H | — |
| Sicklepod | 0 | 0 | 0 | 0 | 3C | 3C | 0 | 1C | 0 | 5C,9G | 5G | 0 | 2G | 2C,7G | 0 |
| Nutsedge | 1C | 0 | 0 | 0 | 3C,8G | 3C,9G | 0 | 3C,5G | 0 | 10E | 8G | 0 | 0 | 2C,5G | 0 |
| Crabgrass | 0 | 0 | 0 | 0 | 0 | 3G | 0 | 1C | 0 | 5C,9G | 8G | 0 | 0 | 2C,8H | 0 |
| Barnyardgrass | 2H | 0 | 0 | 0 | 5C,9H | 5C,9H | 0 | 2C,4H | 0 | 5C,9H | 3C,3H | 2C,8G | 2C,8G | 4C,8H | 2C |
| Wild Oats | 2C | 0 | 0 | 0 | 3C,6G | 5C,9G | 0 | 3C,8H | 0 | 6C,9H | 2C,8G | 0 | 2C,7G | 4C,9G | 1C |
| Wheat | 2G | 0 | 0 | 0 | 3C,9H | 2C,9H | 0 | 2G | 0 | 10E | 2C,8G | 2C,7G | 2C,5G | 4C,9H | 2G |
| Corn | 2C,8H | 0 | 2C,9H | 2C | 3C,8H | 3C,9H | 0 | 3C,9H | 0 | 10E | 9G | 5G | 3C,9H | 9H | 4G |
| Soybean | 1H | 0 | 0 | 1C | 3C,8H | 2C,5H | 0 | 3C,3H | 0 | 9H | 4C,6H | 0 | 3C,6H | 2C,2H | 0 |
| Rice | 0 | 0 | 3G | 3G | 9H | 10E | 0 | 3C,7G | 0 | 10E | 5C,9H | 8G | 3C,7H | 10H | 0 |
| Sorghum | 3C,9H | 0 | 2C,9H | 0 | 5C,9H | 5C,9H | 2C,5G | 3C,9H | 0 | 10E | 9H | 6H | 3C,9H | 9C | 2C,4G |
| Sugar beet | 5C,9H | 2H | 5C,9G | 0 | 5C,9G | 9C | 2G | 9C | 5G | 10E | 4C,8G | 6G | 8G | 9G | 0 |
| Cotton | 5G | 0 | 1C | 0 | 2C,5G | 2C,9G | 0 | 3C,7G | 0 | 9G | 8G | 3G | 6G | 8G | 0 |

| | Cmpd. 16 | Cmpd. 17 | Cmpd. 18 | Cmpd. 19 | Cmpd. 20 | Cmpd. 21 | Cmpd. 22 | Compound 23 | Cmpd. 24 | Cmpd. 25 | Cmpd. 26 | Cmpd. 27 | Cmpd. 28 | Cmpd. 29 |
|---|---|---|---|---|---|---|---|---|---|---|---|---|---|---|
| Rate kg/ha | 0.05 | 0.05 | 0.05 | 0.05 | 0.05 | 0.05 | 0.05 | 0.4 | 0.05 | 0.05 | 0.05 | 0.05 | 0.05 | 0.05 |
| Morningglory | 0 | 0 | 0 | 0 | 9G | 8G | 5G | 2H | — | 0 | 0 | 8G | 8G | 3C,9G |
| Cocklebur | — | 0 | — | 0 | 8G | 7H | 8G | 6H | 8H | 6H | 6H | 9G | 9G | — |
| Sicklepod | 0 | 0 | 0 | 0 | 7G | 0 | 8G | 0 | 5G | 0 | 0 | 8G | 8G | 9G |
| Nutsedge | 0 | 0 | 0 | 0 | 8G | 4G | 10E | 0 | 7G | 5G | 2G | 9G | 8G | 5G |
| Crabgrass | 0 | 0 | 0 | 0 | 6G | 6G | 5G | 1C | 5G | 5G | 2C,8H | 7G | 2G | 2G |
| Barnyardgrass | 1C | 0 | 2C | 2C | 6H | 8G | 6G | 0 | 5G | 2C,8G | 2C,8G | 9H | 2C,8G | 8G |
| Wild Oats | 2G | 0 | 1C | 1C | 7G | 3C,7G | 5G | 1C | 2C,8G | 2C,8G | 3C,7G | 2C,8G | 2C,8G | 7G |
| Wheat | 7G | 2G | 2G | 3G | 2C,8G | 2C,9H | 4G | 0 | 2C,8G | 8G | 6G | 3C,9G | 8G | 6G |
| Corn | 2C,3G | 2C,6G | 2C,6G | 1H | 2H | 2C,8H | 2C,8G | 1C | 3C,9G | 2C,9G | 3C,7G | 3C,9G | 8G | 2C,8G |
| Soybean | 0 | 0 | 1H | 0 | 2H | 2H | 0 | 1C | 8H | 2H | 3H | 3C,6H | 9H | 3C,5H |
| Rice | 0 | 0 | 0 | 1C | 10E | 10E | 9H | 0 | 2H | 3C,8H | 2C,9H | 9H | 2C,4H | 2C,8G |
| Sorghum | 2C,6G | 3C,5G | 2C,5G | 3C,7G | 4C,9H | 2C,9G | 2C,8G | 6G | 2C,9H | 5C,9H | 3C,9G | 7C,9H | 2C,8G | 3C,8H |
| Sugar beet | 4G | 2H | 2H | 2H | 5G | 7G | 3G | 3G | 2C,8G | 10E | 4C,9G | 6C,9G | 3C,9G | 3C,8G |
| Cotton | 0 | 0 | 0 | 0 | 5G | 2G | 7G | 5G | 7G | 9G | 2G | 9G | 8G | 8G |

PRE-EMERGENCE

| | Cmpd. 30 | Cmpd. 31 | Cmpd. 32 | Cmpd. 33 | Cmpd. 34 | Cmpd. 35 | Cmpd. 36 | Cmpd. 37 | Cmpd. 38 | Cmpd. 39 |
|---|---|---|---|---|---|---|---|---|---|---|
| Rate kg/ha | 0.05 | 0.05 | 0.05 | 0.05 | 0.05 | 0.05 | 0.05 | 0.05 | 0.05 | 0.05 |
| Morningglory | 2G | 9G | 9G | 0 | 3G | 8G | 9G | 7G | 9G | 9G |
| Cocklebur | — | 9H | 9H | 9H | — | — | 9H | 7G | 9H | 9H |
| Sicklepod | 6G | 8G | 8G | 0 | 9G | 9G | 8G | 7G | 9G | 9G |
| Nutsedge | 4G | 5G | 0 | 0 | 10E | 0 | 10E | 10E | 9C | 10E |
| Crabgrass | 2G | 4G | 2G | 0 | 8G | 2G | 3C,8G | 0 | 0 | 4C,9G |
| Barnyardgrass | 3C,8G | 8G | 8G | 2H | 5C,9H | 2C,8H | 5C,9H | 1C | 2C,8H | 3C,9H |
| Wild Oats | 2C,7G | 2C,7G | 2C,8G | 0 | 5C,9G | 7G | 6C,9H | 5G | 7G | 4C,9G |
| Wheat | 7G | 5C,9G | 8G | 1C | 10E | 8G | 6C,9H | 4G | 5G | 5C,9H |
| Corn | 8G | 2C,8G | 8G | 1C | 10H | 8G | 4C,9G | 4G | 4G | 4C,9G |
| Soybean | 2C,2H | 3C,6G | 4C,5H | 3G | 9H | 3C,8H | 9G | 2G | 2G | 9H |
| Rice | 4C,9H | 8G | 7G | 3H | 10E | 8H | 10E | 10E | 9H | 10E |
| Sorghum | 2C,8G | 2C,9G | 2C,9G | 5G | 5C,9H | 3C,9G | 7C,9H | 4G | 4G | 5C,9G |
| Sugar beet | 2C,7G | 3C,8G | 9C | 0 | 9C | 3C,8G | 6C,9G | 5G | 5G | 5C,9G |
| Cotton | 6G | 8G | 8G | 0 | 9G | 2G | 9G | 8G | 8G | 9G |

TEST B

Post-emergence

Two round pans (25 cm diameter by 12.5 cm deep) were filled with Woodstown sandy loam soil. One pan was planted with blackgrass (*Alopecurus myosuroides*), sugarbeets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xanthium pensylvanicum*), morningglory (*Ipomoea hederacea*), Johnsongrass (*Sorghum halepense*) and barnyardgrass (*Echinochloa crusgalli*). The plants were grown for approximately fourteen days, then sprayed post-emergence with the chemicals dissolved in a non-phytotoxic solvent.

Post-emergence

Two round pans (25 cm diameter by 12.5 cm deep) were filled with Woodstown sandy loam soil. One pan was planted with blackgrass, sugarbeets, nutsedge, crabgrass, sicklepod, teaweed, jimsonweed, velvetleaf and giant foxtail. The other pan was planted with wheat, cotton, rice, corn, soybean, wild oats, cocklebur, morninggrass, johnsongrass and barnyardgrass. The two pans were sprayed pre-emergence with the chemicals dissolved in a non-phytotoxic solvent.

Treated plants and controls were maintained in the greenhouse for 28 days, then all treated plants were compared to controls and visually rated for plant response. The rating system was as described for Test A.

The data show that several of the compounds tested have utility for selective weed control in crops such as wheat and cotton.

TABLE B

| | Compound 1 | | | | Compound 3 | | | Compound 5 | | | | Compound 6 | | | | Compound 8 | | | Compound 10 | |
|---|---|---|---|---|---|---|---|---|---|---|---|---|---|---|---|---|---|---|---|---|
| Rate g/ha | 250 | 62 | 16 | 4 | 62 | 16 | 4 | 250 | 62 | 16 | 4 | 250 | 62 | 16 | 4 | 62 | 16 | 4 | 62 | 16 |
| | | | | | | | | Post-Emergence | | | | | | | | | | | | |
| Corn | 9G | 7G | 4G | 2G | 8G | 5G | 0 | 10C | 10C | 9G | 5G | 10C | 10C | 10G | 5G | 9G | 3G | 0 | 10G | 10C |
| Wheat | 0 | 0 | 0 | 0 | 9G | 5G | 0 | 10C | 9C | 3G | 0 | 10C | 10G | 6G | 0 | 6G | 4G | 0 | 10C | 10C |
| Rice | 5G | 2G | 0 | 0 | 9G | 6G | 4G | 10C | 10G | 6G | 0 | 10C | 10C | 10C | 7G | 8G | 3G | 0 | 10C | 10C |
| Soybeans | 10G | 9G | 9G | 7G | 9G | 8G | 3G | 10C | 10G | 10G | 6G | 10G | 10G | 10G | 5G | 9G | 8G | 4G | 10G | 10G |
| Cotton | 10C | 10C | 10C | 10G | 6G | 0 | 0 | 6G | 3G | 0 | 0 | 10G | 10G | 9G | 5G | 5G | 0 | 0 | 10C | 10G |
| Sugar beets | 10C | 10C | 10C | 10C | 10G | 9G | 3G | 10C | 10C | 10C | 5G | 10C | 10C | 10C | 8G | 10C | 8G | 3G | 10C | 10G |
| Crabgrass | 5G | 2G | 0 | 0 | 8G | 4G | 2G | 7G | 2G | 0 | 0 | 10C | 8G | 4G | 0 | 0 | 0 | 0 | 10C | 9G |
| Johnsongrass | 7G | 6G | 3G | 0 | 9G | 8G | 2G | 10C | 10C | 0 | 0 | 10C | 10C | 6G | 3G | 10G | 10G | 4G | 10C | 10C |
| Blackgrass | 8G | 6G | 4G | 0 | 8G | 5G | 0 | 10C | 10C | 0 | 0 | 10C | 10C | 10G | 5G | 4G | 0 | 0 | 10C | 10C |
| Barnyardgrass | 2G | 0 | 0 | 0 | 9G | 4G | 0 | 10C | 10C | 9G | 3G | 10C | 10C | 7G | 2G | 0 | 0 | 0 | 10G | 10G |
| Nutsedge | 10C | 10C | 9C | 6C | 8G | 4G | 0 | 9C | 9C | 4G | 0 | 10C | 10C | 9C | 3G | 0 | 0 | 0 | 10C | 9C |
| Giant foxtail | — | — | — | — | — | — | — | 10C | 10C | 7G | 4G | 10C | 7G | 5G | 2G | 3G | 0 | 0 | 10C | 10G |
| Wild Oats | 0 | 0 | 0 | 0 | 9G | 2G | 0 | 9C | 5G | 0 | 0 | 10C | 9G | 6G | 0 | 9G | 5G | 0 | 10C | 10C |
| Cocklebur | 10C | 10C | 10C | 10G | 10G | 3G | 0 | 10C | 10G | 10G | 7G | 10G | 10G | 9G | 8G | 9G | 8G | 2G | 10G | 10G |
| Morningglory | 10C | 10C | 10C | 10C | 7G | 4G | 2C | 10C | 10G | 8G | 3G | 10G | 10G | 9G | 6G | 8G | 6G | 0 | 10G | 9G |
| Teaweed | 10G | 10G | 10G | 6G | 10G | 4G | 0 | 5G | 0 | 0 | 0 | 10G | 6G | 4G | 0 | 3G | 0 | 0 | 10G | 7G |
| Sicklepod | 10G | 10G | 10G | 7G | 7G | 2G | 0 | 6G | 2G | 0 | 0 | 10G | 7G | 3G | 3G | 3G | 0 | 0 | 10G | 10G |
| Jimsonweed | 10C | 10C | 10G | 7G | 10G | 7G | 5G | 10G | 10C | 5G | 3G | 10C | 10G | 10G | 7G | 9G | 6G | 2G | 9G | 5G |
| Velvetleaf | 10C | 10C | 10C | 9G | 6G | 3G | 0 | 3G | 0 | 0 | 0 | 10C | 10G | 8G | 4G | 4G | 0 | 0 | 10C | 8G |

| | | Compound 10 | | Compound 14 | | | | Compound 24 | | | | Compound 37 | | | |
|---|---|---|---|---|---|---|---|---|---|---|---|---|---|---|---|
| | Rate g/ha | 4 | 1 | 250 | 62 | 16 | 4 | 250 | 62 | 16 | 4 | 62 | 16 | 4 | 1 |
| | | | | | | | Post-Emergence | | | | | | | | |
| | Corn | 7G | 4G | 10B | 10G | 4G | 0 | 10C | 10C | 9G | 7G | 10C | 10G | 10C | 5G |
| | Wheat | 6G | 0 | 5G | 0 | 0 | 0 | 0 | 0 | 0 | 0 | 7G | 3G | 0 | 0 |
| | Rice | 10G | 10C | 9B | 8G | 7G | 3G | 10G | 9G | 8G | 4G | 10G | 9G | 6G | 2G |
| | Soybeans | 8G | 3G | 10G | 8G | 3G | 0 | 9G | 7G | 3G | 0 | 10G | 10G | 10G | 6G |
| | Cotton | 6G | 2G | 9G | 8H | 2G | 0 | 7G | 4G | 0 | 0 | 10G | 10G | 5G | 0 |
| | Sugar beets | 8G | 5G | 9B | 4G | 2G | 0 | 9G | 8G | 4G | 0 | 10C | 10C | 10C | 10C |
| | Crabgrass | 5G | 3G | 10B | 3G | 0 | 0 | 2G | 0 | 0 | 0 | 8G | 4G | 2G | 0 |
| | Johnsongrass | 10C | 4G | 10B | 8B | 3G | 0 | 8G | 3G | 0 | 0 | 10C | 10C | 6G | 3G |
| | Blackgrass | 9G | 8G | 9B | 9B | 3G | 0 | 6G | 2G | 0 | 0 | 10C | 9G | 4G | 2G |
| | Barnyardgrass | 10C | 4G | 9B | 8B | 4G | 2G | 7G | 7G | 7G | 5G | 10C | 10C | 5G | 2G |
| | Nutsedge | 5G | 0 | 5G | 2G | 0 | 0 | 0 | 0 | 0 | 0 | 10C | 10C | 9G | 4G |
| | Giant foxtail | 4G | 0 | 9B | 6G | 2G | 0 | 9G | 7G | 2G | 0 | 10G | 7G | 3G | 0 |
| | Wild Oats | 6G | 4G | 4G | 0 | 0 | 0 | 0 | 0 | 0 | 0 | 8G | 2G | 0 | 0 |
| | Cocklebur | 8G | 3G | 8G | 4G | 2G | 0 | 9G | 9G | 9G | 6G | 9G | 7G | 2G | 0 |
| | Morningglory | 4G | 0 | 9G | 2C | 0 | 0 | 2C | 2G | 0 | 0 | 10G | 10G | 9G | 5G |
| | Teaweed | 2G | 0 | 2C | 0 | 0 | 0 | 4G | 2G | 0 | 0 | 9G | 6G | 3G | 0 |
| | Sicklepod | 10G | 5G | 2G | 0 | 0 | 0 | 2G | 0 | 0 | 0 | 10C | 9G | 4G | 0 |
| | Jimsonweed | 2G | 0 | 4G | 2G | 0 | 0 | 0 | 0 | 0 | 0 | 10G | 9G | 9G | 7G |
| | Velvetleaf | 7G | 2G | 8G | 4G | 2G | 0 | 8G | 6G | 3G | 0 | 10C | 10C | 8G | 3G |

| | Compound 1 | | Compound 3 | | Compound 5 | | | Compound 6 | | | Compound 8 | | Compound 10 | | | Compound 11 |
|---|---|---|---|---|---|---|---|---|---|---|---|---|---|---|---|---|
| Rate g/ha | 250 | 62 | 62 | 16 | 250 | 62 | 16 | 250 | 62 | 16 | 4 | 62 | 16 | 62 | 16 | 4 | 1 | 250 |
| | | | | | | | Pre-Emergence | | | | | | | | | | |
| Corn | 7G | 4G | 0 | 0 | 10G | 2G | 0 | 10E | 10G | 3G | 0 | 8G | 2G | 10G | 10G | 8G | 2G | 7G |
| Wheat | 0 | 0 | 2G | 0 | 9G | 7G | 3G | 9G | 7G | 3G | 0 | 0 | 0 | 10G | 10G | 5G | 3G | 5G |
| Rice | 10G | 7G | 7G | 3G | 10E | 10G | 5G | 10E | 10E | 10E | 7G | 8G | 2G | 10E | 10E | 10E | 9G | 8G |
| Soybean | 8G | 4G | 2C | 0 | 9G | 2G | 0 | 8G | 5G | 2G | 0 | 4G | 0 | 9G | 6G | 4G | 0 | 6G |
| Cotton | 10G | 7G | 0 | 0 | 0 | 0 | 0 | 3G | 2G | 0 | 0 | 0 | 0 | 9G | 4G | 2G | 0 | 2G |

TABLE B-continued

| | | | | | | | | | | | | | | | | | | |
|---|---|---|---|---|---|---|---|---|---|---|---|---|---|---|---|---|---|---|
| Sugar beets | 10G | 9G | 7G | 0 | 10G | 10G | 5G | 10E | 10E | 10E | 3G | 9G | 3G | 10G | 10G | 8G | 3G | 9G |
| Crabgrass | 6G | 3G | 4G | 0 | 10G | 4G | 0 | 9G | 8G | 5G | 0 | 3G | 0 | 10G | 10G | 5G | 0 | 2G |
| Johnsongrass | 6G | 5G | 7G | 4G | 10G | 8G | 2G | 10C | 9G | 8G | 2G | 9G | 3G | 10C | 10G | 9G | 3G | 7G |
| Blackgrass | 8G | 6G | 3G | 2G | 0 | 0 | 0 | 10E | 10E | 7G | 3G | 0 | 0 | 10E | 10E | 10G | 5G | 9G |
| Barnyardgrass | 4G | 2G | 4G | 2G | 10G | 7G | 4G | 10G | 10G | 3G | 0 | 4G | 0 | 10G | 10G | 8G | 2G | 3G |
| Nutsedge | 10E | 8G | 3G | 0 | 8G | 2G | 0 | 10E | 10E | 5G | 0 | 0 | 0 | 10E | 10E | 5G | 0 | 8G |
| Giant foxtail | 10E | 4G | 8G | 6G | 9G | 9G | 3G | 10E | 10G | 3G | 0 | 0 | 0 | 10E | 10G | 10G | 4G | 2G |
| Wild Oats | 0 | 0 | 3G | 0 | 9G | 5G | 3G | 10G | 8G | 5G | 3G | 3G | 0 | 9G | 8G | 5G | 3G | 3G |
| Cocklebur | 10G | 8G | 4G | 0 | 6G | 2G | 0 | 10G | 7G | 2G | 0 | 0 | 0 | 10G | 9G | 5G | 0 | 2G |
| Morningglory | 10G | 7G | 0 | 0 | 3G | 0 | 0 | 3G | 4G | 0 | 0 | 0 | 0 | 9G | 6G | 2G | 0 | 3G |
| Teaweed | 9G | 7G | 5G | 3G | 6G | 4G | 0 | 10G | 5G | 0 | 0 | 2G | 0 | 9G | 5G | 0 | 0 | 4G |
| Sicklepod | 9G | 6G | 7G | 4G | 10E | 3G | 0 | 10E | 6G | 2G | 0 | 3G | 0 | 10E | 10G | 4G | 0 | 0 |
| Jimsonweed | 10G | 9G | 2G | 0 | 8G | 4G | 0 | 10G | 7G | 3G | 0 | 0 | 0 | 10G | 8G | 5G | 0 | 8G |
| Velvetleaf | 10G | 8G | 0 | 0 | 7G | 3G | 0 | 10G | 8G | 3G | 0 | 0 | 0 | 10G | 10G | 7G | 0 | 5G |

| | Compound 11 | | Compound 14 | | | | Compound 24 | | Compound 37 | | |
|---|---|---|---|---|---|---|---|---|---|---|---|
| Rate g/ha | 62 | 16 | 250 | 62 | 16 | 4 | 250 | 62 | 62 | 16 | 4 |
| | Pre-Emergence | | | | | | | | | | |
| Corn | 2G | 0 | 8G* | 5G | 2C | 0 | 6G | 2G | 8G | 4G | 0 |
| Wheat | 2G | 0 | 6G | 3G | 0 | 0 | 2G | 0 | 5G | 3G | 0 |
| Rice | 7G | 5G | 10G | 10G | 6G | 2C | 6G | 4G | 10G | 9G | 5G |
| Soybean | 2C | 0 | 6C | 4G | 3G | 2G | 2G | 0 | 10G | 5G | 2G |
| Cotton | 0 | 0 | 3C | 0 | 0 | 0 | 3G | 2G | 8G | 4G | 0 |
| Sugar beets | 4G | 2G | 5G | 2G | 0 | 0 | 4G | 2G | 10G | 4G | 0 |
| Crabgrass | 0 | 0 | 9G | 9G | 3G | 0 | 5G | 3G | 7G | 2G | 0 |
| Johnsongrass | 4G | 2G | 9G | 5G | 0 | 0 | 8G | 4G | 10G | 8G | 2G |
| Blackgrass | 5G | 3G | 9G | 6G | 3C | 0 | 5G | 2G | 10G | 8G | 3G |
| Barnyardgrass | 0 | 0 | 9G | 5G | 0 | 0 | 5G | 2G | 9G | 6G | 2G |
| Nutsedge | 6G | 2G | 6G | 3G | 2C | 0 | 4G | 2G | 9G | 4G | 2G |
| Giant foxtail | 0 | 0 | 9G | 5G | 0 | 0 | 6G | 2G | — | — | — |
| Wild Oats | 0 | 0 | 5G | 2G | 0 | 0 | 4G | 2G | 3G | 0 | 0 |
| Cocklebur | 0 | 0 | 6G | 4G | 2G | 0 | 5G | 2G | 9G | 2G | 0 |
| Morningglory | 0 | 0 | 7C | 3C | 2G | 0 | 4G | 2G | 5G | 2G | 0 |
| Teaweed | 2G | 0 | 6G | 3G | 0 | 0 | 5G | 3G | 9G | 3G | 0 |
| Sicklepod | 0 | 0 | 5G | 2G | 0 | 0 | 2G | 0 | 8G | 4G | 2G |
| Jimsonweed | 5G | 2G | 3G | 2G | 0 | 0 | 4G | 2G | 9G | 2G | 0 |
| Velvetleaf | 2G | 0 | 7G | 4G | 2G | 0 | 5G | 3G | 9G | 6G | 0 |

What is claimed is:

1. A compound of the formula:

$$L-SO_2NHCN-A$$
$$\underset{R}{|} \overset{\overset{O}{\|}}{}$$

wherein
R is H or $CH_3$;
L is

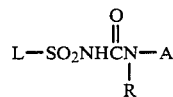  L-1

$R_1$ is $C_1$-$C_4$ alkyl, $C_1$-$C_4$ alkoxy, $OCH_2CH_2OCH_3$, F, Cl, Br, $NO_2$, $CF_3$, $CO_2R_{15}$, $SO_2NR_{16}R_{17}$, $SO_2N(OCH_3)CH_3$, $OSO_2R_{18}$, $S(O)_nR_{19}$, $WCF_3$, $WCHF_2$, $C_3$-$C_4$ alkenyloxy, $C_3$-$C_4$ alkynyloxy, $C_6H_5$, $C_1$-$C_2$ alkyl substituted with $OCH_3$ or $OCH_2CH_3$,

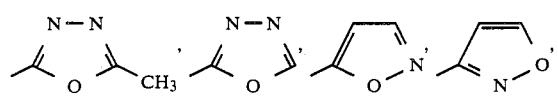

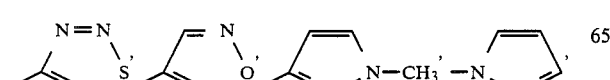

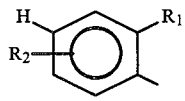 or 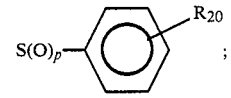;

$R_2$ is H, F, Cl, Br, $CF_3$, $CH_3$, $OCH_3$ or $SCH_3$;
$R_{15}$ is $C_1$-$C_4$ alkyl, $CH_2CH_2OCH_3$, $CH_2CH_2Cl$ or $CH_2CH=CH_2$;
$R_{16}$ is $C_1$-$C_2$ alkyl;
$R_{17}$ is $C_1$-$C_2$ alkyl;
$R_{18}$ is $C_1$-$C_3$ alkyl or $N(CH_3)_2$;
$R_{19}$ is $C_1$-$C_3$ alkyl or $CH_2CH=CH_2$; and
W is O, S or $SO_2$;
A is

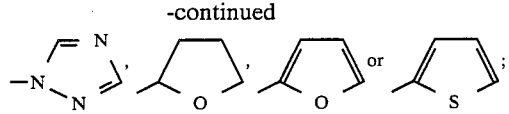  A-1

X is $CH_3$, $OCH_3$, $OC_2H_5$, F, Cl, Br, $CF_3$ or $OCHF_2$;
T is H, $SeCH_3$, $SeC_6H_5$, $SCH_3$ or

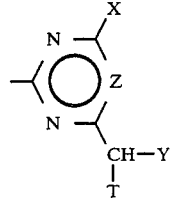;

Y is $SeCH_3$, $SeO_6H_5$,

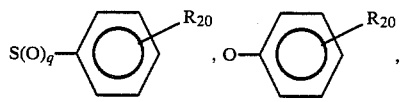

OSi(CH$_3$)$_3$, CH$_2$OH or CH$_2$OSi(CH$_3$)$_3$;
Z is CH;
R$_{20}$ is H, CH$_3$, CF$_3$, OCH$_3$, F, Cl, Br or NO$_2$;
p is 0, 1 or 2; and
q is 0, 1 or 2;
provided that
the sum of p and q is less than or equal to 2;
and their agriculturally suitable salts.

2. A compound of claim 1 wherein R is H.

3. A compound of claim 2 wherein R$_2$ is H, R$_{20}$ is H, X is CH$_3$ or OCH$_3$, T is H, p is 0 and q is 0.

4. A compound of claim 3 wherein R$_1$ is C$_1$–C$_2$ alkyl, C$_1$–C$_2$ alkoxy, Cl, NO$_2$, CO$_2$CH$_3$, CO$_2$C$_2$H$_5$, SO$_2$N(CH$_3$)$_2$, SO$_2$CH$_3$, OSO$_2$CH$_3$ or WCHF$_2$.

5. The compound of claim 1 which is 2-[[[4-methoxy-6-(phenoxymethyl)pyrimidin-2-yl]aminocarbonyl]aminosulfonyl]benzoic acid, methyl ester.

6. The compound of claim 1 which is 2-[[[4-methoxy-6-(methylselenylmethyl)pyrimidin-2-yl]aminocarbonyl]aminosulfonyl]benzoic acid, methyl ester.

7. The compound of claim 1 which is 2-[[[4-methoxy-6-(phenylthiomethyl)pyrimidin-2-yl]aminocarbonyl]aminosulfonyl]benzoic acid, methyl ester.

8. A composition suitable for controlling the growth of undesired vegetation which comprises an effective amount of a compound of claim 1 and at least one of the following: surfactant, solid or liquid inert diluent.

9. A composition suitable for controlling the growth of undesired vegetation which comprises an effective amount of a compound of claim 2 and at least one of the following: surfactant, solid or liquid inert diluent.

10. A composition suitable for controlling the growth of undesired vegetation which comprises an effective amount of a compound of claim 3 and at least one of the following: surfactant, solid or liquid inert diluent.

11. A composition suitable for controlling the growth of undesired vegetation wich comprises an effective amount of a compound of claim 4 and at least one of the following: surfactant, solid or liquid inert diluent.

12. A method for controlling the growth of undesired vegetation which comprises applying to the locus to be protected an effective amount of a compound of claim 1.

13. A method for controlling the growth of undesired vegetation which comprises applying to the locus to be protected an effective amount of a compound of claim 2.

14. A method for controlling the growth of undesired vegetation which comprises applying to the locus to be protected an effective amount of a compound of claim 3.

15. A method for controlling the growth of undesired vegetation which comprises applying to the locus to be protected an effective amount of a compound of claim 4.

* * * * *